US012637636B2

(12) United States Patent
Andersen et al.

(10) Patent No.: US 12,637,636 B2
(45) Date of Patent: *May 26, 2026

(54) ALPHA-AMYLASE VARIANTS AND POLYNUCLEOTIDES ENCODING SAME

(71) Applicant: Novozymes A/S, Bagsvaerd (DK)

(72) Inventors: Carsten Andersen, Bagsvaerd (DK);
Vivek Srivastava, Bagsvaerd (DK);
Padmavathi Balumuri, Chennai (IN);
Partha Pratim Chakrabarti,
Bangalore (IN); Sohel Dalal,
Ahmedabad (IN)

(73) Assignee: Novozymes A/S, Bagsvaerd (DK)

( * ) Notice: Subject to any disclaimer, the term of this
patent is extended or adjusted under 35
U.S.C. 154(b) by 36 days.

This patent is subject to a terminal dis-
claimer.

(21) Appl. No.: 18/657,713

(22) Filed: May 7, 2024

(65) Prior Publication Data

US 2024/0287419 A1     Aug. 29, 2024

Related U.S. Application Data

(62) Division of application No. 17/745,997, filed on May
17, 2022, now Pat. No. 12,018,237, which is a
division of application No. 16/394,265, filed on Apr.
25, 2019, now Pat. No. 11,365,375, which is a
division of application No. 15/571,193, filed as
application No. PCT/EP2016/060267 on May 9,
2016, now Pat. No. 10,316,275.

(30) Foreign Application Priority Data

May 8, 2015     (IN) ........................... 2336/CHE/2015

(51) Int. Cl.
*C11D 3/386*          (2006.01)
*C12N 9/28*           (2006.01)
(52) U.S. Cl.
CPC .......... *C11D 3/38681* (2013.01); *C11D 3/386*
(2013.01); *C11D 3/38663* (2013.01); *C12N*
*9/2417* (2013.01); *C12Y 302/01001* (2013.01);
*C11D 3/38627* (2013.01); *C11D 3/38645*
(2013.01); *C11D 3/38654* (2013.01)
(58) Field of Classification Search
CPC . C11D 3/38681; C11D 3/386; C11D 3/38663;
C11D 3/38627; C11D 3/38645; C11D
3/38654; C12N 9/2417; C12Y 302/01001
See application file for complete search history.

(56) References Cited

U.S. PATENT DOCUMENTS

| | | | |
|---|---|---|---|
| 3,642,582 | A | 2/1972 | McClary et al. |
| 5,824,531 | A | 10/1998 | Outtrup et al. |
| 5,856,164 | A | 1/1999 | Outtrup et al. |
| 6,093,562 | A | 7/2000 | Bisgård-Frantzen et al. |
| 6,187,576 | B1 | 2/2001 | Svendsen et al. |
| 6,197,565 | B1 | 3/2001 | Svendsen et al. |
| 6,204,232 | B1 | 3/2001 | Borchert et al. |
| 6,297,038 | B1 | 10/2001 | Bisgård-Frantzen et al. |
| 6,309,871 | B1 | 10/2001 | Outtrup et al. |
| 6,361,989 | B1 | 3/2002 | Svendsen et al. |
| 6,623,948 | B1 | 9/2003 | Outtrup et al. |
| 7,713,723 | B1 | 5/2010 | Thisted et al. |
| 8,080,401 | B2 * | 12/2011 | Bessler ................ C12N 9/2417 |
| | | | 435/263 |
| 9,096,837 | B2 * | 8/2015 | Andersen ............. C12N 9/2417 |
| 9,896,673 | B2 | 2/2018 | Svendsen et al. |
| 9,902,946 | B2 | 2/2018 | Andersen |
| 10,316,275 | B2 | 6/2019 | Andersen et al. |
| 10,647,946 | B2 | 5/2020 | Andersen et al. |
| 11,319,509 | B2 | 5/2022 | Andersen et al. |
| 11,365,375 | B2 * | 6/2022 | Andersen ........... C11D 3/38681 |
| 12,018,237 | B2 * | 6/2024 | Andersen ....... C12Y 302/01001 |
| 2003/0211958 | A1 | 11/2003 | Svendsen et al. |
| 2003/0224964 | A1 | 12/2003 | Gosselink et al. |
| 2004/0096952 | A1 | 5/2004 | Svendsen et al. |
| 2008/0193999 | A1 | 8/2008 | Andersen et al. |
| 2009/0104681 | A1 | 4/2009 | Bower et al. |
| 2010/0112637 | A1 | 5/2010 | Borchert et al. |
| 2011/0059492 | A1 | 3/2011 | Duan et al. |
| 2011/0171694 | A1 | 7/2011 | Thisted et al. |
| 2012/0045822 | A1 | 2/2012 | Concar et al. |
| 2013/0000055 | A1 | 1/2013 | Jackson et al. |
| 2015/0031091 | A1 | 1/2015 | Li et al. |
| 2015/0044754 | A1 | 2/2015 | Sun et al. |
| 2016/0083703 | A1 | 3/2016 | Andersen et al. |

FOREIGN PATENT DOCUMENTS

| | | |
|---|---|---|
| CN | 1278298 A | 12/2000 |
| CN | 102869759 A | 1/2013 |
| CN | 103275951 A | 9/2013 |
| CN | 103649307 A | 3/2014 |

(Continued)

OTHER PUBLICATIONS

Aehle et al., 2009, WO2008153805—EBI Accession No. GM992869.
Andersen et al., 2014, WO2014183921—EBI Accession No.
BBQ10961.
Andersen et al., 2017, WO2016203064—EBI Accession No.
BDL38757.
Andersen et al., 2017, WO2016203064—EBI Accession No.
BDL38758.
Andersen et al., 2017, WO2016203064—EBI Accession No.
BDL38759.

(Continued)

*Primary Examiner* — Ganapathirama Raghu

(74) *Attorney, Agent, or Firm* — Yoshimi D. Barron

(57) ABSTRACT

The present invention relates to alpha-amylase variants. The
present invention also relates to polynucleotides encoding
the variants; nucleic acid constructs, vectors, and host cells
comprising the polynucleotides; and methods of using the
variants.

28 Claims, 3 Drawing Sheets

Specification includes a Sequence Listing.

(56) References Cited

FOREIGN PATENT DOCUMENTS

| CN | 105209613 | A | 12/2015 |
|---|---|---|---|
| EP | 1160327 | A2 | 12/2001 |
| JP | 1999500003 | A | 1/1999 |
| JP | 11503003 | A | 3/1999 |
| JP | 2002540784 | A | 12/2002 |
| WO | 1994018314 | A1 | 8/1994 |
| WO | 1995010603 | A1 | 4/1995 |
| WO | 1995026397 | A1 | 10/1995 |
| WO | 1996023873 | A1 | 8/1996 |
| WO | 1996023874 | A1 | 8/1996 |
| WO | 1997000324 | A1 | 1/1997 |
| WO | 1997032961 | A2 | 9/1997 |
| WO | 1998005748 | A1 | 2/1998 |
| WO | 2000060058 | A2 | 10/2000 |
| WO | 2000060060 | A2 | 10/2000 |
| WO | 2001018180 | A2 | 3/2001 |
| WO | 2001064852 | A1 | 9/2001 |
| WO | 2001066712 | A2 | 9/2001 |
| WO | 2002042740 | A1 | 5/2002 |
| WO | 2006002643 | A2 | 1/2006 |
| WO | 2008000825 | A1 | 1/2008 |
| WO | 2008153805 | A2 | 12/2008 |
| WO | 2009102854 | A1 | 8/2009 |
| WO | 2011036263 | A1 | 3/2011 |
| WO | 2011080353 | A1 | 7/2011 |
| WO | 2011098531 | A1 | 8/2011 |
| WO | 2013001078 | A1 | 1/2013 |
| WO | 2013001087 | A2 | 1/2013 |
| WO | 2014106593 | A1 | 7/2014 |
| WO | 2014162001 | A1 | 10/2014 |
| WO | 2014183920 | A1 | 11/2014 |
| WO | 2014183921 | A1 | 11/2014 |
| WO | 2015044448 | A1 | 4/2015 |
| WO | 2015144782 | A1 | 10/2015 |
| WO | 2015149641 | A1 | 10/2015 |
| WO | 2015189370 | A1 | 12/2015 |
| WO | 2015189371 | A1 | 12/2015 |
| WO | 2016203064 | A2 | 12/2016 |

OTHER PUBLICATIONS

Andersen, 2014, WO2014106593—EBI Accession No. BBK44028.
Andersen, 2014, WO2014106593—EBI Accession No. BBK44106.
Broun et al., 1998, Science, 282, 1315-1317.
Davail et al., 1994, The Journal of Biological Chemistry, 269(26), 17448-17453.
Devos et al., 2000, Proteins: Structure, Function, and Genetics, 41, 98-107.
Igarashi et al., 1998, Biochemical and Biophysical Research Communications, 248(2), 372-377.
Jeang et al., 2000, Uniprot database accession No. Q9RQT8.
Kao Corporation, 1997, Abstract of JP08336392.
Lin et al., 1996, Uniprot No. Q59222.
Miao et al., 2007, Science and Technology of Food Industry, 28(10), 63-65 and 69.
Narinx et al., 1997, Protein Engineering, 10(11), 1271-1279.
Novo Nordisk et al., 1999, Abstract of JP11503003, Derwent accession No. 1996371423.
Novozymes A/S, 2015, WO2014183921A1, EBI Accession No. BBQ10987.
Olsen et al., 1998, Journal of Surfactants and Detergents, 1(4), 555-567.
Olsen et al., 2003, Geneseq Database, accession No. AAY97812.
Outtrup et al., 2001, WO2000060058—EBI Accession No. AAA97708.
Outtrup et al., 2001, WO2000060058—EBI Accession No. AAB29327.
Outtrup et al., 2001, WO2000060058—EBI Accession No. AAB29363.
Seffernick et al., 2001, Journal of Bacteriology, 183(8), 2405-2410.
Siezen et al., 1997, Protein Science, 6, 501-523.
Singh et al., 2017, Current Protein and Peptide Science, 18, 1-11.
Svendsen et al., 2008, EBI Accession No. ACE45183.
Svendsen et al., 2012, EBI Accession No. AFS96539.
Tsukamoto et al., 1988, Biochemical and Biophysical Research Communications, 151(1), 25-31.
Tsukamoto et al., 1991, Uniprot accession No. P19571.
Tsukamoto et al., 1993, GenEmbl Database accession No. M18862.
Wang et al., 2014, Uniprot, Accession No. A0A074LY65.
Whisstock et al., 2003, Quarterly Reviews Biophysics, 36(3), 307-340.
Witkowski et al., 1999, Biochemistry, 38(36), 11643-11650.
Zhang et al., 2018, Structure, 26, 1474-1485.

* cited by examiner

ALPHA-AMYLASE VARIANTS AND POLYNUCLEOTIDES ENCODING SAME

CROSS-REFERENCE TO RELATED APPLICATIONS

This application is a divisional of U.S. application Ser. No. 17/745,997 filed May 17, 2022 (now pending), which is a divisional of U.S. application Ser. No. 16/394,265 filed Apr. 25, 2019 (now U.S. Pat. No. 11,365,375) which is a divisional of U.S. application Ser. No. 15/571,193 filed Nov. 1, 2017 (now U.S. Pat. No. 10,316,275) which is a 35 U.S.C. 371 national application of international application no. PCT/EP2016/060267 filed May 9, 2016, which claims priority or the benefit under 35 U.S.C. 119 of Indian application no. 2336/CHE/2015 filed May 8, 2015, the contents of which are fully incorporated herein by reference.

REFERENCE TO A SEQUENCE LISTING

This application contains a Sequence Listing in computer readable form. The contents of the electronic sequence listing created on May 6, 2024, named SQ.xml and is 10,008 bytes in size, is hereby incorporated by reference in its entirety.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (α-1,4-glucan-4-glucanohydrolases, E.C. 3.2.1.) are a group of enzymes that hydrolyzes starch, glycogen, and other related polysaccharides by cleaving the internal α-1,4-glucosidic bonds. It has been used for many years been in, e.g., laundry where is it well-known that alpha-amylases have a beneficial effect in removal of starch containing, or starch-based, stains. However, in other commercial applications the enzyme has become important, such as in the initial stages (liquefaction) of starch processing, in textile desizing, in alcohol production and as cleaning agents in detergent compositions.

In recent years there has been a desire to improve the properties of various amylases. In particular, the object of reducing the temperature of the laundry in order to reduce the energy consumption has been of primary focus when referring to the householdcare sector. Thus, many efforts have been put into finding improved alpha-amylase variants.

Regardless, there remains a need for alpha-amylase variants that posses altered properties, and offer improved performance in various industrial applications. Thus, the present invention provides such further improved alpha-amylase variants with improved properties compared to its parent.

SUMMARY OF THE INVENTION

The present invention relates to an alpha-amylase variant of a parent polypeptide having alpha-amylase activity, wherein the variant is a mature form of an alpha-amylase having amylase activity, and comprising a substitution at one or more positions selected from the group consisting of: H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3; and wherein the substitution at the one or more positions provides an alpha-amylase variant having an improvement factor of ≥1.0 for a measure of stability, and/or an improvement factor of ≥1.0 for a measure of specific activity.

The present invention also relates to polynucleotides encoding the variants; nucleic acid constructs, vectors, and host cells comprising the polynucleotides; and methods of producing the variants.

The present invention also relates to methods of improving wash performance and/or stability of a parent alpha-amylase.

CONVENTIONS FOR DESIGNATION OF VARIANTS

Figure 1:
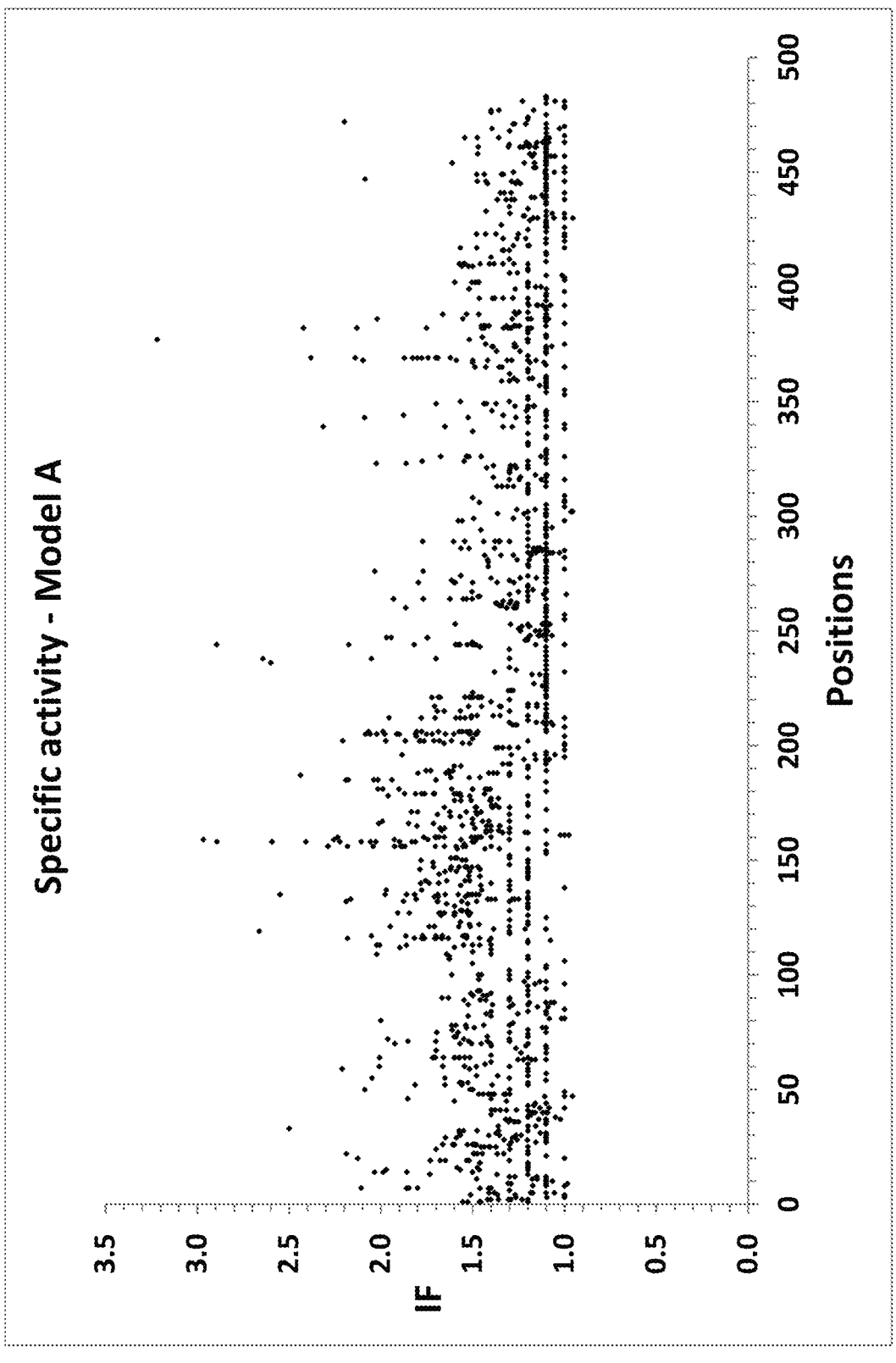
FIG. 1 shows the Improvement Factor (IF) for a measure of specific activity of the variants according to the present invention tested in a Model A detergent. The individual position modified is given as the X axis and the specific IF for each variant is given on the Y axis.

For purposes of the present invention, the mature polypeptide set forth in SEQ ID NO: 3 is used to determine the corresponding amino acid residue in another alpha-amylase. The amino acid sequence of another alpha-amylase is aligned with the mature polypeptide set forth in SEQ ID NO: 3, and based on the alignment, the amino acid position number corresponding to any amino acid residue in the mature polypeptide set forth in SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLO-SUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, Methods in Molecular Biology 537: 39-64; Katoh and Toh, 2010, Bio-informatics 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide set forth in SEQ ID NO: 3 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions: For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions: For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195 | 195 195a 195b |
| G | G - K - A |

Multiple modifications: Variants comprising multiple modifications are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different modifications: Where different modifications may be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" des-
ignates the following variants:

"Tyr167Gly+Arg170Gly",     "Tyr167Gly+Arg170Ala",
    "Tyr167Ala+Arg170Gly",   and     "Tyr167Ala+
    Arg170Ala".

DETAILED DESCRIPTION OF THE INVENTION

The present invention relates to a set of sequences. For ease, these are listed below:

SEQ ID NO: 1 is the nucleotide sequence of a mature alpha-amylase (AAI10)

SEQ ID NO: 2 is the amino acid sequence of AAI10 including the signal peptide, i.e. full-length.

SEQ ID NO: 3 is the amino acid sequence of the mature AAI10.

SEQ ID NO: 4 is the amino acid sequence of the mature AAI10 comprising a double deletion of the positions corresponding to positions G182 and D183 of SEQ ID NO: 3.

SEQ ID NO: 5 is a PnMi4490 forward primer.

SEQ ID NO: 6 is a PnMi4491 forward primer.

Variants of the Invention

In one aspect, the present invention relates to variants of a parent polypeptide having alpha-amylase activity. Thus, in particular aspect, the present invention relates to an alpha-amylase variant of a parent alpha-amylase having alpha-amylase activity, wherein said variant is a mature form of an alpha-amylase having amylase activity, and comprising a substitution at one or more positions selected from the group consisting of: H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3; and wherein the substitution at the one or more positions provides an alpha-amylase variant having an improvement factor of ≥1.0 for a measure of stability, and/or an improvement factor of ≥1.0 for a measure of specific activity.

It has been shown that variants according to the present invention which comprise a single substitution have an improved specific activity and/or stability compared to the parent alpha-amylase.

The term "amylase" or "alpha-amylase" as used herein, refers to an enzyme capable of catalyzing the degradation of starch. Generally, alpha-amylases (E.C. 3.2.1.1, α-D-(1→4)-glucan glucanohydrolase) are endo-acting enzymes that cleave the α-D(1→4) O-glycosidic linkages within the starch molecule in a random order.

The term "starch" as used herein, refers to any material comprised of the complex polysaccharide carbohydrates of plants, comprised of amylose and amylopectin with the formula $(C_6H_{10}O_5)_x$, wherein X can be any number. In particular, the term refers to plant-based materials, such as rice, barley, wheat, corn, rye, potato, and the like.

The term "alpha-amylase variant" as used herein, refers to a polypeptide having alpha-amylase activity comprising a modification, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position, all as defined above. The variants of the present invention have at least 20%, e.g., at least 40%, at least 50%, at least 60%, at least 70%, at least 80%, at least 90%, at least 95%, or at least 100% of the alpha-amylase activity of the amino acid sequence as set forth in SEQ ID NOs: 3. The alpha-amylase variant of the present invention comprises an amino acid sequence having at least 60%, such as at least 65%, such as at least 70%, such as at least 75%, such as at least 80%, such as at least 85%, such as at least 90%, such as at least 95%, such as at least 97%, such as at least 99%, but less than 100% sequence identity to any one of SEQ ID NOs: 2, 3, or 4.

The term "alpha-amylase activity" or "amylase activity" as used herein, refers to the activity of alpha-1,4-glucan-4-glucanohydrolases, E.C. 3.2.1.1, which constitute a group of enzymes, catalyzing hydrolysis of starch and other linear and branched 1,4-glucosidic oligo- and polysaccharides. Thus, the term "alpha-amylase" as used herein, refers to an enzyme that has alpha-amylase activity (Enzyme Class; EC 3.2.1.1) that hydrolyses alpha bonds of large, alpha-linked polysaccharides, such as starch and glycogen, yielding glucose and maltose. The terms "alpha-amylase" and "amylase" may be used interchangeably and constitute the same meaning and purpose within the scope of the present invention. For purposes of the present invention, alpha-amylase activity is determined according to the procedure described in the Examples. In one embodiment, the variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NOs: 3 or 4; or the mature polypeptide of SEQ ID NO: 2.

The term "parent alpha-amylase" as used herein, refers to an alpha-amylase to which an alteration is made to produce enzyme variants. The alpha-amylase having an amino acid sequence as set forth in SEQ ID NOs: 2, 3 or 4, may e.g. be a parent for the variants of the present invention. Any polypeptide having at least 65%, such as at least 70%, such as at least 75%, such as at least 80%, such as at least 85%, such at least 90%, such as at least 95%, such as at least 97%, such as at least 99%, sequence identity to any one of SEQ ID NOs: 2, 3, or 4 may also be a parent polypeptide, such as a parent alpha-amylase, for the variants of the present invention.

The parent alpha-amylase may be a fusion polypeptide or cleavable fusion polypeptide. Such fusion polypeptide may consist of a subsequence of one parent polypeptide and a subsequence of second parent polypeptide. In particular, a fusion polypeptide may consist of an A and B domain of one species of alpha-amylase and a C domain of another species of alpha-amylase, and thereby providing a parent polypeptide to generate a variant of the present invention. Techniques for producing fusion polypeptides are known in the art, and include ligating the coding sequences encoding the polypeptides so that they are in frame and that expression of the fusion polypeptide is under control of the same promoter (s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

The terms "A domain", "B domain" and "C domain" as used herein, refers to three distinct domains A, B and C, all part of the alpha-amylase structure, see, e.g., Machius et al., 1995, *J. Mol. Biol.* 246: 545-559. Thus, an alpha-amylase, such as a parent polypeptide and a variant according to the invention, may comprise both an A, B, and C domain. The term "domain" means a region of a polypeptide that in itself forms a distinct and independent substructure of the whole molecule. Alpha-amylases consist of a beta/alpha-8 barrel harboring the active site residues, which is denoted the A domain, a rather long loop between the beta-sheet 3 and alpha-helix 3, which is denoted the B domain (together; "A and B domain"), and a C-domain and in some cases also a carbohydrate binding domain (e.g., WO 2005/001064; Machius et al., supra).

The domains of an alpha-amylase may be determined by structure analysis such as using crystallographically techniques. An alternative method for determining the domains of an alpha-amylase is by sequence alignment of the amino acid sequence of the alpha-amylase with another alpha-amylase for which the domains have been determined. The sequence that aligns with, e.g., the C-domain sequence in the alpha-amylase for which the C-domain has been determined can be considered the C domain for the given alpha-amylase.

The term "A and B domain" as used herein, refers to two domains of an alpha-amylase taken as one unit, whereas the C domain is another unit of the alpha-amylases. Thus, the amino acid sequence of the "A and B domain" is understood as one sequence or one part of a sequence of an alpha-amylase comprising an "A and B domain" and other domains (such as the C domain). In one embodiment, the A and B domain of a parent alpha-amylase correspond to amino acids 1 to 397 of the amino acid sequence as set forth in SEQ ID NO: 3.

The term "C domain" as used herein, refers to a domain of an alpha-amylase as one unit. The "C domain" of an alpha-amylase corresponds to amino acids 400 to 485 of SEQ ID NO: 3.

A fusion polypeptide may further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent polypeptide may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent polypeptide may then be obtained by similarly screening a genomic DNA or cDNA library of another microorganism or mixed DNA sample. Once a polynucleotide encoding a parent polypeptide has been detected with the probe(s), the polynucleotide can be isolated or cloned by utilizing techniques that are known to those of ordinary skill in the art (see, e.g., Sambrook et al., 1989, supra).

In one embodiment, the parent alpha-amylase comprises or consists of the amino acid sequence set forth in SEQ ID NOs: 3, or 4. In another embodiment, the parent alpha-amylase comprises or consists of the mature polypeptide of SEQ ID NO: 2. In particular, the parent alpha-amylase may comprise or consist of amino acids 1 to 485 of SEQ ID NO: 2.

In another embodiment, the parent alpha-amylase is a fragment of the amino acid sequence as set forth in SEQ ID NO: 3 containing at least 350, such as at least 390 amino acid residues, e.g., at least 395 and at least 397 amino acid residues of SEQ ID NO: 3.

In another embodiment, the parent alpha-amylase is an allelic variant of the mature polypeptide of SEQ ID NO: 3.

The term "sequence identity" as used herein, refers to the relatedness between two amino acid sequences or between two nucleotide sequences. For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$\text{(Identical Residues} \times 100)/\text{(Length of Alignment} - \text{Total Number of Gaps in Alignment)}$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$\text{(Identical Deoxyribonucleotides} \times 100)/$$
$$\text{(Length of Alignment} - \text{Total Number of Gaps in Alignment)}$$

The term "fusion polypeptide" as used herein, refers to a polypeptide which comprises amino acid sequences originating from more than one, such as two, three, or four, species. Such a fusion polypeptide may have been generated by molecular techniques well-known to the skilled person. A fusion polypeptide of the present invention has alpha-amylase activity. In particular, a fusion polypeptide of the present invention, comprises e.g. an A and B domain of one alpha-amylase and a C domain from another alpha-amylase.

The term "mature polypeptide" and "mature amino acid sequence" as used herein, refers to a polypeptide in its final form following translation and any post-translational modifications, such as N-terminal processing, C-terminal truncation, glycosylation, phosphorylation, etc. Also contemplated within the term "mature polypeptide" is that the signal peptide of the polypeptide has been cleaved off e.g. during a naturel maturation process within the cell expressing the polypeptide. In one aspect, the mature polypeptide is the amino acid sequence of SEQ ID NO:3. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one embodiment, a mature polypeptide comprise up to 485 amino acid residues (e.g., amino acids 1 to 485 of SEQ ID NO: 2). Thus, in one embodiment, the mature polypeptide comprise up to 486 amino acid residues corresponding to the amino acid sequence set forth in SEQ ID NO:3.

The term "Improvement Factor" as used herein, refers to a quantitative way of calculating the improvement of a particular property of a variant according to the present invention. Determination of the Improvement Factor may be according to the following formula:

$$\frac{\text{Intensity value of variant} - \text{Intensity value of blank}}{\text{Intensity value of parent} - \text{Intensity value of blank}}$$

Other formulas may be used to determine the Improvement Factor. The skilled person knows the presently presented formula as well as alternative ways of calculating the Improvement Factor.

According to the present invention, a value of 1.0 corresponds to the specific activity observed for the parent alpha-amylase. A value above 1.0 indicates an improvement of specific activity of the variant tested compared to the parent alpha-amylase. Accordingly, any value of ≥1.0 is indicative for improvement of property, such as specific activity, of the variant compared to the parent alpha-amylase.

Similarly, the term Improvement Factor may be used when measuring stability, such as thermostability, in a detergent composition of a variant. Thus, the term Improvement Factor may also be used as an indicator for stability of a variant. According to the present invention, a value of 1.0 correspond to the stability observed for the parent alpha-amylase. A value above 1.0 indicates an improvement of stability of the variant tested compared to the parent alpha-amylase. Accordingly, any value of ≥1.0 is indicative for improvement in stability of the variant compared to the parent alpha-amylase.

The term "measure of stability" as used herein, refers to a measure of enzymatic stability. Such measures of stability include stability in detergents, chelator stability, pH stability, towards protease, chloride, and/or bleach, and thermostability.

The term "stability" as used herein, refers to a the residual activity of a given variant which may be determined by incubating the variant in a model detergent composition preferably comprising chelating agents such as EDTA, EGTA, DTPA, DTMPA, MGDA or HEDP. Thus, the residual activity is in particular relating to "chelator stability", i.e. the variant has been shown to have a given residual activity post incubation in a model detergent comprising a chelator. For example, as shown in the Example section, a variant may be tested in the a Model A detergent composition comprising EDTA in a final concentration of 0.1%. The residual activity may then be determined after a given period of incubation time at a given temperature. E.g. by using EnzCheck or Phadebas assays described in the Example section, the residual activity can be determined. Activity of the tested variant after the given time and temperature may be compared to the activity of reference incubated at low temperature, such as 4° C. and 0° C., for the same time period in the same detergent composition. The lesser the difference between both treatments, the higher is the detergent stability. Similar tests may be done using other detergents containing chelators, such as DTMPA, sodium citrate and HEDP. Similarly, surfactant stability may be determined in a similar manner. Thus, the variant of the present invention may preferably have an improved stability towards surfactants, such as anion surfactants and LAS, wherein the surfactant stability may be determined by the same assay as described above.

The term "improved storage stability" as used herein, refers to the stability of a given variant compared to the parent polypeptide, wherein residual activity is measured upon storage for a given time and temperature. Thus, the stability of a variant under storage conditions is improved when compared to a reference, such as a parent polypeptide.

In one embodiment, the variant has an improved thermostability.

The term "improved thermostability" as used herein, refers to the improved stability of a given variant compared to the parent polypeptide wherein the stability has been determined after incubation at a raised temperature for a given time period. E.g. a raised temperature may be such as 50° C. or more.

In one embodiment, the improved stability is determined by a method comprising the steps of:

a) incubating an alpha-amylase variant sample and a parent alpha-amylase sample, respectively, in a model detergent composition, such as Model A, Model J, Model T, or Model X, for a period of time;

b) measuring the activity of the variant alpha-amylase and the parent polypeptide, respectively; and c) calculating the residual activity of the samples.

If the stability is determined in a model powder detergent, such as Model T or Model X, the stability may preferably be measured by incubation in a wash solution of said model powder detergent, e.g. the powder is dissolved in water wherein said variant is incubated.

In a further embodiment, the improved stability is determined by a method comprising the steps of:

a) incubating an alpha-amylase variant sample and a parent polypeptide sample, respectively, in a model detergent composition, such as Model A, Model J, Model T, or Model X, at 40° C. to 60° C. for 2 to 168 hrs;

b) measuring the activity of the variant alpha-amylase and the parent polypeptide, respectively; and c) calculating the residual activity of the samples as the average of activity in the samples relative to the average of the activity to frozen control samples.

The term "measure of specific activity" as used herein, refers to a measure of enzymatic activity. Such measures of activity include wash performance at pH 8.0 at 25° C. and activity using a synthetic substrate, such as Phadebas tables (Magle Life Sciences).

The term "specific activity" as used herein, refers to the number of moles of substrate converted to product by an enzyme preparation per unit time under specific conditions. Specific activity is expressed as units (U)/mg of protein. Specific activity may be determined as described in the Example 2.

The term "wash performance" as used herein, refers to an enzyme's ability to remove starch or starch-containing stains present on the object to be cleaned during e.g. laundry or hard surface cleaning, such as dish wash. The term "wash performance" includes cleaning in general e.g. hard surface cleaning as in dish wash, but also wash performance on textiles such as laundry, and also industrial and institutional cleaning. The wash performance may be quantified by calculating the so-called Intensity value, and results may be displayed as "Improvement Factor" (IF). Wash performance may be determined as in described in the Examples herein.

The term "Intensity value" as used herein, refers to the wash performance measured as the brightness expressed as the intensity of the light reflected from the sample when illuminated with white light. When the sample is stained the intensity of the reflected light is lower, than that of a clean sample. Therefore the intensity of the reflected light can be used to measure wash performance, where a higher intensity value correlates with higher wash performance.

Color measurements are made with a professional flatbed scanner (Kodak iQsmart, Kodak) used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int = \sqrt{r^2 + g^2 + b^2}$$

The term "improved wash performance" as used herein, refers to an improvement of the wash performance of an alpha-amylase of the present invention relative to the wash performance of the parent polypeptide. Improved wash performance may be measured by comparing of the so-called Intensity value and calculating the Improvement Factor (IF). The improved wash performance is determined according to the section "Wash performance of alpha-amylases using Automatic Mechanical Stress Assay" and using model detergent J at 15° C. Other model detergents may be used, such as Model detergent A, Model detergent X or Model detergent T.

Thus, in one embodiment, the improved wash performance is determined by a method comprising the steps of:

a) washing a fabric stained with starch with an alpha-amylase variant and a parent polypeptide sample added, respectively, to a model detergent composition, such as Model A, Model J, Model T, or Model X;

b) measuring the intensity of light reflected from the sample when illuminated with white light; and c) optionally, calculating the improvement factor (IF) as the ration of delta intensity of the alpha-amylase sample over the delta intensity of the parent polypeptide sample.

In one embodiment, the improved wash performance is determined by a method comprising the steps of:

a) washing a fabric stained with starch with an alpha-amylase variant and a parent polypeptide sample added, respectively, to a model detergent composition, such as Model A, Model J, Model T, or Model X, for 20 minutes at 15° C. and 30° C.;

b) measuring the intensity of light reflected from the sample when illuminated with white light; and c) optionally, calculating the improvement factor (IF) as the ration of delta intensity of the alpha-amylase sample over the delta intensity of the parent polypeptide sample.

Figure 2:
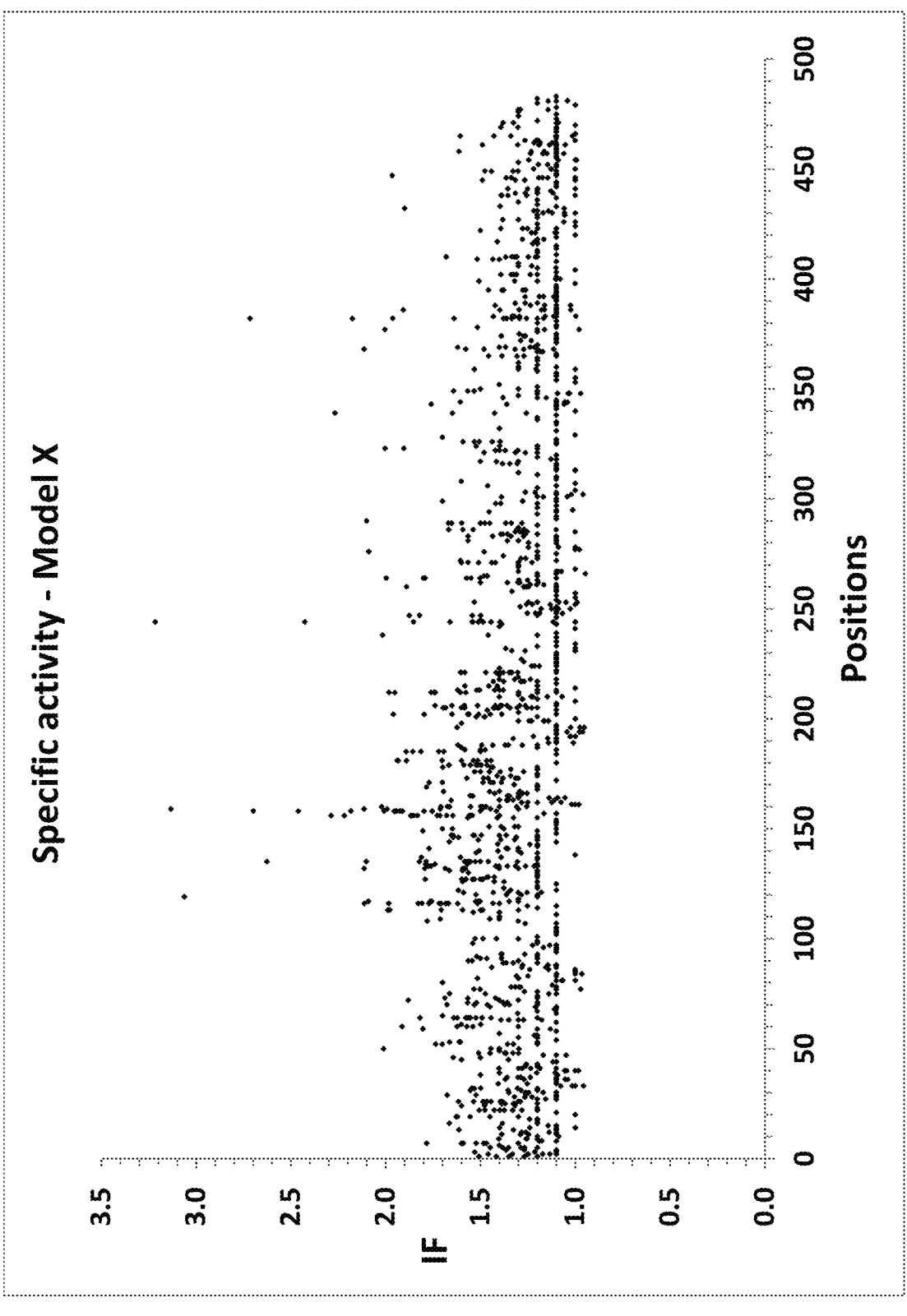
FIG. 2 shows the Improvement Factor (IF) for a measure of specific activity of variants according to the present invention tested in a Model X detergent. The individual position modified is given as the X axis and the specific IF for each variant is given on the Y axis.
Figure 3:
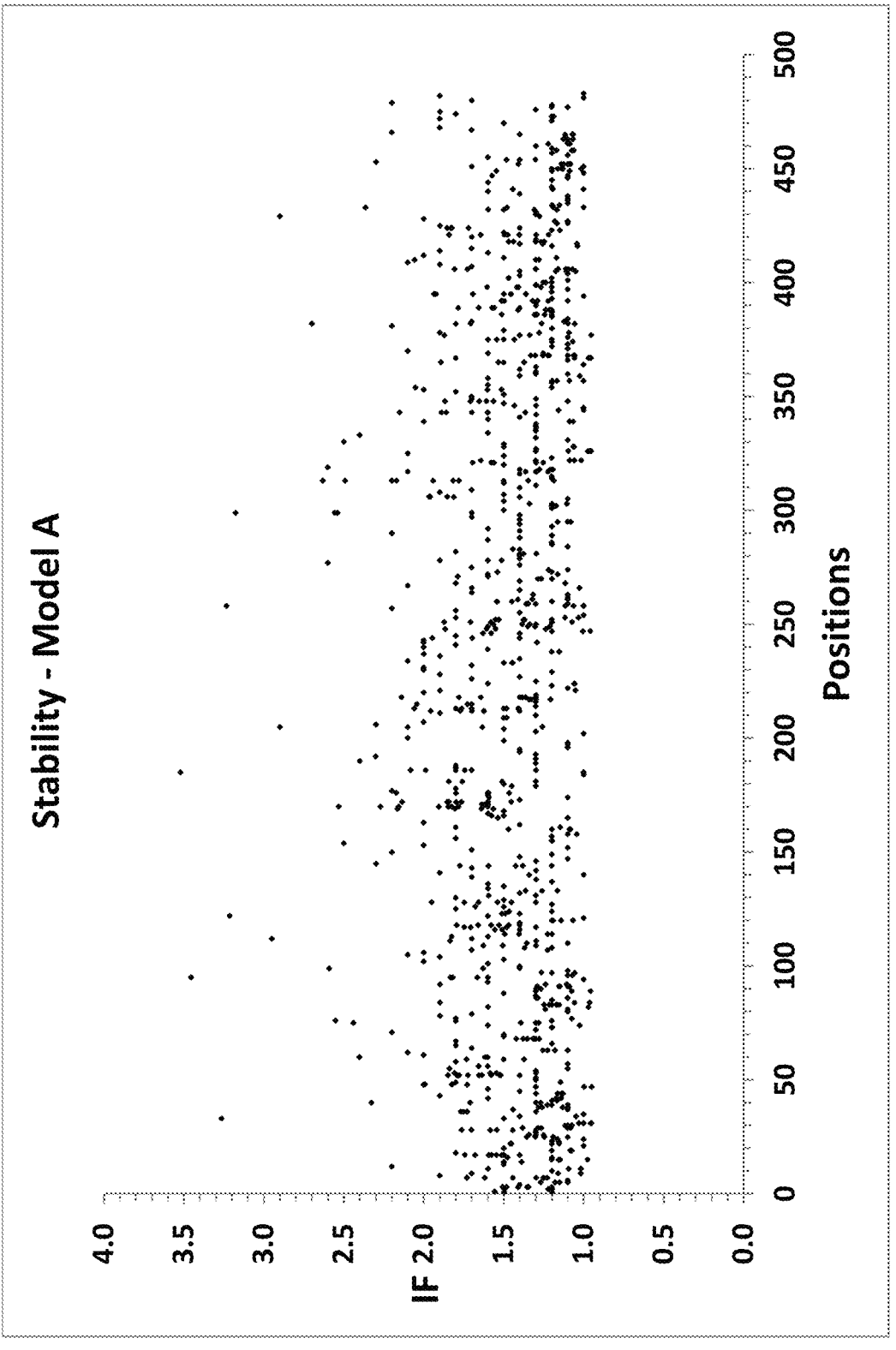
FIG. 3 shows the Improvement Factor (IF) for a measure of stability of variants according to the present invention tested in a Model A detergent. The individual position modified is given as the X axis and the specific IF for each variant is given on the Y axis.

As can be seen from the data obtained in Example 4 and FIG. 1-3, a mean hit value for each tested position show that many variants having a modification in one of the positions have an IF of at least 1.0 for at least one of the tested conditions, i.e. specific activity in Model A or Model X, or stability.

The term "mean hit value" as used herein, refers to a mean value of the Improvement Factor measured for all the generated specific variants having an IF of more than 1.0 for each of the tested conditions, i.e. specific activity tested in Model A or Model X detergent compositions or the stability of the variants. Thus, the Improvement Factors for each individual variant in a particular position have been added up and divided by the number of variants for the particular position, and thereby providing the mean hit value.

In one embodiment, the variant comprises one or more of the substitutions selected from the group consisting of; H1A, H1G, H1V, H1C, H1S, H1L, H2T, H2G, H2L, H2M, H2E, H2P, D3A, D3C, D3R, D3Y, D3W, D3S, D3F, G4D, G4Q, G4R, T5L, T5Q, T5E, T5V, T5G, T5F, T5W, G7F, G7E, G7V, G7D, G7R, G7A, G7L, G7S, G7N, T8A, T8S, I9C, I9M, I9L, M10L, Q11C, Q11L, Q11V, Q11M, Y12V, Y12A, Y12F, F13I, F13Y, E14M, E14L, E14S, E14Q, E14F W15G, W15F, W15S, W15I, W15H, N16G, N16Q, N16R, V17Q, V17A, V17T, V17L, V17D, V17G, V17E, P18L, N19G, N19S, N19Y, N19T, N19V, D20R, Q22C, Q22A, Q22N, Q22S, Q22M, Q22T, Q22E, Q22Y, H23W, W24H, W24F, N25V, N25G, N25E, N25E, N25S, N25R, N25L, N25T, R26L, R26G, R26D, R26I, R26S, R26W, R26A, R26F, R26M, R26E, L27A, L27M, H28E, H28A, H28W, H28K, H28I, H28R, H28M, N29G, N29C, N29L, N29K, N29V, N29W, N29A, N30S, N30H, N30L, N30T, N30E, N30R, A31S, A31W, A31V, A31G, A31R, Q32G, Q32L, Q32A, Q32D, N33F, N33A, N33R, N33D, L34Y, L34F, K35L, K35E, K35W, K35Q, N36R, N36V, N36Q, N36A, N36P, N36W, N36E, N36T, A37R, A37T, A37S, A37G, A37E, G38N, G38M, G38Y, G38K, I39L, I39M, I39V, T40D, T40A, T40Q, T40E, T40S, A41Q, A41E, A41N, A41M, A41 D, I42A, I42V, I42L, W43R, I44T, I44L, I44V, P45A, P46G, A47S, A47G, A47T, W48C, W48I, W48L, W48G, W48M, W48P, W48Q, W48H, W48A, W48Y, W48F, K49Q, G50S, G50N, G50P, T51S, T51G, T51C, T51P, T51L, T51A, S52V, S52M, S52I, S52L, S52A, S52D, S52K, S52N, S52E, S52T, S52C, S52F, Q53L, Q53V, Q53G, Q53M, N54G, N54K, N54V, N54T, N54L, N54I, N54S, D55G, D55V, D55I, V56L, V56M, V56T, G59E, G59A, G59S, A60S, A60W, A60L, A60G, A60V, A60F, A60T, Y61F, L63P, L63I, L63V, L63H, L63K, L63C, L63G, L63A, Y64W, Y64S, Y64V, Y64I, Y64H, Y64M, Y64C, Y64R, Y64G, Y64L, Y64A, L66M, E68D, E68S, E68M, E68C, E68T, E68V, E68Q, E68Y, F69H, F69W, N70G, N70A, N70T, N70S, N70E, Q71E, Q71N, Q71D, Q71I, Q71V, K72Y, K72R, G73V, G73L, G73E, G73C, T74L, T74V, T74N, V75T, V75G, V75E, R76S, R76G, R76A, R76V, T77A, T77S, T77V, K78L, K78T, K78A, T81W, T81L, T81G, K82A, K82G, A83G, A83E, A83Q, A83R, A83S, A83F, A83V, E84F, E84D, E84M, E84W, L85V, E86L, E86D, E86W, E86R, R87M, R87A, R87E, A88S, A88G, A88V, I89A, I89P, I89H, I89L, R90L, R90G, S91A, S91G, S91E, S91V, S91T, L92C, L92F, K93W, K93G, K93L, N95G, N95E, N95L, N95S, N95W, N95C, N95D, N95R, G96Q, G96R, I97M, I97V, I97L, Q98V, Q98L, Q98C, Q98M, Q98T, Q98F, Q98W, Q98P, Q98H, V99I, V99L, V99S, V99T, V99G, V99E, Y100W, Y100V, Y100F, V103G, V103A, V103S, V103T, H107Q, H107M, K108V, G109A, G109S, G109F, G109D, G110C, A111S, D112E, D112K, D112V, D112F, D112C, F113M, F113V, F113E, F113L, F113C, F113D, F113K, F113Q, F133Y, T114S, T114V, T114L, E115C, E115A, R116Q, R116N, R116L, R116I, R116D, R116T, R116G, R116E, R116S, R116C, R116V, R116F, R116K, R116H, R116W, V117G, V117C, V117S, V117W, V117A, V117E, V117L, V117I, V117M, Q118E, I18F, Q118R, Q118V, Q118G, A119Y, A119W, V120I, V120D, V120L, V120C, V120A, V120N, E121V, E121M, E121D, E121P, E121G, V122E, V122P, V122L, V122I, V122F, N123G, N123A, N123E, N123W, N123T, N123P, N123K, N123V, P124R, P124G, Q125E, Q125T, N126G, N126A, N126E, N126T, N126R, R127G, R127S, R127C, R127W, R127L, R127V, R127F, R127Y, N128S, N128E, N128C, N128A, N128P, N128G, Q129L, Q129E, Q129C, E130C, V131L, V131E, V131I, S132A, S132H, S132P, S132C, S132E, S132D, S132V, S132Q, S132N, G133T, G133L, G133A, G133D, G133S, G133V, G133I, G133E, G133R, T134V, T134D, T134E, Y135L, Y135V, Y135S, Y135R, Y135T, Y135W, Y135K, Y135G, Y135P, Y135M, Y135D, Y135H, Y135F, Y135E, Q136E, Q136W, Q136G, I137A, I137S, I137G, I137V, E138A, E138L, E138Y, E138T, A139S, A139M, A139G, A139V, A139T, A139P, W140H, W140Y, W140S, W140A, T141C, T141G, T141S, T141M, G142D, G142E, G142A, G142R, F143M, F143L, F143I, N144C, N144G, N144R, N144M, N144K, F145A, F145C, F145S, F145N, F145Q, F145T, F145H, P146L, P146S, P146V, P146C, P146M, P146T, G147V, G147P, G147D, G147S, G147I, G147L, G147C, G149C, G149Y, G149L, G149A, N150C, N150D, N150E, Q151L, Q151T, Q151C, Q151I, S153C, S153G, S153T, S154M, S154E, S154A, S154V, F155T, F155H, F155L, F155W, K156Q, K156F, K156L, K156S, K156G, K156Y, K156V, K156A, K156D, K156W, K156P, K156E, K156C, K156N, K156T, W157L, R158S, R158M, R158A, R158G, R158Q, R158W, R158L, R158T, R158V, R158E, R158Y, W159N, W159G, W159T, W159C, W159E, W159D, W159S, W159H, Y160M, Y160A, Y160Q, Y160T, Y160S, Y160V, Y160G, Y160I, Y160L, Y160E, Y160W, Y160R, Y160H, H161N, H161C, F162M, F162L, F162Y, F162I, D163A, D163R, D163S, D163K, D163L, G164S, G164T, G164C, T165L, T165S, T165I, T165M, T165G, T165V, T165E, D166S, D166T, D166N, W167G, W167Y, W167D, W167F, D168M, D168S, D168G, Q169L, Q169A, Q169S, Q169V, Q169F, Q169E, S170A, S170V, S170Q, S170W, S170G, S170F, S170T, S170L, R171A, R171F, R171S, R171K, R171V, R171M, Q172E, Q172L, Q172S, Q172R, Q172G, Q172W, Q172C, L172K, L173I, L173G, I73N, L173M, L173S, L173Y, L173V, L173A, L174F, A174V, A174G, A174K, A174L, A174M, A174S, N175G, N175L, N175V, N175I, N175S, R176W, R176E, R176G, R176M, R176M, R176T, R176K, R176Y, I177L, I177S, I177G, Y178V, Y178R, Y178K, Y178W, K179L, K179C, K179E, K179S, K179W, K179A, K179G, K179T, K179F, F180A, F180L, R181A, R181G, R181K, R181P, R181S, R181V, R181Q, R181E, R181D, G184L, G184R, G184V, G184T, G184D, K185G, K185A, K185D, K185N, K185V, A186S, A186D, A186C, A186T, A186Q, A186V, A186N, A186E, A186H, W187G, D188R, D188Q, D188G, D188M, D188L, D188V, W189R, W189A, W189G, W189C, E190D, E190N, E190A, V191M, V191A, D192E, D192Q, D192S, T193K, T193V, T193C, T193P, T193S, T193G, T193D, T193R, E194S, E194D, E194L, E194Q, N195R, N195A, N195F, N195T, G196A, G196V, G196P, N197G, N197V, N197Y, N197C, N197D, Y198W, Y198A, Y198G, D199G, D199S, D199A, Y200W, Y200F, Y200C, Y200V, Y200T, Y200L, Y200A, Y200G, Y200S, M202T, M202L, Y203L, Y203W, Y203F, Y203G, Y203C, Y203I, Y203Q, Y203H, Y203T, Y203M, Y203V, Y203S, A204P, A204C, A204R, A204H, A204W, A204F, A204L, A204Y, A204D, A204G, D205C, D205A, D205L, D205R, V206H, V206Q, V206P, V206A, V206S, V206K, V206L, V206I, V206M, V206F, V206Y, M208R, M208P, M208L, M208C, D209C, D209E, D209H, D209F, D209Y, D209S, D209M, D209V, D209L, D209I, D209Q, H210V, H210F, H210A, H210W, H210L, H210G, H210D, H210E, H210Q, H210N, P211G, P211W, P211C, E212G, E212I, E212F, E212M, E212D, E212K, E212Y, E212R, E212C, V213M, V213T, V213G, V213C, V213W, V213R, V213F, I214P, I214V, N215C, N215D, N215V, N215T, L217V, L217S, L217T, L217G, L217C, L217P, L217A, L217W, N218S, N218D, N218R, N218L, N218M, R219L, R219W, R219S, R219A, R219H, R219I, R219M, R219T, R219E, R219Y, R219D, R219C, W220I, W220P, W220E, W220R, W220A, W220S, W220L, G221S, G221A, V222F, V222C, V222E, V222L, W223Y, W223F, W223L, Y224L, A225K, N226C, N226Q, N226M, N226E, N226K, N226R, T227S, T227M, T227C, T227L, T227Y, T227R, L228A, L228F, L228M, N229T, N229S, L230S, L230A, L230T, L230V, D231E, D231C, D231G, D231P, F233A, F233L, F233T, F233P, F233M, V238C, V238W, V238A, H240W, I241L, K242A, K242C, K242Y, K242P, K242W, K242G, K242L, K242R, K242S, K242E, K242Q, K242H, S244Q, F245G, F245C, F245V, F245D, F245A, M246L, M246F, M246V, M246I, R247Y, R247G, R247M, D248G, D248R, W249L, W249F, L250W, L250T, L250A, L250C, L250Y, L250F, G251K, G251M, G251Q, H252E, H252W, H252C, H252V, H252T, H252F, V253S, V253W, V253A, V253L, R254Q, R254S, G255C, G255E, G255L, Q256P, T257V, G258V, G258C, G258I, G258P, G258L, G258D, G258F, K259V, K259Q, K259I, K259L, K259A, K259S, K259D, K259C, N260E, N260C, N260W, N260D, N260S, N260R, N260G, L261G, L261D, L261T, F262Q, F262L, F262E, F262R, F262P, F262V, A263L, A263C, V264T, V264L, Y267V, Y267L, W268V, W268Y, K269W, K269L, K269Q, K269R, N270D, N270A, N270M, N270G, D271E, D271V, D271C, L272M, G273W, G273R, G273V, G273E, A274S, A274D, A274E, L275G, L275E, L275A, L275R, L275K, E276R, E276L, N277D, Y278G, Y278S, L279V, L279Q, L279G, L279M, S280C, S280R, S280E, S280D, K281L, K281A, K281W, K281G, T282G, T282A, T282C, T282R, T282I, N283G, N283E, N283Q, N283V, N283A, W284T, W284I, W284S, W284E, W284C, W284V, W284A, T285E, T285F, T285S, T285P, T285W, T285M, M286D, M286L, M286C, S287T, S287E, S287V, S287Q, S287P, S287L, S287W, S287C, A288L, A288Y, A288V, V291T, P292A, P292Q, P292L, P292R, P292G, L293A, L293E, L293T, L293G, L293Q, L293Y, H294G, H294A, H294W, H294Q, H294S, Y295H, Y295S, Y295I, Y295A, N296A, N296Y, N296M, N296F, N296H, N296S, N296K, L297S, L297W, L297H, Y298V, Y298P, Q299S, Q299L, Q299R, Q299I, Q299P, Q299A, Q299H, A300V, A300C, S301A, S301R, S301Q, N302I, N302T, N302M, N302S, S303I, S303E, S303A, S303M, S304I, S304P, S304G, S304L, S304F, S304A, S304M, G305S, G305V, G305L, G305F, G305I, G305Q, N306V, N306L, N306D, N306S, N306T, Y307F, Y307W, M309L, R310A, R310T, N311C, N311Y, N311L, N311R, L312F, L312V, L312I, L313S, L313M, L313I, N314Y, N314D, N314F, G315V, G315I, G315T, G315R, G315F, T316K, T316S, T316C, T316G, V318C, V318E, V318L, V318A, Q319L, Q319I, Q319A, Q319H, Q319D, Q319F, Q319P, R320C, R320V, R320L, R320A, R320S, H321T, H321E, H321V, H321C, H321S, H321G, H321R, P322E, P322C, S323N, A325V, A325S, V326I, V326G, V326A, V326C, V326T, T327S, T327L, T327V, T327E, T327Q, F328M, F328C, V329A, 329S, V329C, V329I, N331C, N331V, N331I, T334S, T334A, P336M, P336E, P336D, P336R, P336L, P336S, P336K, P336W, G337T, G337V, G337C, G337M, G337F, E338A, E338H, E338T, E341C, E341D, E341I, E341M, E341F, E341K, E341S, E341P, E341T S342G, S342T, S342A, V344S, V344L, Q345K, Q345V, Q345I, Q345L, Q345C, Q345W, Q345N, G346H, G346A, G346L, G346N, G346R, G346Q, G346V, G346S, W347L, W347R, W347V, W347C, F348Q, F348S, F348C, F348P, F348M, K349G, K349A, K349Y, K349L, K349S, P350S, P350Q, P350L, P350G, P350D, P350E, L351W, L351M, L351S, L351Q, L351H, A352S, A352C, A354C, T355V, T355A, T355L, T355Y, T355F, L357C, L357S, L357T, L357H, T358V, T358F, T358S, T358L, E360S, E360D, E360C, E360G, E360A, E360M, Q361P, Q361R, Q361V, Q361A, Q361E, Q361G, Q361D, Q361S, G362Y, G362R, G362C, G362N, G362M, G362V, Y363Q, Y363L, Y363I, Y363A, Y363V, Y363R, Q365D, Q365M, Q365L, Q365T, Q365C, Q365S, V366L, V366A, V366I, V366C, F367L, F367S, F367A, Y368M, Y368T, Y368H, Y368A, Y368S, Y368Q, Y368I, Y368L, Y368V, G369K, G369S, G369E, G369A, G369R, G369I, G369L, D370A, D370T, Y372A, Y372S, Y372I, Y372L, Y372G, G373C, G373S, G373R, G373T, G373Q, G373W, I374Y, I374L, I374S, I374M, P375L, P375A, P375T, P375V, P375R, P375E, P375S, S376A, S376N, S376P, S376W, S376R, S376L, S376E, S376T, S376V, S376I, S376Q, S376F, D377C, D377L, D377V, D377T, D377S, D377G, V379L, V379F, V379P, V379S, P380L, P380E, P380A, P380V, P380G, P380I, P380Y, S381N, S381L, S381A, S381I, S381V, Y382I Y382A, Y382E, Y382L, Y382V, Y382R, Y382K, R383G, R383S, R383P, R383V, Q384A, Q384P, Q384L, Q384H, Q384R, Q384Y, Q384S, Q384V, Q384T, Q384G, Q384E, I386T, I386L, I386M, I386W, I386V, D387H, D387V, D387Q, D387L, P388G, P388T, P388M, P388V, P388B, P388K, P388L, P388S, P388R, L389S, L389H, L389A, L389V, L389F, L389M, L390S, L390F, L390I, L390G, L390V, L390T, L390N, L390H, L390C, K391L, K391Y, K391A, K391Q, A392I, A392M, A392T, Q394S, Q394R, Q394L, Q394T, Q394N, Q394M, Q395W, Q395N, Q395L, Q395E, Q395K, Q395R, Q395V, Q395S, Q395M, Y396T, Y396L, Y396R, Y396W, A397C, A397G, A397S, Y398K, Y398S, Y398C, Y398N, R400L, R400C, R400K, R400S, R400M, R400E, R400I, H402V, H402E, H402M, H402A, H402Y, H402S, H402P, H402L, H402D, H402R, H402T, D403E, D403P, D403Q, D403I, Y404F, Y404W, Y404K, F405C, F405V, F405I, F405P, F405W, F405G, F405A, D406E, D406V, D406T, D406M, D406S, H407C, H407D, W408R, W408G, W408D, W408P, W408C, W408Y, D409G, V410I, V410Q, V410E, V410L, I411A, I411L, I411V, T414A, T414V, R415F, R415L, R415A, R415Q, E416C, E416V, E416L, E416A, E416Q, N418L, N418A, N418C, N418M, N418G, N418R, N418F, A419E, A419C, A419M, A419Q, A419G, A419V, A419L, A419R, S420E, S420T, S420V, S420M, H421V, H421C, H421A, H421R, H421T, P422Y, P422H, P422D, P422R, S424C, S424A, S424L, G425A G425V, L426S, L426A, A427V, A427S, T428L, T428N, T428A, T428G, I429V, I429A, M430R, M430L, M430A, M430T, S431A, S431T, S431F, D432Q, D432P, G435E, G435N, G435M, G435I, G435S, G436L, G436M, G436E, G436T, S437G, S437Q, S437L, K438T, W439C, W439H, W439E, W439A, W439R, W439T, W439N, W439T, W439R, W439N, M440L, Y441N, Y441H, Y441Q, Y441K, V442I, 444A, R444S, R444L, R444P, R444V, Q445L, Q445S, Q445C, Q445E, Q445R, K446Q, K446G, K446T, K446P, A447G, A447Q, A447E, A447T, A447R, A447S, G448S, G448R, V450A, V450T, V450Q, V450R, W451L, H452A, H452T, H452C, H452G, H452Y, H452R, H452V, D453E, M454R, M454L, M454V, M454Q, M454S, T455L, T455S, G456V, G456R, G456Y, G456K, G456L, N457V, N457I, N457G, N457R, S459E, S459V, S459C, S459P, S459M, S459T, S459Q, S459R, G460S, G460D, G460E, T463C, T463V, T463L, T463D, T463H, T463M, T463A, T463Q, I464V, N465G, N465Q, N465L, N465R, Q466L, Q466C, Q466E, D467V, D467C, W469T, W469M, W469E, W469N, H471Q, F473Y, F473C, F473R, F473E, F473G, F473T, F473V, N475T, N475H, N475G, G476F, G476Y, G476K, G477Q, G477F, G477K, G477L, V481Q, V481S, and W482F, wherein the numbering is according to the amino acid sequence set forth in SEQ ID NO: 3, and wherein the substitution at the one or more positions provides a variant having an IF of ≥1.0 for a measure of stability and/or an IF of ≥1.0 for a measure of specific activity.

The term "corresponding to" as used herein, refers to way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 3, or any other sequence listed herein, has been described elsewhere herein. Alternative alignment methods may be used, and are well-known for the skilled person.

In one embodiment, the parent alpha-amylase has at least 85%, such as at least 90%, such as at least 95%, such as 97%, such as at least 98%, sequence identity with the amino acid sequence set forth in SEQ ID NO: 3. In another embodiment, the parent alpha-amylase has at least 85%, such as at least 90%, such as at least 95%, such as 97%, such as at least 98%, sequence identity with the amino acid sequence set forth in SEQ ID NO: 4.

In one embodiment, the parent alpha-amylase consists of or comprises the amino acid sequence set forth in SEQ ID NOs: 3 or 4.

The present invention provides variants of such parent alpha-amylases.

Accordingly, the variants of the present invention comprise an amino acid sequence having at least 60%, such as at least 65%, such as at least 70%, such as at least 75%, such as at least 80%, such as at least 85%, such as at least 90%, such as at least 95%, such as at least 97%, such as at least 98%, such as at least 99%, but less than 100% sequence identity to the amino acid sequences set forth in SEQ ID NOs: 3 and 4.

The variants according to the present invention may comprise other modifications than a substitution, such as an insertion or a deletion. Such modifications may also be termed "alterations". Thus, the term "alteration" as used herein, refers to both substitutions and deletions of amino acid within the amino acid sequence of a polypeptide. The terms "alteration" and "modification" may be used interchangeably herein. This should not be understood as any limitation and thus, the terms constitute the same meaning and purpose unless explicitly stated otherwise.

In one embodiment, the variant comprises a substitution at one or more positions selected from the group consisting of; H1, H2, D3, G4, T5, G7, T8, I9, Q11, Y12, F13, E14, W15, N16, P18, N19, D20, Q22, W24, N25, R26, L27, H28, N29, N30, A31, Q32, L34, K35, N36, A37, I39, T40, A41, W43, I44, P45, P46, A47, W48, G50, T51, S52, Q53, N54, D55, V56, G59, A60, Y61, L63, Y64, L66, E68, F69, N70, Q71, K72, G73, T74, V75, R76, T77, K78, K82, A83, E84, L85, R87, A88, I89, R90, S91, L92, K93, N95, G96, I97, Q98, V99, Y100, V103, H107, K108, G109, D112, F113, E115, R116, V117, A119, V120, E121, V122, N123, Q125, N126, R127, N128, Q129, E130, V131, S132, G133, T134, Y135, I137, A139, W140, T141, G142, F143, N144, F145, P146, G147, G149, N150, Q151, S153, F155, K156, W157, R158, W159, Y160, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, R219, V222, W223, A225, N226, T227, L228, N229, L230, D231, F233, V238, I241, K242, F245, M246, W249, L250, H252, R254, G255, T257, G258, K259, N260, L261, F262, A263, Y267, W268, K269, N270, D271, G273, A274, Y278, L279, S280, K281, T282, N283, W284, T285, M286, S287, A288, V291, P292, L293, H294, N296, L297, Q299, A300, S301, S303, S304, G305, N306, L312, L313, N314, G315, T316, V318, Q319, R320, H321, P322, A325, P336, G337, E341, S342, V344, Q345, G346, W347, F348, K349, P350, L351, A352, L357, T358, Q361, G362, Y363, Q365, V366, Y368, G369, D370, Y372, G373, I374, P375, S376, D377, V379, P380, S381, Y382, R383, Q384, I386, D387, P388, L389, L390, K391, A392, Q394, Q395, Y396, A397, R400, H402, F405, D406, H407, W408, V410, T414, R415, E416, N418, A419, H421, G425, A427, T428, I429, M430, S431, G435, G436, S437, W439, M440, V442, R444, Q445, A447, G448, H452, M454, T455, G456, N457, S459, G460, T463, N465, D467, W469, H471, F473, N475, G477, and V481; wherein the positions correspond to amino acid positions in the amino acid sequence set forth in SEQ ID NO: 3, which one or more substitutions provides an improvement factor of ≥1.2 for a measure of specific activity in Model A detergent composition, and optionally, an improvement factor of ≥1.0 for a measure of stability.

In a particular embodiment, the variant comprises one or more of the substitutions selected from the group consisting of; H1V, H1G, H1S, H1C, H2T, H2L, H2M, H2E, H2P, H2G, D3A, G4Q, G4D, G4R, T5Q, T5G, T5E, T5V, G7F, G7V, G7E, G7E, G7D, G7R, T8S, I9M, I9L, Q11L, Q11V, Y12V, Y12A, Y12F, F13Y, F13I, E14L, E14M, E14S, W15G, W15S, W15F, N16G, N16Q, P18L, N19G, N19S, N19Y, N19T, N19V, D20R, Q22C, Q22A, Q22N, Q22S, Q22M, Q22T, Q22E, W24F, N25V, N25S, N25G, N25E, N25E, R26L, R26G, R26D, R26M, R26I, R26S, R26W, R26A, R26F, L27A, L27M, H28A, H28E, H28I, N29G, N29C, N29L N30S, N30H, N30L, N30T, N30E, A31S, A31V, Q32D, Q32G, Q32L, Q32A, L34F, L34Y, K35L, K35E, K35W, K35Q, N36R, N36Q, N36A, N36E, A37T, A37S, I39M, I39L, T40E, T40A, A41E, A41N, A41M, A41Q, A41D, W43R, I44T, P45A, P46G, W48G, W48L, W48C, W48I, W48M, W48P, W48Q, W48Y, W48F, G50P, G50S, G50N, T51S, T51G, T51P, T51L, T51C, S52M, S52V, S52I, S52L, Q53V, Q53L, Q53G, N54G, N54K, N54V, D55V, D55I, V56L, V56M, G59E, G59A, A60S, A60W, A60L, A60G, A60T, Y61F, L63V, L63P, L63I, L63H, L63K, Y64W, Y64S, Y64V, Y64I, Y64H, Y64M, Y64C, Y64R, Y64G, Y64L, Y64A, L66M, E68D, F69H, F69W, N70G, N70A, N70T, N70S, N70E, Q71N, Q71E, Q71D, Q71I, Q71V, K72Y, K72R, G73V, G73L, G73E, T74V, T74L, V75T, V75G, R76S, R76G, R76A, T77S, K78L, K78T, K78A, K82A, A83G, A83E, E84D, L85V, R87M, R87A, R87E, A88V, I89H, I89P, I89A, R90L, R90G, S91E, S91A, S91G, L92C, K93W, K93G, K93L, N95L N95W, N95C, N95E, N95S, N95G, G96Q, I97V, Q98C, Q98M Q98T, Q98V, Q98L, V99I, V99L, V99S, V99T, Y100V, Y100F, Y100W, V103G, H107Q, K108V, G109A, G109S, D112E, F113L, F113M, F113V, F113E, F113C, F113D, F113Y, E115A, R116N, R116L, R116I, R116D, R116T, R116G, R116E, R116S, R116C, R116V, R116Q, R116F, V117C, V117L, V117S, V117W, V117A, V117G, V117E, A119Y, V120D, V120L, E121P, E121G, E121V, E121M, E121D, V122E, V122P, V122I, N123G, N123A, N123E, N123W, N123T, N123P, Q125E, Q125T, N126E, N126G, N126A, R127G, R127S, R127C, R127W, R127L, R127V, R127F, R127Y, N128C, N128S, N128E, Q129L, Q129C, Q129E, E130C, V131L, V131E, S132A, S132H, S132P, S132C, S132E, S132D, S132N, G133S, G133T, G133L, G133V, G133I, G133E, G133A, G133D, T134V, T134D, T134E, Y135L, Y135V, Y135S, Y135R, Y135T, Y135W, Y135K, Y135G, Y135P, Y135M, Y135D, Y135H, Y135F, Y135E, I137A, I137S, I137G, A139M, A139S, W140Y, W140S, W140A W140H, T141M, T141S, T141C, T141G, G142D, G142E, F143M, F143L, N144C, F145C, F145S, F145A, P146S, P146V, P146C, P146L, G147V, G147P, G147D, G147S, G147I, G147L, G147C, G149C, N150C, N150D, N150E, Q151T, Q151C, Q151L, S153C, F155H, F155T, F155L, K156Y, K156V, K156A, K156D, K156W, K156P, K156E, K156C, K156F, K156Q, K156L, K156S, K156G, W157L, R158M, R158A, R158G, R158Q, R158W, R158L, R158T, R158V, R158E, R158Y, R158S, W159N, W159G, W159T, W159C, W159E, W159D, W159S, W159H, Y160Q, Y160M, Y160T, Y160A, Y160S, Y160V, Y160G, Y160I, Y160L, Y160E, F162M, F162L, F162Y, F162I, D163K, D163A, D163R, D163L, G164S, G164T, G164C, T165L, T165M, T165S, T165G, T165I, D166T, D166N, D166S, W167Y, W167G, W167D, D168M, D168S, D168G, Q169A, Q169L, Q169E, S170A, S170V, R171F, R171S, R171V, R171K, R171A, Q172S, Q172L, Q172E, L173G, L173N, L173M, L173S, L173Y, L173V, L173I, A174G, A174V, N175L, N175V, N175I, N175G, R176E, R176W, R176G, R176M, I177L, I177S, I177G, Y178V, Y178R, Y178K, K179C, K179E, K179S, K179W, K179A, K179G, K179T, K179F, K179L, F180A, F180L, R181K, R181P, R181S, R181V, R181Q, R181E, R181A, R181G, G184L, G184R, G184V, G184D, K185A, K185D, K185N, K185V, K185G, A186C, A186S, A186D, W187G, D188Q, D188G, D188R, D188M, D188L, D188V, W189R, W189A, W189G, W189C, E190D, E190N, E190A, V191M, V191A, D192Q, D192S, T193K, T193V, T193C, T193P, T193S, E194D, E194L, E194Q, N195R, N195A, G196A, G196V, N197G, N197V, N197Y, N197C, N197D, Y198W, D199G, D199S, D199A, Y200W, Y200F, Y200C, Y200V, Y200T, Y200L, Y200A, Y200G, Y200S, M202T, Y203F, Y203G, Y203C, Y203I, Y203Q, Y203H, Y203T, Y203M, Y203S, Y203V, Y203W, Y203L, A204P, A204R, A204C, A204H, A204W, A204F, A204L, A204Y, A204D, A204G, D205C, V206H, V206Q, V206P, M208C, D209E, D209H, D209F, D209Y, D209S, D209M, D209V, H210V, H210A, H210W, H210L, H210G, H210D, H210E, H210N, P211G, P211W, P211C, E212F, E212M, E212D, E212G, E212I, V213W, I214P, N215D, N215V, N215C, L217C, L217P, L217T, L217G, L217S, R219H, R219W, R219S, R219I, R219A, R219M, R219T, R219E, R219Y, R219D, R219C, R219L, V222F, V222C, V222E, W223Y, A225K, N226Q, N226C, T227S, T227M, T227C, T227L, L228A, L228F, N229S, L230S, L230A, L230T, L230V, D231G, F233A, F233L, V238C, V238W, I241L, K242C, K242Y, K242P, K242W, K242G, K242L, K242R, K242S, K242E, K242A, K242Q, F245C, F245V, F245D, F245G, M246L, M246F, W249L, L250T, L250A, H252E, H252W, H252C, R254Q, R254S, G255E, G255L, T257V, G258V, G258C, G258I, G258L, G258P, K259V, K259Q, K259I, K259L, N260E, N260D, N260C, N260W, L261G, L261D, F262Q, F262L, F262E, F262R, F262P, F262V, A263L, A263C, Y267V, Y267L, W268V, K269L, K269W, N270D, N270A, N270M, D271V, D271C, G273W, G273R, G273V, A274S, A274D, A274E, Y278G, Y278S, L279V, L279G, L279Q, S280C, K281L, K281W, K281G, K281A, T282R, T282I, N283V, N283A, W284E, W284C, W284V, W284A, T285E, T285F, T285S, M286D, M286L, S287V, S287Q, S287T, S287E, S287P, S287L, S287W, S287C, A288L, A288Y, V291T, P292A, P292Q, P292R, P292L, L293E, L293T, L293G, H294G, H294A, Y295F, Y295N, N296A, N296Y, N296M, N296F, L297S, L297W, Q299I Q299S, Q299L, Q299R, A300V, S301R, S301Q, S303I, S303E, S304P, G305S, N306V, L312F, L312V, L313S, N314F, N314D, G315I, G315V, T316S, V318C, V318E, V318A, V318L, Q319L, Q319I, Q319A, R320L, R320V, R320C, H321E, H321V, H321C, H321T, P322E, P322C, A325V, A325S, P336M, P336E, P336D, P336R, P336L, G337T, G337C, G337M, G337V, E341C, E341D, E341I, S342G, S342T, S342A, V344S, V344L, Q345K, Q345C, Q345V, Q345I, Q345L, G346H, G346A, G346L, G346N, G346Q, G346V, G346R, W347L, F348Q, F348S, F348C, K349G, K349A, K349Y, K349L, K349S, P350L, 350G, P350S, P350Q, L351M, L351S, A352S, A352C, L357C, L357T, L357S, T358V, T358F, T358S, Q361P, Q361R, Q361A, Q361E, Q361V, G362Y, G362R, G362C, G362N, G362M, G362V, Y363Q, Y363I, Y363A, Y363L, Q365D, V366A, Y368M, Y368T, Y368I, Y368L, Y368A, Y368S, Y368Q, Y368V, Y368H, G369K, G369S, G369A, G369E, G369R, G369I, D370A, D370T, Y372S, Y372I, Y372L, Y372G, G373C, G373S, I374Y, P375L, P375A, P375T, S376P, S376W, S376R, S376L, D377C, D377L, D377V, V379F, V379P, V379L, P380L, P380G, P380E, P380A, P380I, P380V, S381N, S381L, S381A, S381I, S381V, Y382I, Y382A, Y382E, Y382V, Y382L, R383G, R383S, R383P, Q384L, Q384H, Q384R, Q384Y, I386T, D387H, D387V, D387Q, D387L, P388G, P388T, P388M, P388W, P388V, L389S, L389H, L390I, L390G, K391Y, K391A, A392I, Q394S, Q394R, Q395N, Q395L, Q395E, Q395K, Q395R, Y396L, A397C, A397G, R400L, R400C, R400K, R400S, R400M, H402V, H402E, H402M, H402A, H402S, H402P, H402Y, H402L, F405C, F405V, F405I, F405P, F405W, F405G, D406E, H407C, H407D, W408R, W408P, W408C, W408Y, W408G, W408D, V410I, V410Q, T414V, T414A, R415F, R415L, E416C, E416V, N418L, N418A, N418C, N418M, N418G, A419E, A419C, A419M, H421V, H421C, H421A, H421R, G425A, A427V, T428G, I429V, I429A, M430R, S431A, G435E, G435N, G436M, G436E, G436L, G436T, S437Q, S437L, W439C, W439H, W439E, W439R, W439N, M440L, V442I, R444A, R444S, R444L, R444V, R444P, Q445L, Q445S, Q445C, Q445E, A447G, A447Q, A447E, A447T, G448S, H452A, H452T, M454R, M454L, M454V, T455S, G456V, G456R, G456Y, N457R, S459V, S459C, S459P, S459M, S459T, S459E, S459Q, G460S, G460D, G460E, T463D, T463H, N465Q, N465L, N465R, D467V, D467C, W469E, W469T, H471Q, F473Y, F473C, F473R, N475T, N475H, G476K, G477Q, G477F, G477K, G477L, V481Q, and V481S, wherein numbering is according to the amino acid sequence set forth in SEQ ID NO: 3, and wherein the one or more substitutions provides a variant having an IF≥1.2 for a measure of specific activity in Model A detergent composition, and optionally, an IF≥1.0 for measure of stability.

In one embodiment, the variant comprises one or more substitutions selected from the group consisting of; H1V, H2T, G7F, G7V, G7E, G7E, G7D, I9M, I9L, Q11L, Q11V, W15G, W15S, N19G, N19S, Q22C, Q22A, W24F, N25V, R26L, H28E, N29G, N30S, A31S, L34Y, K35L, I39L, T40A, A41Q, I44T, W48C, W48I, W48Y, W48F, S52M, S52V, Q53V, Q53L, V56L, G59E, T74V, T74L, V75T, I89A, R90L, S91A, S91G, L92C, N95E, N95S, N95G, I97V, Q98V, Q98L, Y100W, K108V, F113M, F113V, F113E, F113Y, R116Q, V117G, N126G, N126A, N128S, N128E, Q129E, G133A, G133D, A139M, W140H, T141S, T141C, T141G, F143M, F143L, F145A, P146L, Q151L, K156F, K156Q, K156L, K156S, K156G, R158S, T165I, D166S, Q169L, S170A, S170V, R171A, Q172L, Q172E, L173I, A174V, N175G, K179L, R181A, R181G, K185G, A186S, A186D, T193S, Y203W, Y203L, D209S, D209M, D209V, H210N, E212G, E212I, V213W, N215C, L217S, R219L, V222E, N226C, T227L, L228F, K242A, F245G, H252C, T257V, G258P, K259L, N260W, K269W, L279Q, K281A, M286L, P292L, L293T, L293G, Y295F, L297W, Q299S, Q299L, Q299R, N306V, L312F, L312V, G315V, T316S, V318L, R320V, R320C, H321T, P336L, G337V, S342A, V344L, Q345L, G346R, W347L, P350S, P350Q, Q361V, Y363L, Y368H, I374Y, S376R, S376L, V379L, P380V, S381V, S381N, D387Q, D387L, A392I, Q395E, Q395K, Q395R, H402L, F405G, T414A, E416V, N418M, N418G, A419M, S431A, G435N, W439E, W439R, W439N, G456Y, S459E, S459Q, N465L, N465R, and D467C, wherein numbering is according to the amino acid sequence set forth in SEQ ID NO: 3, and wherein the one or more substitutions provides a variant having an IF≥1.2 for a measure of specific activity in Model A detergent composition and an IF≥1.0 for a measure of stability.

In one embodiment, the variant comprises a substitution at one or more positions selected from the group consisting of; H1, H2, G4, T5, G7, Q11, F13, E14, W15, N16, P18, N19, D20, Q22, N25, R26, N29, N30, A31, Q32, L34, A41, P46, W48, G50, T51, S52, Q53, D55, V56, G59, A60, Y61, Y64, F69, N70, Q71, K72, G73, T74, V75, R76, T77, K78, K82, A83, R87, I89, R90, S91, L92, K93, N95, Q98, V99, Y100, H107, K108, G109, D112, F113, E115, R116, V117, A119, V120, E121, V122, N123, N126, R127, N128, Q129, E130, V131, S132, G133, T134, Y135, I137, A139, W140, T141, G142, F143, N144, F145, P146, G147, G149, N150, Q151, S153, F155, K156, W157, R158, W159, Y160, F162, D163, G164, T165, D166, W167, D168, Q169, S170, R171, Q172, L173, A174, N175, R176, I177, Y178, K179, F180, R181, G184, K185, A186, W187, D188, W189, V191, T193, E194, N197, D199, Y200, M202, Y203, A204, D205, V206, D209, H210, P211, E212, N215, L217, R219, W223, N226, V238, I241, K242, F245, G258, K259, N260, F262, A263, K269, N270, D271, G273, A274, Y278, L279, K281, W284, T285, S287, P292, N296, L297, Q299, S301, N306, L312, G315, V318, Q319, R320, H321, P322, A325, P336, G337, E341, S342, V344, G346, F348, K349, P350, L351, Q361, G362, Y363, Y368, G369, D370, Y372, G373, S376, D377, V379, P380, S381, S382, Q384, D387, Q394, Q395, A397, R400, H402, H407, W408, V410, R415, N418, H421, S431, G435, G436, W439, M440, Q445, A447, M454, G456, N465, D467, N475, G477, and V481; wherein the positions correspond to amino acid positions in the amino acid sequence set forth in SEQ ID NO: 3, which one or more substitutions provides an improvement factor of ≥1.4 for a measure of specific activity in Model A detergent composition, and optionally, an improvement factor of ≥1.0 for a measure of stability.

In a particular embodiment, the variant comprises one or more substitutions selected from the group consisting of; H1V, H1G, H1S, H1C, H2E, H2P, H2G, G4D, G4R, T5E, T5V, G7F, G7V, G7E, G7E, G7D, G7R, Q11V, F13Y, F13I, E14L, E14M, E14S, W15G, W15S, W15F, N16G, N16Q, P18L, N19G, N19S, N19Y, N19T, N19V, D20R, Q22C, Q22A, Q22S, Q22M, Q22T, Q22E, N25V, N25S, N25G, N25E, N25E, R26L, R26G, R26D, R26M, R26I, R26S, R26W, R26A, R26F, N29G, N29L, N30L, N30T, N30E, A31S, A31V, Q32D, Q32G, Q32L, Q32A, L34Y, A41Q, A41D, P46G, W48C, W48I, W48M, W48P, W48Q, W48Y, G50P, G50S, G50N, T51G, T51P, T51L, T51C, S52M, S52V, S52I, S52L, Q53V, Q53L, Q53G, D55V, D55I, V56L, V56M, G59E, G59A, A60S, A60W, A60L, A60G, A60T Y61F, Y64W, Y64S, Y64V, Y64I, Y64H, Y64M, Y64C, Y64R, Y64G, Y64L, Y64A, F69W, N70G, N70A, N70T, N70S, N70E, Q71N, Q71E, Q71D, Q71I, Q71V, K72Y, K72R, G73V, G73L, G73E, T74V, T74L, V75G, R76G, R76A, T77S, K78L, K78T, K78A, K82A, A83E, R87A, R87E, I89H, I89P, I89A, R90L, R90G, S91E, S91A, S91G, L92C, K93W, K93G, K93L, N95W, N95C, N95E, N95S, N95G, Q98C, Q98M, Q98T, Q98L, V99S, V99T, Y100V, Y100F, Y100W, H107Q, K108V, G109A, G109S, D112E, F113L, F113M, F113V, F113E, F113C, F113D, E115A, R116N, R116L, R116I, R116D, R116T, R116G, R116E, R116S, R116C, R116V, R116Q, R116F, V117C, V117L, V117S, V117W, V117A, V117G, V117E, A119Y, V120L, E121P, E121G, E121V, E121M, E121D, V122E, V122P, V122I, N123A, N123E, N123W, N123T, N123P, N126E, N126G, N126A, R127G, R127S, R127C, R127W, R127L, R127V, R127F, R127Y, N128C, N128S, N128E, Q129C, Q129E, E130C, V131L, V131E, S132A, S132H, S132P, S132C, S132E, S132D, G133V, G133I, G133E, G133A, G133D, T134V, T134D, T134E, Y135L, Y135V, Y135S, Y135R, Y135T, Y135W, Y135K, Y135G, Y135P, Y135M, Y135D, Y135E, I137A, I137S, I137G, A139M, A139S, W140Y, W140S, W140A, W140H, T141M, T141S, T141C, T141G, G142D, G142E, F143M, F143L, N144C, F145C, F145S, F145A, P146S, P146V, P146C, P146L, G147V, G147P, G147D, G147S, G147I, G147L, G147C, G149C, N150C, N150D, N150E, Q151T, Q151C, Q151L, S153C, F155H, F155T, F155L, K156Y, K156V, K156A, K156D, K156W, K156P, K156E, K156C, K156F, K156Q, K156L, K156S, K156G, W157L, R158M, R158A, R158G, R158Q, R158W, R158L, R158T, R158V, R158E, R158Y, R158S, W159N, W159G, W159T, W159C, W159E, W159D, Y160Q, Y160M, Y160T, Y160A, Y160S, Y160V, Y160G, Y160I, Y160L, Y160E, F162I, D163K, D163A, D163R, D163L, G164S, G164T, G164C, T165L, T165M, T165S, T165G, T165I, D166T, D166N, D166S, W167Y, W167G, W167D, D168G, Q169A, Q169L, S170A, S170V, R171F, R171S, R171K, R171V, R171A, Q172S, Q172E, L173G, L173N, L173M, L173S, L173Y, L173V, L173I, A174G, A174V, N175V, N175I, N175G, R176E, R176W, R176G, R176M, I177L, I177S, I177G, Y178V, Y178R, Y178K, K179C, K179E, K179S, K179W, K179A, K179G, K179T, K179F, K179L, F180L, R181K, R181P, R181S, R181V, R181Q, R181E, R181A, R181G, G184R, G184V, K185A, K185D, K185N, K185V, K185G, A186C, A186S, A186D, W187G, D188Q, D188G, D188R, D188M, D188L, D188V, W189R, W189A, W189G, W189C, V191M, V191A, T193C, T193P, E194Q, N197C, N197D, D199G, D199S, D199A, Y200W, Y200F, Y200C, Y200V, Y200T, Y200L, Y200A, Y200G, Y200S, M202T, Y203F, Y203G, Y203C, Y203I, Y203Q, Y203H, Y203T, Y203M, Y203S, Y203V, Y203W, Y203L, A204P, A204R, A204C, A204H, A204W, A204F, A204L, A204Y, A204D, A204G, D205C, V206P, D209V, H210V, H210A, H210W, H210L, H210G, H210D, H210E, P211C, E212M, E212D, E212I, N215D, N215V, N215C, L217P, L217T, L217G, L217S, R219H, R219W, R219S, R219I, R219A, R219M, R219T, R219E, R219Y, R219D, R219C, R219L, W223Y, N226Q, L230V, V238C, V238W, I241L, K242C, K242Y, K242P, K242W, K242G, K242L, K242R, K242S, K242E, K242A, K242Q, F245C, F245V, F245D, F245G, G258L, K259I, N260D, N260C, F262Q, F262L, F262E, F262R, F262P, F262V, A263L, A263C, K269L, K269W, N270D, N270A, N270M, D271C, G273V, A274S, A274D, A274E, Y278S, L279G, K281G, W284V, W284A, T285F, T285S, S287V, S287Q, S287T, S287E, S287P, S287L, S287W, S287C, P292R, N296Y, N296M, N296F, L297W, Q299I, S301Q, N306V, L312F, L312V, G315V, V318E, V318A, Q319A, R320C, H321E, H321V, H321C, P322E, P322C, A325V, A325S, P336E, P336D, P336R, P336L, G337M, G337V, E341D, E341I, S342A, V344L, G346V, F348Q, F348S, F348C, K349G, K349A, K349Y, K349L, K349S, P350L, P350G, P350S, P350Q, L351S, Q361A, Q361E, G362Y, G362R, G362C, G362N, G362M, G362V, Y363Q, Y363I, Y363A, Y368I, Y368L, Y368A, Y368S, Y368Q, Y368V, Y368H, G369K, G369S, G369A, G369E, G369R, G369I, D370T, Y372L, Y372G, G373S, S376L, D377L, D377V, V379P, P380I, S381L, S381A, S381I, S381V, Y382A, Y382E, Y382V, Y382L, Q384R, Q384Y, D387V, D387Q, D387L, Q394S, Q394R, Q395R, A397G, R400L, R400C, R400K, R400S, R400M, H402S, H402P, H402Y, H407D, W408R, W408P, W408C, W408Y, W408G, W408D, V410Q, R415F, R415L, N418A, N418C, N418M, N418G, H421C, H421A, H421R, S431A, G435E, G435N, G436T, W439R, W439N, M440L, R444V, R444P, Q445C, Q445E, A447E, A447T, M454V, G456R, S459T, N465Q, N465L, N465R, D467V, N475H, G477Q, G477F, G477K, G477L, and V481S, wherein the numbering is according to the amino acid sequence set forth in SEQ ID NO: 3, and wherein the one or more substitutions provides a variant having an IF≥1.4 for a measure of specific activity in Model A detergent composition, and optionally, an IF≥1.0 for a measure of stability.

In one embodiment, the variant comprises one or more substitutions selected from the group consisting of; H1V, G7F, G7V, G7E, G7E, G7D, Q11V, W15G, W15S, N19G, N19S, Q22C, Q22A, N25V, R26L, N29G, A31S, L34Y, A41Q, W48C, W48I, W48Y, S52M, S52V, Q53V, Q53L, V56L, G59E, T74V, T74L, I89A, R90L, S91A, S91G, L92C, N95E, N95S, N95G, Q98L, Y100W, K108V, F113M, F113V, F113E, R116Q, V117G, N126G, N126A, N128S, N128E, Q129E, G133A, G133D, A139S, W140H, T141S, T141C, T141G, F143M, F143L, F145A, P146L, Q151L, K156F, K156Q, K156L, K156S, K156G, R158S, T165I, D166S, Q169L, S170A, S170V, R171A, Q172E, L173I, A174V, N175G, K179L, R181A, R181G, K185G, A186S, A186D, Y203W, Y203L, D209V, E212I, N215C, L217S, R219L, K242A, F245G, K269W, L297W, N306V, L312F, L312V, G315V, R320C, P336L, G337V, W439R, W439N, S342A, V344L, P350S, P350Q, Y368H, S376L, S381V, D387Q, D387L, Q395R, N418M, N418G, S431A, G435N, N465L, and N465R, wherein the numbering is according to the amino acid sequence set forth in SEQ ID NO: 3, and wherein the one or more substitutions provides a variant having an IF≥1.4 for a measure of specific activity in Model A detergent composition, and an IF≥1.0 for a measure of stability.

In one embodiment, the variant comprises a substitution at one or more positions selected from the group consisting of; H1, G7, F13, E14, W15, N16, N19, D20, Q22, R26, N29, N30, A31, Q32, P46, W48, G50, T51, S52, Q53, D55, G59, A60, Y64, N70, Q71, K72, G73, T74, V75, K78, R90, Y100, H107, K108, G109, D112, F113, R116, V117, A119, E121, N123, N126, R127, N128, E130, V131, S132, G133, T134, Y135, I137, A139, W140, T141, G142, N144, F145, P146, G147, G149, N150, Q151, F155, K156, R158, W159, Y160, D163, G164, T165, D166, W167, S170, R171, Q172, L173, R176, Y178, K179, R181, K185, A186, W187, D188, W189, V191, E194, D199, Y200, M202, Y203, A204, D205, H210, N215, L217, R219, W223, V238, K242, F245, G258, F262, K269, N270, A274, T285, S287, N296, L312, V318, H321, P322, A325, G337, E341, S342, K349, P350, Q361, G362, Y368, G369, D377, S381, Q384, D387, R400, W408, R415, N418, G435, Q445, M454, G477, and V481; wherein the positions correspond to amino acid positions in the amino acid sequence set forth in SEQ ID NO: 3, which one or more substitutions provides an improvement factor of ≥1.6 for a measure of specific activity in Model A detergent composition, and optionally, an improvement factor of ≥1.0 for a measure of stability.

In a particular embodiment, the variant comprises one or more substitutions selected from the group consisting of; H1C, G7V, G7E, G7E, G7D, F13I, E14L, E14M, E14S, W15S, W15F, N16Q, N19G, N19S, N19V, D20R, Q22A, R26L, R26W, R26A, R26F, N29G, N29L, N30E, A31S, Q32L, Q32A, P46G, W48Y, G50N, T51G, T51P, T51L, T51C, S52V, S52I, S52L, Q53V, Q53L, D55V, D55I, G59A, A60L, A60G, Y64V, Y64I, Y64H, Y64M, Y64C, Y64R, Y64G, Y64L, Y64A, N70S, N70E, Q71I, Q71V, K72R, G73L, G73E, T74V, T74L, V75G, K78T, K78A, R90L, R90G, Y100F, H107Q, K108V, G109A, G109S, D112E, F113E, F113C, F113D, R116I, R116D, R116T, R116G, R116E, R116S, R116C, R116V, R116Q, R116F, V117S, V117W, V117A, V117G, V117E, A119Y, E121G, E121V, E121M, E121D, N123P, N126G, N126A, R127C, R127W, R127L, R127V, R127F, R127Y, N128C, N128E, E130C, V131E, S132H, S132P, S132C, S132E, S132D, G133E, G133D, T134D, T134E, Y135T, Y135W, Y135K, Y135G, Y135P, Y135M, Y135D, I137S, I137G, A139S, W140Y, W140S, W140A, W140H, T141C, T141G, G142E, N144C, F145S, F145A, P146C, P146L, G147I, G147L, G147C, G149C, N150D, N150E Q151T, Q151C, Q151L, F155L, K156V, K156A, K156D, K156W, K156P, K156E, K156C, K156F, K156Q, K156L, K156S, K156G, R158A, R158G, R158Q, R158W, R158L, R158T, R158V, R158E, R158Y, R158S, W159G, W159T, W159C, W159E, W159D, Y160S, Y160V, Y160G, Y160I, Y160L, Y160E, D163L, G164T, G164C, T165G, T165I, D166T, D166N, D166S, W167D, Q169A, Q169L, S170V, R171V, R171A, Q172S, L173V, R176M, Y178R, Y178K, K179C, K179E, K179S, K179W, K179A, K179G, K179T, K179F, R181V, R181Q, R181E, R181G, K185A, K185D, K185N, K185V, K185G, A186D, W187G, D188M, D188L, D188V, W189R, W189A, W189G, W189C, V191M, V191A, E194Q, D199S, D199A, Y200W, Y200F, Y200C, Y200V, Y200T, Y200L, Y200A, Y200G, Y200S, M202T, Y203I, Y203Q, Y203H, Y203T, Y203M, Y203S, Y203V, Y203W, Y203L, A204H, A204W, A204F, A204L, A204Y, A204D, A204G, D205C, H21 OW, H210L, H210G, H210E, N215D, N215V, N215C, L217S, R219Y, R219D, R219C, W223Y, V238C, V238W, K242W, K242G, K242L, K242R, K242S, K242E, K242Q, F245C, F245V, F245D, F245G, G258L, F262E, F262R, F262P, F262V, K269L, N270D, N270A, N270M, A274S, A274D, A274E, T285T, T285S, S287W, S287C, N296M, N296F, L312F, L312V, V318A, H321V, H321C, P322C, A325S, G337M, G337V, E341I, S342A, K349A, K349Y, K349L, K349S, P350G, P350Q, Q361E, G362R, G362C, G362N, G362M, G362V, Y368I, Y368A, Y368S, Y368Q, Y368V, G369K, G369S, G369A, G369E, G369R, G369I, D377V, S381L, S381A, S381I, Q384R, Q384Y, D387L, R400M, W408Y, W408G, W408D, R415L, N418G, G435E, G435N, Q445E, M454V, G477Q, G477F, G477K, G477L, and V481S, wherein the positions correspond to amino acid positions in the amino acid sequence set forth in SEQ ID NO: 3, and wherein the one or more substitutions provides a variant having an IF≥1.6 for a measure of specific activity in Model A detergent composition, and optionally, an IF≥1.0 for a measure of stability.

In one embodiment, the variant comprises one or more substitutions selected from the group consisting of; G7V, G7E, G7E, G7D, W15S, N19G, N19S, Q22A, R26L, N29G, A31S, W48Y, S52V, Q53V, Q53L, T74V, T74L, R90L, K108V, F113E, R116Q, V117G, N126G, N126A, N128E, G133D, A139S, W140H, T141C, T141G, F145A, P146L, Q151L, K156F, K156Q, K156L, K156S, K156G, R158S, T165I, D166S, Q169L, S170V, R171A, R181G K185G, A186D, Y203W, Y203L N215C, L217S, F245G, L312F, L312V, G337V, S342A, P350Q, D387L, N418G, and G435N, wherein the positions correspond to amino acid positions in the amino acid sequence set forth in SEQ ID NO: 3, and wherein the one or more substitutions provides a variant having an IF≥1.6 for a measure of specific activity in Model A detergent composition, and an IF≥1.0 for a measure of stability.

In another embodiment, the variant comprises a substitution at one or more positions selected from the group consisting of: H1, H2, D3, G4, T5, G7, T8, I9, M10, Q11, Y12, F13, E14, W15, N16, P18, N19, Q22, W24, N25, R26, L27, H28, N29, N30, A31, Q32, N33, L34, K35, N36, A37, G38, I39, T40, A41, I42, W43, I44, P45, P46, A47, W48, G50, T51, S52, Q53, N54, D55, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, D112, F113, E115, R116, V117, A119, V120, E121, V122, N123, Q125, N126, R127, N128, Q129, E130, V131, S132, G133, T134, Y135, I137, E138, A139, W140, T141, G142, F143, N144, F145, P146, G147, G149, N150, Q151, S153, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, V222, W223, Y224, A225, N226, T227, L228, N229, L230, D231, F233, V238, I241, K242, F245, M246, W249, L250, H252, V253, R254, G255, Q256, T257, G258, K259, N260, L261, F262, A263, V264, Y267, W268, K269, N270, D271, G273, A274, E276, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, L312, L313, N314, G315, T316, V318, Q319, R320, H321, P322, A325, V326, T327, V329, N331, P336, G337, E341, S342, V344, Q345, G346, W347, F348, K349, P350, L351, A352, T355, L357, T358, E360, Q361, G362, Y363, Q365, V366, Y368, G369, D370, Y372, G373, I374, P375, S376, D377, V379, P380, S381, Y382, R383, Q384, I386, D387, P388, L389, L390, K391, A392, Q394, Q395, Y396, A397, R400, H402, D403, F405, D406, H407, W408, V410, I411, T414, R415, E416, N418, A419, S420, H421, S424, G425, A427, T428, I429, M430, S431, G435, G436, S437, K438, W439, M440, Y441, V442, R444, Q445, K446, A447, G448, V450, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence as set forth in SEQ ID NO: 3, and wherein the one or more substitutions provides a variant having an IF of ≥1.2 for a measure of specific activity in Model X detergent composition and optionally an IF of ≥1.0 for a measure of stability.

In one embodiment, the variant comprises one or more substitutions selected form the group consisting of; H1V, H1G, H1S, H1C, H2L, H2T, H2M, H2E, H2P, H2G, D3C, D3A, G4Q, G4D, T5L, T5Q, T5G, T5E, T5V, G7F, G7R, G7V, G7E, G7E, G7D, T8A, T8S, I9C, I9M, I9L, M10L, Q11C, Q11L, Q11V, Y12V, Y12A, Y12F, F13Y, F13I, E14L, E14M, E14S, W15G, W15F, W15S, N16G, N16Q, P18L, N19Y, N19T, N19G, N19S, N19V, Q22N, Q22C, Q22S, Q22M, Q22T, Q22E, Q22A, W24H, W24F, N25V, N25S, N25G, N25E, N25E, R26G, R26D, R26M, R26I, R26S, R26L, R26W, R26A, R26F, L27A, L27M, H28A, H28E, H28I, N29C, N29G, N29L, N30S, N30H, N30L, N30T, N30E, A31W, A31V, A31S, Q32D, Q32G, Q32L, Q32A, N33F, N33A, N33R, L34F, L34Y, K35L, K35E, K35W, K35Q, N36R, N36Q, N36A, N36E, A37R, A37G, A37T, A37S, G38N, I39L, I39M, T40Q, T40D, T40A, T40E, A41E, A41N, A41M, A41Q, A41D, I42V, I42A, W43R, I44T, P45A, P46G, A47S, A47G, W48G, W48L, W48C, W48I, W48M, W48P, W48Q, W48Y, W48F, G50P, G50S, G50N, T51S, T51G, T51P, T51L, T51C, S52M, S52V, S52I, S52L, Q53G, Q53V, Q53L, N54G, N54K, N54V, D55V, D55I, V56L, V56M, G59E, G59A, A60S, A60W, A60L, A60G, A60T, Y61F, L63V, L63P, L63I, L63H, L63K, Y64W, Y64S, Y64V, Y64I, Y64H, Y64M, Y64C, Y64R, Y64G, Y64L, Y64A, L66M, E68D, F69H, F69W, N70G, N70A, N70T, N70S, N70E, Q71N, Q71E, Q71D, Q71I, Q71V, K72Y, K72R, G73V, G73L, G73E, T74V, T74L, V75T, V75G, R76S, R76G, R76A, T77A, T77S, K78L, K78T, K78A, T81G, T81W, T81L, K82A, A83G, A83E, E84F, E84D, L85V, E86L, E86D, R87M, R87A, R87E, A88S, A88G, A88V, I89A, I89H, I89P, R90L, R90G, S91A, S91E, S91G, L92C, K93W, K93G, K93L, N95L, N95E, N95W, N95C, N95S, N95G, G96Q, I97M, I97V, Q98V, Q98L, Q98C, Q98M, Q98T, V99I, V99L, V99S, V99T, Y100W, Y100V, Y100F, V103G, H107Q, K108V, G109A, G109S, D112E, F113M, F113V, F113L, F113C, F113E, F113D, F113Y, E115C, E115A, R116N, R116L, R116I, R116Q, R116D, R116T, R116G, R116E, R116S, R116C, R116V, R116F, V117C, V117L, V117S, V117W, V117A, V117G, V117E, A119Y, V120I, V120D, V120L, E121P, E121G, E121V, E121M, E121D, V122E, V122P, V122I, N123G, N123A, N123E, N123W, N123T, N123P, Q125E, Q125T, N126E, N126G, N126A, R127G, R127S, R127C, R127W, R127L, R127V, R127F, R127Y, N128S, N128E, N128C, Q129L, Q129C, Q129E, E130C, V131L, V131E, S132A, S132H, S132P, S132C, S132E, S132D, A132N, G133S, G133T, G133L, G133A, G133V, G133I, G133E, G133D, T134V, T134D, T134E, Y135L, Y135V, Y135S, Y135R, Y135T, Y135W, Y135K, Y135G, Y135P, Y135M, Y135D, Y135H, Y135E, Y135E, I137A, I137S, I137G, E138A, A139M, A139S, W140Y, W140S, W140H, W140A, T141S, T141M, T141C, T141G, G142D, G142E, F143M, F143L, N144C, F145C, F145S, F145A, P146S, P146V, P146L, P146C, G147V, G147P, G147D, G147S, G147I, G147L, G147C, G149C, N150C, N150D, N150E, Q151L, Q151T, Q151C, S153C, F155H, F155T, F155L, K156Y, K156V, K156A, K156F, K156D, K156Q, K156L, K156S, K156W, K156P, K156E, K156C, K156G, W157L, R158M, R158A, R158G, R158Q, R158S, R158W, R158L, R158T, R158V, R158E, R158Y, W159N, W159G, W159T, W159C, W159E, W159D, W159H, Y160Q, Y160M, Y160T, Y160A, Y160S, Y160V, Y160G, Y160I, Y160L, Y160E, H161C, H161N, F162M, F162L, F162Y, F162I, D163S, D163K, D163A, D163R, D163L, G164S, G164T, G164C, T165L, T165M, T165S, T165G, T165I, D166T, D166S, D166N, W167Y, W167G, W167D, D168M, D168S, D168G, Q169L, S170A, S170V, R171F, R171S, R171K, R171A, R171V, Q172L, Q172E, Q172S, L173I, L173G, L173N, L173M, L173S, L173Y, L173V, A174V, A174G, N175L, N175V, N175I, N175G, R176E, R176W, R176G, R176M, I177L, I177S, I177G, Y178V, Y178R, Y178K, K179L, K179C, K179E, K179S, K179W, K179A, K179G, K179T, K179F, F180A, F180L, R181K, R181P, R181S, R181A, R181V, R181Q, R181G, R181E, G184L, G184R, G184V, G184D, K185A, K185D, K185N, K185G, K185V, A186S, A186C, A186D, W187G, D188Q, D188G, D188R, D188M, D188L, D188V, W189R, W189A, W189G, W189C, E190D, E190N, E190A, V191M, V191A, D192E, D192Q, D192S, T193S, T193K, T193V, T193C, T193P, E194S, E194D, E194L, E194Q, N195R, N195A, G196A, G196V, N197G, N197V, N197Y, N197C, N197D, Y198W, D199G, D199S, D199A, Y200W, Y200F, Y200C, Y200V, Y200T, Y200L, Y200A, Y200G, Y200S, M202T, Y203F, Y203G, Y203C, Y203I, Y203Q, Y203H, Y203W, Y203T, Y203L, Y203M, Y203S, Y203V, A204P, A204R, A204C, A204H, A204W, A204F, A204L, A204Y, A204D, A204G, D205C, V206H, V206Q, V206P, M208R, M208P, M208L, M208C, D209C, D209S, D209M, D209E, D209H, D209F, D209Y, D209V, H210F, H210V, H210A, H210W, H210L, H210G, H210D, H210E, H210N, P211G, P211W, P211C, E212G, E212F, E212M, E212D, E212I, V213C, V213M, V213T, V213G, V213W, I214P, N215D, N215C, N215V, L217V, L217C, L217P, L217T, L217G, L217S, N218S, R219L, R219H, R219W, R219S, R219I, R219A, R219M, R219T, R219E, R219Y, R219D, R219C, V222E, V222F, V222C, W223Y, Y224L, A225K, N226C, N226Q, T227S, T227L, T227M, T227C, L228A, L228F, N229T, N229S, L230S, L230A, L230T, L230V, F233A, F233L, C238V, V238W, I241L, K242A, K242C, K242Y, K242P, K242W, K242G, K242L, K242R, K242S, K242E, K242Q, F245C, F245V, F245D, F245G, M246L, M246F, W249L, L250C, L250W, L250T, L250A, H252C, H252E, H252W, V253A, V253L, V253S, V253W, R254Q, R254S, G255C, G255E, G255L, Q256P, T257V, G258P, G258V, G258C, G258I, G258L, K259L, K259V, K259Q, K259I, N260W, N260E, N260D, N260C, L261G, L261D, F262Q, F262L, F262E, F262R, F262P, F262V, A263L, A263C, V264T, V264L, Y267V, Y267L, W268V, K269W, K269L, N270D, N270A, N270M, D271E, D271V, D271C, G273W, G273R, G273V, A274S, A274D, A274E, E276R, Y278G, Y278S, L279Q, L279V, L279G, S280C, K281L, K281A, K281W, K281G, T282G, T282A, T282C, T282R, T282I, N283G, N283E, N283Q, N283V, N283A, W284T, W284I, W284S, W284E, W284C, W284V, W284A, T285E, T285F, T285S, M286L, M286D, S287V, S287Q, S287T, S287E, S287P, S287L, S287W, S287C, A288L, A288Y, V291T, P292A, P292Q, P292L, P292R, L293A, L293E, L293T, L293G, H294G, H294A, Y295H, Y295S, Y295F, N296A, N296Y, N296M, N296F, L297S, L297W, Y298V, Y298P, Q299S, Q299L, Q299R, Q299I, A300V, S301A, S301R, S301Q, N302I, N302T, N302M, S303I, S303E, S304I, S304P, G305V, G305L, G305S, N306V, Y307F, Y307W, M309L, L312F, L312V, L313S, N314Y, N314F, N314D, G315I, G315V, T316K, T316S, V318C, V318L, V318E, V318A, Q319L, Q319I, Q319A, R320V, R320L, R320C, H321T, H321E, H321V, H321C, P322E, P322C, A325V, A325S, V326I, T327V, T327L, T327S, V329A, V329S, N331C, N331V, N331I, P336M, P336E, P336D, P336L, P336R, G337T, G337C, G337V, G337M, W439R, W439N, E341C, E341D, E341I, S342G, S342T, S342A, V344S, V344L, Q345K, Q345C, Q345V, Q345L, Q345I, G346H, G346A, G346R, G346L, G346N, G346Q, G346V, W347L, F348Q, F348S, F348C, K349G, K349A, K349Y, K349L, K349S, P350S, P350L, P350G, P350Q, L351W, L351M, L351S, A352S, A352C, T355V, T355A, L357C, L357T, L357S, T358V, T358F, E360S, E360D, E360C, Q361V, Q361P, Q361R, Q361A, Q361E, G362Y, G362R, G362C, G362N, G362M, G362V, Y363L, Y363Q, Y363I, Y363A, Q365D, V366L, V366A, Y368M, Y368T, Y368H, Y368I, Y368L, Y368A, Y368S, Y368Q, Y368V, G369K, G369S, G369A, G369E, G369R, G369I, D370A, D370T, Y372S, Y372I, Y372L, Y372G, G373C, G373S, I374Y, P375L, P375A, P375T, S376A, S376N, S376P, S376R, S376W, S376L, D377C, D377L, D377V, V379L, V379F, V379P, P380L, P380V, P380G, P380E, P380A, P380I, S381N, S381V, S381L, S381A, S381I, Y382I, Y382A, Y382E, Y382V, Y382L, R383G, R383S, R383P, Q384A, Q384P, Q384L, Q384H, Q384R, Q384Y, I386T, D387H, D387Q, D387V, D387L, P388G, P388T, P388M, P388W, P388V, L389S, L389H, L390V, L390S, L390F, L390I, L390G, K391L, K391Y, K391A, A392I, Q394S, Q394R, Q395W, Q395E, Q395K, Q395N, Q395L, Q395R, Y396T, Y396L, A397C, A397G, R400L, R400C, R400K, R400S, R400M, H402L, H402V, H402E, H402M, H402A, H402S, H402P, H402Y, D403E, F405G, F405C, F405V, F405I, F405P, F405W, D406E, H407C, H407D, W408R, W408P, W408C, W408Y, W408G, W408D, V410I, V410Q, I411A, I411L, I411V, T414A, T414V, R415F, R415L, E416C, E416V, N418L, N418M, N418A, N418C, N418G, A419M, A419E, A419C, S420E, S420T, S420V, H421V, H421C, H421A, H421R, S424C, S424A, G425A, A427V, T428L, T428N, T428A, T428G, I429V, I429A, M430L, M430R, S431A, G435N, G435E, G436M, G436E, G436L, G436T, S437G, S437Q, S437L, K438T, W439E, W439C, W439H, M440L, Y441N, Y441H, Y441Q, V442I, R444A, R444S, R444L, R444V, R444P, Q445L, Q445S, Q445C, Q445E, K446G, K446Q, A447G, A447Q, A447E, A447T, G448S, V450T, V450A, H452A, H452T, D453E, M454R, M454L, M454V, T455L, T455S, G456Y, G456V, G456R, N457V, N457I, N457G, N457R, S459E, S459Q, S459V, S459C, S459P, S459M, S459T, G460S, G460D, G460E, T463C, T463V, T463L, T463D, T463H, I464V, N465G, N465L, N465R, N465Q, Q466L, Q466C, Q466E, D467C, D467V, W469M, W469E, W469T, H471Q, F473Y, F473C, F473R, N475T, N475H, Q476Y, G477Q, G477F, G477K, G477L, V481Q, V481S, W482F, wherein the positions correspond to amino acid positions in the amino acid sequence as set forth in SEQ ID NO: 3, and wherein the one or more substitutions provides a variant having an IF of ≥1.2 for a measure of specific activity in Model X detergent compositions, and optionally an IF of ≥1.0 for a measure of stability.

In one embodiment, the variant comprises a substitution in one or more positions selected from the group consisting of; H1, H2, D3, G4, T5, G7, I9, Q11, F13, E14, N16, N19, Q22, W24, N25, R26, N29, A31, Q32, L34, N36, A37, A41, P45, P46, W48, G50, T51, S52, Q53, G59, A60, Y61, L63, Y64, F69, N70, Q71, K72, G73, T74, V75, R76, T77, K82, R87, I89, R90, S91, L92, K93, N95, Q98, V99, Y100, K108, G109, D112, F113, R116, V117, A119, V120, E121, V122, N123, N126, R127, N128, Q129, E130, V131, S132, G133, T134, Y135, I137, A139, W140, T141, G142, F143, N144, F145, P146, G147, G149, N150, Q151, F155, K156, R158, W159, Y160, D163, T165, D166, W167, D168, Q169, R171, Q172, L173, A174, N175, R176, I177, Y178, K179, F180, R181, G184, K185, A186, W187, D188, E194, D199, Y200, M202, Y203, A204, D205, H210, E212, N215, L217, R219, W223, N226, L230, V238, I241, K242, K245, R254, G258, N260, F262, A263, K269, N270, D271, A274, L279, K281, N283, W284, T285, S287, P292, L293, N296, Q299, S301, G305, N306, L312, N314, G315, V318, Q319, R320, H321, P322, A325, G337, W439, E341, S342, V344, Q345, G346, F348, K349, P350, L357, E360, Q361, G362, Y363, Y368, G369, Y372, I374, P375, S376, D377, V379, P380, S381, Y382, Q384, D387, P388, Q394, Q395, A397, R400, H402, W408, V410, R415, N418, H421, G425, S431, G435, G436, W439, R444, Q445, A447, G456, S459, N465, W469, G477, and V481, wherein the positions correspond to amino acid positions in the amino acid sequence as set forth in SEQ ID NO: 3, and wherein the substitution in one or more positions provides a variant having an IF of ≥1.4 for a measure of specific activity in Model X detergent composition and optionally, an IF of at least ≥1.0 for a measure of stability.

In one embodiment, the variant comprises one or more of the substitutions selected from the group consisting of; H1G, H1C, H2G, D3A, G4D, T5Q, T5E, T5V, G7F, G7E, G7R, G7V, G7E, G7D, I9M, Q11V, F13I, E14M, N16G, N16Q, N19Y, N19T, N19G, N19S, N19V, Q22N, Q22C, Q22S, Q22M, Q22A, W24F, N25G, N25E, N25E, R26G, R26D, R26I, R26S, R26L, R26W, R26A, R26F, N29G, N29L, A31W, A31S, Q32G, Q32L, Q32A, L34Y, N36E, A37G, A41Q, P45A, P46G, W48G, W48C, W48I, W48M, W48P, W48Q, G50S, G50N, T51G, T51C, S52V, S52I, S52L, Q53L, Q53G, Q53V, G59A, A60S, A60W, A60L, A60G, A60T, Y61F, L63V, L63H, L63K, Y64W, Y64S, Y64V, Y64I, Y64H, Y64M, Y64C, Y64R, Y64G, Y64L, Y64A, F69W, N70A, N70T, N70S, N70E, Q71N, Q71D, Q71I, Q71V, K72Y, K72R, G73V, G73L, G73E, T74L, V75G, R76A, T77S, K82A, R87A, I89A, I89P, R90L, R90G, S91A, S91E, S91G, L92C, K93W, K93G, N95W, N95C, N95G, Q98L, Q98C, Q98M, Q98T, V99S, V99T, Y100W, Y100V, Y100F, K108V, G109A, G109S, D112E, F113M, F113V, F113L, F113C, F113E, F113D, R116N, R116L, R116I, R116Q, R116D, R116T, R116G, R116E, R116S, R116C, R116V, R116F, V117C, V117S, V117W, V117A, V117G, V117E, A119Y, V120D, V120L, E121V, E121M, E121D, V122E, N123G, N123A, N123E, N123W, N123T, N123P, N126E, N126G, N126A, R127G, R127S, R127C, R127W, R127L, R127V, R127F, R127Y, N128C, N128S, N128E, Q129E, E130C, V131L, V131E, S132A, S132H, S132P, S132C, S132E, S132D, G133S, G133V, G133I, G133E, G133D, T134V, T134D, T134E, Y135V, Y135S, Y135R, Y135T, Y135W, Y135K, Y135G, Y135P, Y135M, Y135D, Y135H, Y135E, I137A, I137S, I137G, A139S, W140Y, W140H, T141M, T141C, T141G, T141S, G142D, G142E, F143M, N144C, F145C, F145A, P146C, P146L, G147V, G147P, G147D, G147S, G147I, G147L, G147C, G149C, N150C, N150D, N150E, Q151T, Q151L, F155H, F155L, K156Y, K156V, K156A, K156D, K156Q, K156W, K156P, K156E, K156C, K156F, K156L, K156S, K156G, R158M, R158A, R158G, R158Q, R158S, R158W, R158L, R158T, R158V, R158E, R158Y, W159N, W159G, W159T, W159C, W159E, W159D, Y160Q, Y160T, Y160S, Y160V, Y160G, Y160I, Y160L, Y160E, D163S, D163K, D163L, T165M, T165G, T165I, D166S, W167Y, W167D, D168M, D168S, D168G, Q169L, R171F, R171S, R171K, R171V, R171A, Q172S, Q172E, L173G, L173N, L173M, L173S, L173Y, L173V, A174G, N175L, N175V, N175I, N175G, R176E, R176G, R176M, I177G, Y178V, Y178R, Y178K, K179L, K179C, K179E, K179S, K179W, K179A, K179G, K179T, K179F, F180L, R181K, R181P, R181S, R181V, R181Q, R181E, R181A, R181G, G184V, G184D, K185A, K185D, K185N, K185V, K185G, A186C, A186S, A186D, W187G, D188Q, D188G, D188M, D188L, D188V, E194Q, D199G, D199S, D199A, Y200W, Y200F, Y200C, Y200V, Y200T, Y200L, Y200A, Y200G, Y200S, M202T, Y203I, Y203Q, Y203H, Y203T, Y203M, Y203V, Y203L, A204R, A204H, A204W, A204F, A204L, A204Y, A204D, A204G, D205C, H210F, H210A, H210W, H210L, H210G, H210D, H210E, E212F, E212M, E212D, E212G, E212I, N215D, N215V, N215C, L217C, L217P, R219H, R219I, R219M, R219T, R219E, R219Y, R219D, R219C, W223Y, N226Q, N226C, L230V, V238C, V238W, I241L, K242C, K242Y, K242P, K242W, K242G, K242L, K242R, K242S, K242E, K242A, K242Q, F245C, F245V, F245D, F245G, R254Q, R254S, G258L, N260D, F262Q, F262L, F262E, F262R, F262P, F262V, A263L, A263C, K269L, K269W, N270D, N270A, N270M, D271C, A274S, A274D, A274E, L279Q, L279G, K281W, K281G, N283Q, N283V, N283A, W284C, W284V, W284A, T285F, T285S, S287V, S287Q, S287P, S287L, S287W, S287C, P292R, L293G, N296M, N296F, Q299S, Q299I, S301Q, G305V, G305L, N306V, L312F, L312V, N314F, G315I, G315V, V318A, Q319A, R320L, R320C, H321E, H321V, H321C, P322E, P322C, A325V, A325S, G337C, G337V, G337M, E341D, E341I, S342A, V344L, Q345C, G346Q, G346V, F348Q, F348S, F348C, K349L, K349S, P350S, P350L, P350G, P350Q, L357T, E360C, Q361A, Q361E, G362R, G362C, G362N, G362M, G362V, Y363I, Y363A, Y368I, Y368L, Y368V, G369A, G369R, Y372L, Y372G, I374Y, P375T, S376L, D377V, V379F, V379P, V379L, P380G, P380I, S381N, S381L, S381A, S381I, S381V, Y382V, Q384R, Q384Y, D387L, P388W, Q394S, Q394R, Q395R, A397G, R400M, H402L, H402S, H402P, W408P, W408C, W408Y, V410Q, R415L, N418C, N418G, H421R, G425A, S431A, G435N, G435E, G436M, G436E, G436T, W439H, W439R, W439N, R444V, Q445C, Q445E, A447E, A447T, G456R, S459T, N465R, N465Q, W469M, W469E, G477Q, G477F, G477K, G477L, and V481S, wherein the positions correspond to amino acid positions in the amino acid sequence as set forth in SEQ ID NO: 3, and wherein the one or more substitution provides a variant having an IF of ≥1.4 for a measure of specific activity in Model X detergent composition, and optionally an IF of ≥1.0 for a measure of stability.

In one embodiment, the variant comprises a substitution in one or more positions selected from the group consisting of; G7, F13, N16, N19, R26, N29, A31, P46, G50, T51, S52, Q53, G59, A60, Y64, N70, Q71, K72, G73, T74, R90, K108, G109, F113, R116, V117, A119, E121, V122, N123, N126, R127, E130, V131, S132, G133, T134, Y135, I137, T141, G142, F143, N144, P146, G147, G149, N150, F155, K156, R158, W159, Y160, D163, T165, W167, D168, Q169, R171, Q172, L173, N175, Y178, K179, R181, K185, A186, W187, D188, E194, Y200, Y203, A204, D205, H210, N215, R219, W223, V238, K242, K245, G258, F262, K269, N270, A274, L279, K281, W284, T285, S287, Q299, L312, H321, A325, G337, E341, S342, F348, K349, P350, Q361, G362, Y368, G369, D377, V379, P380, S381, Q384, V410, N418, G435, Q445, G456, N465, and G477 wherein the positions correspond to amino acid positions in the amino acid sequence set forth in SEQ ID NO: 3, and wherein the substitution in one or more positions provides a variant having an IF of ≥1.6 for measure of specific activity in Model X detergent composition, and optionally, an IF of ≥1.0 for a measure of stability.

In one embodiment, the variant comprises one or more substitutions selected from the group consisting of; G7V, G7E, G7D, F13I, N16Q, N19T, N19G, N19S, N19V, R26A, N29G, A31S, P46G, G50N, T51G, T51C, S52I, S52L, Q53L, Q53G, Q53V, G59A, A60S, A60W, A60G, Y64V, Y64M, Y64C, Y64R, Y64G, Y64L, Y64A, N70E, Q71V, K72R, G73L, G73E, T74L, R90G, K108V, G109S, F113V, F113C, F113E, F113D, R116I, R116Q, R116D, R116T, R116G, R116E, R116S, R116C, R116V, R116F, V117A, V117G, V117E, A119Y, E121D, V122E, N123T, N126G, R127W, R127L, R127F, R127Y, E130C, V131L, V131E, S132H, S132P, S132C, S132E, S132D, G133E, G133D, T134V, T134D, T134E, Y135S, Y135T, Y135W, Y135K, Y135G, Y135P, Y135M, Y135D, Y135E, I137S, I137G, T141G, G142D, G142E, N144C, P146C, P146L, G147S, G147L, G149C, N150D, N150E, F155L, K156Y, K156A, K156D, K156Q, K156W, K156P, K156E, K156C, K156F, K156L, K156S, K156G, R158A, R158G, R158Q, R158S, R158W, R158L, R158T, R158V, R158E, R158Y, W159T, W159C, W159E, W159D, Y160S, Y160V, Y160I, Y160L, Y160E, D163L, T165I, W167D, D168G, Q169L, R171V, Q172S, L173V, N175L, N175V, N175I, N175G, Y178K, K179A, K179G, K179T, K179F, R181V, R181Q, R181E, R181G, K185A, K185D, K185N, K185V, K185G, A186S, W187G, D188V, E194Q, Y200C, Y200T, Y200L, Y200A, Y200G, Y200S, Y203M, Y203V, Y203L, A204L, A204D, A204G, D205C, H210F, H210A, H210W, H210L, H210G, H210D, H210E, N215V, R219Y, R219D, R219C, W223Y, V238W, K242R, K242S, K242E, K242A, K242Q, F245D, F245G, G258L, F262Q, F262E, F262R, F262P, F262V, K269L, N270D, N270M, A274E, L279G, K281G, W284A, T285F, S287V, S287W, S287C, Q299I, L312F, L312V, H321V, H321C, A325S, G337V, G337M, E341I, S342A, F348Q, F348S, K349L, K349S, P350L, P350G, Q361E, G362R, G362V, Y368L, Y368V, G369A, D377V, V379P, P380I, S381L, S381A, S381I, Q384Y, V410Q, N418G, G435E, Q445E, G456R, N465R, and G477L, wherein the positions correspond to amino acid positions in the amino acid sequence as set forth in SEQ ID NO: 3, and wherein the one or more substitutions provide a variant having an IF of ≥1.6 for a measure of specific activity in Model X detergent composition and optionally an IF of ≥1.0 for a measure of stability.

The variants according to the present invention have further been shown to have an improved stability in liquid detergent compositions. Thus, in one embodiment, variant has an improved stability, such as an improved storage stability.

In one embodiment, the variant comprises a substitution in one or more positions selected from the group consisting of; H1, H2, D3, T5, G7, I9, Q11, E14, W15, N16, V17, N19, Q22, H23, W24, N25, R26, H28, N29, N30, A31, N33, L34, K35, N36, A37, G38, I39, T40, A41, I42, I44, A47, W48, K49, T51, S52, Q53, N54, D55, V56, G59, A60, L63, E68, G73, T74, V75, R76, T77, T81, K82, A83, E84, E86, I89, R90, S91, L92, N95, G96, I97, Q98, V99, Y100, V103, H107, K108, G109, G110, A111, D112, F113, T114, R116, V117, Q118, V120, V122, N123, P124, N126, N128, Q129, V131, G133, Q136, I137, E138, A139, W140, T141, G142, F143, N144, F145, P146, G149, Q151, S153, S154, F155, K156, R158, Y160, H161, T165, D166, Q169, S170, R171, Q172, L173, A174, N175, R176, Y178, K179, R181, G184, K185, A186, T193, N195, G196, Y198, Y203, D205, V206, D209, H210, E212, V213, I214, N215, L217, N218, R219, W220, G221, V222, W223, N226, T227, L228, D231, F233, V238, H240, K242, S244, F245, R247, D248, W249, L250, G251, H252, V253, T257, G258, K259, N260, L261, V264, W268, K269, L272, G273, L275, E276, N277, L279, S280, K281, T285, M286, A288, P292, L293, H294, Y295, N296, L297, Q299, A300, N302, S303, S304, G305, N306, R310, N311, L312, L313, G315, T316, V318, Q319, R320, H321, S323, V326, T327, F328, V329, T334, P336, G337, E338, E341, S342, V344, Q345, G346, W347, F348, P350, L351, A354, T355, L357, T358, E360, Q361, Y363, Q365, V366, F367, Y368, G369, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, D409, V410, T414, R415, E416, N418, A419, S420, H421, P422, S424, G425, L426, A427, M430, S431, D432, G435, W439, Y441, Q445, K446, A447, G448, V450, W451, H452, M454, G456, S459, T463, N465, D467, F473, N475, G476, and W482; wherein the positions correspond to amino acid positions of the amino acid sequence as set forth in SEQ ID NO: 3, and wherein the one or more substitutions provides a variant having an IF of ≥1.0 for a measure of stability.

In one embodiment, the variant comprises one or more substitutions selected from the group consisting of; H1V, H1L, H2T, D3R, D3Y, D3W, D3S, D3F, T5L, T5F, T5W, G7F, G7V, G7E, G7E, G7D, G7L, G7A, G7S, G7N, I9M, I9L, Q11L, Q11V, Q11M, E14Q, E14F, W15G, W15S, W15I, W15H, N16R, V17D, V17G, V17E, V17Q, V17A, V17T, V17L, N19G, N19S, Q22C, Q22A, Q22Y, H23W, W24F, N25V, N25R, N25L, N25T, R26L, R26E, H28E, H28R, H28M, H28W, H28K, N29G, N29K, N29V, N29W, N29A, N30S, N30R, A31S, A31G, A31R, N33D, L34Y, K35L, N36V, N36P, N36W, N36T, A37E, G38M, G38Y, G38K, I39L, I39V, T40Q, T40A, T40S, A41Q, I42V, I42L, I44T, I44L, I44V, A47G, A47T, W48C, W48I, W48H, W48A, W48Y, W48F, K49Q, T51A, S52M, S52V, S52C, S52F, S52A, S52D, S52K, S52N, S52E, S52T, Q53V, Q53L, Q53M, N54T, N54L, N54I, D55G, V56L, G59E, G59S, A60V, A60F, L63C, L63G, L63A, E68S, E68M, E68C, E68T, E68V, E68Q, E68Y, G73C T74V, T74L, T74N, V75T, V75E, R76V, T77V, T81G, K82G, A83Q, A83R, A83S, A83F, A83V, E84M, E84W, E86W, E86R, I89A, I89L, R90L, S91A, S91G, S91V, S91T, L92C, L92F, N95E, N95S, N95G, N95D, N95R, G96R, I97V, I97L, Q98V, Q98L, Q98F, Q98W, Q98P, Q98H, V99G, V99E, Y100W, V103A, V103S, V103T, H107M, K108V, G109D, G109F, G110C, A111S, D112V, D112F, D112C, D112K, F113M, F113V, F113E, F113K, F113Y, T114S, T114V, T114L, R116Q, R116K, R116W, V117G, V117I, V117M, Q118V, Q118G, Q118E, Q118F, Q118R, V120C, V120A, V120N, V122L, N123K, N123V, P124R, P124G, N126G, N126A, N126R, N126T, N128S, N128E, N128P, N128G, N128A, Q129E, V131I, G133A, G133D, G133R, Q136E, Q136W, Q136G, I137V, E138A, E138Y, E138T, E138L, A139S, A139G, A139V, A139T, A139P, W140H, T141S, T141C, T141G, G142R, G142A, F143M, F143L, F143I, N144M, N144K, N144G, N144R, F145A, F145N, F145Q, F145T, F145H, P146L, P146M, P146T, G149Y, G149L, G149A, Q151L, Q151I, S153G, S153T, S154M, S154E, S154A, S154V, F155W, K156F, K156Q, K156L, K156S, K156G, K156N, K156T, R158S, Y160W, Y160R, Y160H, H161C, T165I, T165V, T165E, D166S, Q169L, Q169S, Q169V, Q169F, S170A, S170V, S170Q, S170W, S170G, S170F, S170T, S170L, R171A, R171M, Q172L, Q172E, Q172C, Q172R, Q172G, Q172W, L173I, L173A, A174V, A174L, A174M, A174K, N175G, N175S, R176Y, R176M, R176T, R176K, Y178W, K179L, R181A, R181G, R181D, G184D, K185G, A186S, A186D, A186T, A186Q, A186V, A186H, T193S, T193D, T193R, T193G, N195T, N195F, G196P, Y198A, Y198G, Y203W, Y203L, D205R, D205A, D205L, V206A, V206S, V206K, D209S, D209M, D209V, D209Q, D209L, D209I, H210Q, H210N, E212G, E212I, E212Y, E212R, E212C, E212K, V213C, V213W, V213R, V213F, I214V, N215C, N215T, L217S, L217A, L217W, N218S, N218D, N218R, N218L, N218M, R219L, W220L, W220I, W220P, W220E, W220R, W220A, W220S, G221S, G221A, V222E, V222L, W223F, W223L, N226C, N226M, N226E, N226K, N226R, T227L, T227Y, T227R, L228F, L228M, D231P, F233T, F233P, F233M, V238A, H240W, K242A, S244Q, F245G, F245A, R247Y, R247G, R247M, D248G, D248R, W249F, L250C, L250F, L250Y, G251K, G251M, G251Q, H252C, H252T, H252F, H252V, V253A, V253L, T257V, G258P, G258F, G258D, K259L, K259A, K259S, K259D, K259C, N260W, N260S, N260R, N260G, L261T, V264L, W268Y, K269W, K269Q, K269R, L272M, G273E, L275G, L275E, L275A, L275R, L275K, E276L, N277D, L279Q, L279M, S280R, S280E, S280D, K281A, T285W, T285M, T285P, M286L, M286C, A288V, P292L, P292G, L293T, L293G, L293Y, L293Q, H294W, H294Q, H294S, Y295I, Y295A, Y295F, N296S, N296K, N296H, L297W, L297H, Q299S, Q299L, Q299R, Q299A, Q299H, Q299P, A300C, N302S, S303A, S303M, S304G, S304L, S304F, S304A, S304M, G305Q, G305F, G305I, N306V, N306L, N306D, N306S, N306T, R310A, R310T, N311L, N311R, N311C, N311Y, L312F, L312V, L312I, L313M, L313I, G315V, G315T, G315R, G315F, T316S, T316C, T316G, V318L, Q319P, Q319H, Q319D, Q319F, R320V, R320C, R320A, R320S, H321T, H321G, H321R, H321S, S323N, V326G, V326A, V326C, V326T, T327V, T327L, T327Q, T327E, F328M, F328C, V329S, V329C, V329I, T334A, T334S, P336L, P336W, P336S, P336K, G337V, G337F, E338T, E338A, E338H, E341P, E341M, E341F, E341K, E341S, E341T, S342A, V344L, Q345L, Q345W, Q345N, G346R, G346S, W347L, W347R, W347V, W347C, F348P, F348M, P350S, P350Q, P350D, P350E, L351W, L351H, L351Q, A354C, T355L, T355Y, T355F, L357H, T358L, E360G, E360A, E360M, Q361V, Q361G, Q361D, Q361S, Y363L, Y363R, Y363V, Q365M, Q365L, Q365T, Q365C, Q365S, V366I, V366C, F367L, F367S, F367A, Y368H, G369L, Y372A, G373T, G373Q, G373W, G373R, I374Y, I374S, I374M, I374L, P375E, P375S, P375V, P375R, S376R, S376L, S376V, S376I, S376Q, S376F, S376E, S376T, D377S, D377G, D377T, V379L, V379S, P380V, P380Y, S381V, Y382K, Y382R, R383V, Q384S, Q384V, Q384T, Q384G, Q384E, I386L, I386M, I386W, I386V, D387Q, D387L, P388S, P388R, P388K, P388L, L389A, L389V, L389F, L389M, L390V, L390T, L390N, L390H, L390C, K391Q, A392I, A392M, A392T, Q394N, Q394L, Q394T, Q394M, Q395E, Q395K, Q395R, Q395V, Q395S, Q395M, Y396R, Y396W, A397S, Y398S, Y398C, Y398N, Y398K, R400E, R400I, H402L, H402D, H402R, H402T, D403P, D403Q, D403I, Y404K, Y404F, Y404W, F405G, F405A, D406V, D406T, D406M, D406S, D409G, V410L, V410E, T414A, R415A, R415Q, E416V, E416L, E416A, E416Q, N418M, N418G, N418R, N418F, A419M, A419G, A419V, A419L, A419Q, A419R, S420M, H421T, P422Y, P422H, P422D, P422R, S424L, G425V, L426S, L426A, A427S, M430L, M430A, M430T, S431A, S431T, S431F, D432Q, D432P, G435N, G435M, G435I, G435S, W439E, W439A, W439T, W439R, W439N, Y441K, Q445R, K446G, K446T, K446P, A447M, A447S, G448R, V450T, V450Q, V450R, W451L, H452C, H452G, H452Y, H452R, H452V, M454Q, M454S, G456Y, G456K, G456L, S459E, S459Q, S459R, T463M, T463A, T463Q, N465L, N465R, D467C, F473E, F473G, F473T, F473V, N475G, G476F, G476Y, and W482F, wherein the numbering is according to the amino acid sequence set forth in SEQ ID NO: 3, and wherein the one or more substitutions provides a variant having an IF≥1.0 for a measure of stability.

In one embodiment, the variant comprises a substitution at one or more positions selected from the group consisting of; H1, H2, D3, T5, G7, I9, E14, W15, N16, V17, Q22, H23, W24, N25, R26, H28, N29, N33, N36, A37, G38, I39, T40, A41, I42, I44, W48, S52, Q53, N54, D55, V56, G59, A60, L63, E68, G73, T74, V75, R76, T81, A83, E86, R90, S91, L92, N95, I97, Q98, V99, Y100, V103, H107, K108, G109, G110, A111, D112, F113, T114, R116, V117, Q118, V120, V122, N123, P124, N126, N128, Q129, V131, G133, Q136, I137, E138, A139, W140, T141, G142, F143, N144, F145, P146, G149, Q151, S153, S154, F155, K156, Y160, T165, D166, Q169, S170, R171, Q172, L173, A174, N175, R176, K179, R181, K185, A186, T193, N195, G196, Y198, Y203, D205, V206, D209, H210, E212, V213, I214, N215, L217, N218, W220, G221, W223, N226, T227, L228, D231, F233, V238, H240, K242, S244, R247, D248, L250, G251, H252, T257, G258, K259, N260, L261, K269, L272, G273, L275, E276, N277, L279, K281, T285, M286, A288, P292, L293, H294, Y295, N296, L297, Q299, A300, N302, S303, S304, G305, N306, R310, N311, L312, L313, G315, T316, Q319, R320, H321, T327, T334, P336, E338, E341, S342, V344, G346, W347, F348, P350, L351, A354, T355, T358, E360, Q361, Y363, Q365, F367, Y368, G369, G373, I374, P375, S376, D377, V379, S381, Y382, Q384, I386, D387, P388, L389, L390, K391, A392, Q394, Q395, Y396, A397, Y398, R400, H402, D403, Y404, F405, D406, D409, V410, R415, E416, N418, A419, S420, P422, S424, G425, L426, A427, M430, S431, D432, G435, W439, Y441, Q445, K446, A447, V450, H452, M454, G456, S459, F473, and N475; wherein the positions correspond to amino acid positions in the amino acid sequence set forth in SEQ ID NO: 3, which one or more substitution provides an improvement factor of ≥1.2 for a measure of stability and optionally, an improvement factor of ≥1.0 for a measure of specific activity in Model A and/or Model X detergent compositions.

In one embodiment, the variant comprises one or more substitutions selected from the group consisting of; H1V, H1L, H2T, D3R, D3Y, D3W, D3S, D3F, T5L, T5F, T5W, G7F, G7V, G7E, G7E, G7D, G7L, G7A, I9L, E14Q, W15I, N16R, V17D, V17G, V17E, V17Q, V17A, V17T, V17L, Q22C, Q22A, Q22Y, H23W, W24F, N25V, N25R, N25L, N25T, R26L, R26E, H28E, H28R, H28M, H28W, H28K, N29G, N29V, N29W, N33D, N36V, N36P, N36W, A37E, G38Y, G38K, I39L, I39V, T40Q, T40A, T40S, A41Q, I42L, I44T, W48C, W48I, W48H, W48A, W48Y, W48F, S52M, S52V, S52C, S52F, S52A, S52D, S52K, S52N, S52E, S52T, Q53V, Q53L, Q53M, N54T, N54L, N54I, D55G, V56L, G59E, G59S, A60V, A60F, L63C, L63G, L63A, E68S, E68M, E68C, E68T, E68V, E68Q, E68Y, G73C, T74V, T74L, V75T, V75E, R76V, T81G, A83Q, A83R, A83S, A83F, A83V, E86W, E86R, R90L, S91G, S91T, L92C, N95E, N95S, N95G, N95D, N95R, I97L, Q98V, Q98L, Q98W, Q98P, Q98H, V99G, V99E, Y100W, V103S, V103T, H107M, K108V, G109D, G109F, G110C, A111S, D112F, D112C, D112K, F113M, F113V, F113E, F113K, T114S, T114V, T114L, R116Q, R116K, V117G, V117I, V117M, Q118V, Q118G, Q118E, Q118F, Q118R, V120N, V122L, N123K, N123V, P124R, P124G, N126T, N128S, N128E, N128P, N128G, N128A, Q129E, V131I, G133A, G133D, G133R, Q136E, Q136W, Q136G, I137V, E138A, E138Y, E138T, E138L, A139S, A139G, A139V, A139T, A139P, W140H, T141S, T141C, T141G, G142R, G142A, F143M, F143L, F143I, N144M, N144K, N144G, N144R, F145A, F145N, F145Q, F145T, F145H, P146L, P146M, P146T, G149Y, G149L, G149A, Q151L, S153G, S153T, S154M, S154E, S154A, S154V, F155W, K156F, K156Q, K156L, K156S, K156G, K156N, K156T, Y160H, T165I, D166S, Q169L, Q169S, Q169V, Q169F, S170A, S170V, S170Q, S170W, S170G, S170F, S170T, S170L, R171A, R171M, Q172L, Q172E, Q172C, Q172R, Q172G, Q172W, L173I, L173A, A174V, A174L, A174M, A174K, N175G, N175S, R176Y, R176M, R176T, R176K, K179L, R181A, R181G, R181D, K185G, A186S, A186D, A186T, A186Q, A186V, T193S, T193D, T193R, T193G, N195T, N195F, G196P, Y198G, Y203W, Y203L, D205R, D205A, D205L, V206A, V206S, V206K, D209S, D209M, D209V, D209Q, D209L, D209I, H210N, E212G, E212I, E212Y, E212R, E212C, E212K, V213C, V213W, V213R, V213F, I214V, N215C, N215T, L217S, L217A, L217W, N218S, N218D, N218R, N218L, N218M, W220L, W220I, W220P, W220E, W220R, W220A, W220S, G221A, W223L, N226C, N226M, N226E, N226K, N226R, T227L, T227Y, T227R, L228F, D231P, F233T, F233P, F233M, V238A, H240W, K242A, S244Q, R247Y, R247G, R247M, D248G, D248R, L250C, L250F, L250Y, G251K, G251M, G251Q, H252C, H252T, H252F, H252V, T257V, G258D, K259L, K259A, K259S, K259D, K259C, N260W, N260S, N260R, L261T, K269W, K269Q, K269R, L272M, G273E, L275G, L275E, L275A, L275R, L275K, E276L, N277D, L279Q, L279M, K281A, T285W, T285M, T285P, M286L, M286C, A288V, P292L, P292G, L293T, L293G, L293Y, L293Q, H294W, H294Q, H294S, Y295A, N296S, N296K, N296H, L297W, L297H, Q299S, Q299L, Q299R, Q299A, Q299H, Q299P, A300C, N302S, S303M, S304G, S304L, S304F, S304A, S304M, G305F, G305I, N306V, N306L, N306D, N306S, N306T, R310A, R310T, N311L, N311R, N311C, N311Y, L312F, L312V, L312I, L313M, L313I, G315V, G315T, G315R, G315F, T316S, T316C, T316G, Q319P, Q319H, Q319D, Q319F, R320V, H321T, H321G, H321R, H321S, T327V, T327L, T327E, T334A, T334S, P336L, P336W, P336S, P336K, E338A, E338H, E341P, E341M, E341F, E341K, E341S, S342A, V344L, G346S, W347L, W347R, W347V, W347C, F348M, P350Q, L351W, L351H, L351Q, A354C, T355Y, T355F, T358L, E360G, E360A, E360M, Q361S, Y363L, Y363R, Y363V, Q365S, F367L, F367S, F367A, Y368H, G369L, G373T, G373Q, G373W, G373R, I374Y, I374S, I374M, I374L, P375E, P375S, P375V, P375R, S376R, S376V, S376I, S376Q, S376F, S376E, S376T, D377G, D377T, V379L, V379S, S381V, Y382K, Y382R, Q384S, Q384V, Q384T, Q384G, Q384E, I386W, I386V, D387Q, D387L, P388S, P388R, P388K, P388L, L389A, L389V, L389F, L389M, L390V, L390T, L390N, L390H, L390C, K391Q, A392I, A392M, A392T, Q394N, Q394L, Q394T, Q394M, Q395E, Q395K, Q395R, Y396R, Y396W, A397S, Y398S, Y398C, Y398N, Y398K, R400E, R400I, H402R, H402T, D403I, Y404K, Y404F, Y404W, F405G, F405A, D406S, D409G, V410L, V410E, R415Q, E416V, E416L, E416A, E416Q, N418M, N418G, N418R, N418F, A419M, A419G, A419V, A419L, A419Q, A419R, S420M, P422Y, P422H, P422D, P422R, S424L, G425V, L426S, L426A, A427S, M430L, M430A, M430T, S431A, S431T, S431F, D432Q, D432P, G435N, G435M, G435I, G435S, W439E, W439A, Y441K, Q445R, K446G, K446P, A447S, V450R, H452V, M454Q, M454S, G456Y, S459Q, F473E, F473G, F473T, F473V, and N475G, wherein numbering is according to the amino acid sequence set forth in SEQ ID NO: 3, and wherein the one or more substitution provides a variant having an IF of ≥1.2 for a measure of stability, and optionally, an IF of ≥1.0 for a measure of specific activity in Model A and/or Model X detergent compositions.

In one embodiment, the variant comprises one or more substitutions selected from the group consisting of; H1V, H2T, T5L, G7F, G7V, G7E, G7E, G7D, I9L, E14F, Q22C, Q22A, W24F, N25V, R26L, H28E, N29G, N29A, I39L, T40Q, T40A, A41Q, I44T, W48C, W48I, W48Y, W48F, T51A, S52M, S52V, Q53V, Q53L, V56L, G59E, T74V, T74L, V75T, R90L, S91G, L92C, N95E, N95S, N95G, Q98V, Q98L, Y100W, K108V, F113M, F113V, F113E, F113Y, R116Q, V117G, N128S, N128E, Q129E, G133A, G133D, E138A, A139S, W140H, T141S, T141C, T141G, F143M, F143L, F145A, P146L, Q151L, K156F, K156Q, K156L, K156S, K156G, T165I, D166S, Q169L, S170A, S170V, R171A, Q172L, Q172E, L173I, A174V, N175G, K179L, R181A, R181G, G184D, K185G, A186S, A186D, A186H, T193S, Y203W, Y203L, D209S, D209M, D209V, H210N, E212G, E212I, V213C, V213W, N215C, L217S, N218S, N226C, T227L, L228T, K242A, L250C, H252C, T257V, K259L, N260W, N260G, K269W, L279Q, K281A, M286L, P292L, L293T, L293G, Y295F, L297W, Q299S, Q299L, Q299R, N306V, L312F, L312V, G315V, T316S, R320V, H321T, S323N, T327V, T327L, P336L, E341T, S342A, V344L, W347L, P350Q, L351W, Y363L, Y368H, I374Y, S376R, V379L, S381V, D387Q, D387L, L390V, A392I, Q395E, Q395K, Q395R, F405G, E416V, N418M, N418G, A419M, M430L, S431A, G435N, W439E, W439R, W439N, K446G, G456Y, S459Q, and G476Y, wherein numbering is according to the amino acid sequence set forth in SEQ ID NO: 3, and wherein the one or more substitutions provides a variant having an IF of ≥1.2 for a measure of stability and an IF of ≥1.0 for a measure of specific activity in Model A and/or Model X detergent compositions.

In one embodiment, the variant comprises a substitution one or more positions selected from the group consisting of; H1, D3, G7, N16, V17, Q22, H28, N33, N36, T40, W48, S52, Q53, N54, D55, V56, G59, A60, V75, R76, N95, V99, G109, A111, D112, F113, T114, R116, V117, Q118, V122, N123, P124, N126, N128, V131, Q136, I137, E138, A139, T141, G142, F143, N144, F145, P146, G149, Q151, S153, S154, K156, Y160, T165, D166, Q169, S170, R171, Q172, A174, R176, R181, K185, A186, T193, N195, Y203, D205, V206, D209, E212, V213, N215, N218, W220, G221, N226, F233, K242, D248, L250, G251, H252, G258, N260, K269, G273, E276, N277, T285, P292, L293, H294, N296, Q299, S304, G305, N306, R310, N311, L312, Q319, R320, H321, T327, T334, P336, E338, E341, G346, W347, L351, A354, Y363, G373, I374, P375, S376, D377, V379, S381, Y382, Q384, P388, L389, L390, Q394, Q395, Y398, R400, H402, Y404, V410, E416, N418, A419, S420, P422, M430, S431, G435, Q445, A447, M454, F473, and N475; wherein the positions correspond to amino acid positions in the amino acid sequence set forth in SEQ ID NO: 3, which one or more substitutions provides an improvement factor of ≥1.5 for a measure of stability and optionally, an improvement factor of ≥1.0 for a measure of specific activity in Model A and/or Model X detergent compositions.

In one embodiment, the variant comprises one or more substitutions selected from the group consisting of; H1V, H1L, D3S, D3F, G7F, G7E, G7A, N16R, V17D, V17G, V17E, V17Q, V17A, V17T, V17L, Q22A, Q22Y, H28E, H28M, H28W, H28K, N33D, N36V, N36P, N36W, T40Q, T40S, W48C, W48I, W48H, W48A, S52M, S52V, S52C, S52F, S52A, S52D, S52K, S52N, S52E, S52T, Q53V, Q53L, Q53M, N54T, N54L, N54I, D55G, V56L, G59E, A60V, A60F, V75T, R76V, N95E, N95S, N95G, N95D, N95R, V99G, V99E, G109D, G109F, A111S, D112K, F113K, T114L, R116Q, R116K, V117G, V117I, V117M, Q118V, Q118G, Q118E, Q118F, Q118R, V122L, N123K, N123V, P124G, N126T, N128S, N128E, N128P, N128G, N128A, V131I, Q136E, Q136W, Q136G, I137V, E138T, E138L, A139S, A139G, A139V, A139T, A139P, T141S, T141G, G142R, G142A, F143L, N144G, N144R, F145A, F145N, F145Q, F145T, F145H, P146L, P146M, P146T, G149Y, G149L, G149A, Q151L, S153T, S154M, S154E, S154A, S154V, K156F, K156L, K156S, K156G, Y160H, T165I, D166S, Q169L, Q169S, Q169V, Q169F, S170A, S170V, S170Q, S170W, S170G, S170F, S170T, S170L, R171A, R171M, Q172L, Q172E, Q172C, Q172R, Q172G, Q172W, A174K, R176Y, R176M, R176T, R176K, K179L, R181A, R181G, R181D, K185G, A186S, A186D, A186T, A186Q, A186V, T193S, T193D, T193R, T193G, N195T, N195F, Y203W, Y203L, D205A, D205L, V206A, V206S, V206K, D209S, D209M, D209V, D209Q, D209L, D209I, E212G, E212I, E212C, E212K, V213W, V213R, V213F, N215C, N215T, N218D, N218R, N218L, N218M, W220L, W220I, W220P, W220E, W220R, W220A, W220S, G221A, N226C, N226M, N226E, N226K, N226R, F233T, F233P, F233M, K242A, D248G, D248R, L250Y, G251K, G251M, G251Q, H252F, H252V, G258D, N260W, N260R, K269W, G273E, E276L, N277D, T285M, T285P, P292L, P292G, L293G, L293Q, H294S, N296H, Q299L, Q299R, Q299P, S304G, S304L, S304F, S304A, S304M, G305F, G305I, N306V, N306L, N306D, N306S, N306T, R310T, N311C, N311Y, L312F, L312V, Q319H, Q319D, Q319F, R320V, H321R, H321S, T327V, T327E, T334S, P336L, P336W, P336S, P336K, E338A, E338H, E341M, E341F, E341K, E341S, G346S, W347L, W347R, W347V, W347C, L351H, L351Q, A354C, Y363R, Y363V, G373Q, G373W, G373R, I374Y, I374S, I374M, I374L, P375E, P375S, P375V, P375R, S376R, S376F, S376E, S376T, D377T, V379L, V379S, S381V, Y382R, Q384E, P388S, P388R, P388K, P388L, L389A, L389V, L389F, L389M, L390V, L390C, Q394N, Q394L, Q394T, Q394M, Q395R, Y398K, R400E, R400I, H402T, Y404F, Y404W, V410E, E416Q, N418M, N418G, N418R, N418F, A419M, A419L, A419Q, A419R, S420M, P422Y, P422H, P422D, P422R, M430L, S431A, S431F, G435S, Q445R, A447S, M454S, F473V, and N475G, wherein numbering is according to the amino acid sequence set forth in SEQ ID NO: 3, and wherein the one or more substitutions provides a variant having an IF of ≥1.5 for a measure of stability and optionally, an IF of ≥1.0 for a measure of specific activity in Model A and/or Model X detergent compositions.

In one embodiment, the variant comprises one or more substitutions selected from the group consisting of; H1V, G7F, G7E, Q22A, H28E, T40Q, W48C, W48I, S52M, S52V, Q53V, Q53L, V56L, G59E, V75T, N95E, N95S, N95G, R116Q, V117G, N128S, N128E, A139S, T141S, T141G, F143L, F145A, P146L, Q151L, K156F, K156L, K156S, K156G, T165I, D166S, Q169L, S170A, S170V, R171A, Q172L, Q172E, K179L, R181A, R181G, K185G, A186S, A186D, T193S, Y203W, Y203L, D209S, D209M, D209V, E212G, E212I, V213W, N215C, N226C, K242A, N260W, K269W, P292L, L293G, Q299L, Q299R, N306V, L312F, L312V, R320V, T327V, P336L, W347L, I374Y, S376R, V379L, S381V, L390V, Q395R, N418M, N418G, A419M, M430L, and S431A, wherein numbering is according to the amino acid sequence set forth in SEQ ID NO: 3, and wherein the one or more substitutions provides a variant having an IF of ≥1.5 for a measure of stability and an IF of ≥1.0 for a measure of specific activity in Model A and/or Model X detergent compositions.

In one embodiment, the variant comprises a substitution in one or more positions selected from the group consisting of; H1, H2, T5, G7, I9, Q11, E14, W15, N19, Q22, W24, N25, R26, H28, N29, N30, A31, L34, K35, I39, T40, A41, I42, I44, A47, W48, T51, S52, Q53, V56, G59, T74, V75, I89, R90, S91, L92, N95, I97, Q98, Y100, K108, F113, R116, V117, N126, N128, Q129, G133, A139, W140, T141, F143, F145, P146, Q151, K156, R158, H161, T165, D166, Q169, S170, R171, Q172, L173, A174, N175, K179, R181, G184, K185, A186, T193, Y203, D209, H210, E212, V213, N215, L217, N218, R219, V222, N226, T227, L228, K242, K245, L250, H252, V253, T257, G258, K259, N260, V264, K269, L279, K281, M286, P292, L293, Y295, L297, Q299, N306, L312, G315, T316, V318, R320, H321, S323, T327, V329, P336, G337, E341, S342, V344, Q345, G346, W347, P350, L351, Q361, Y363, Y368, I374, S376, V379, P380, S381, D387, L390, A392, Q395, H402, F405, T414, E416, N418, A419, M430, S431, G435, W439, K446, V450, G456, S459, N465, G476, and W482; wherein the positions correspond to amino acid positions in the amino acid sequence set forth in SEQ ID NO: 3, which one or more substitutions provides an improvement factor of ≥1.0 for a measure of stability and an improvement factor of ≥1.0 for a measure of specific activity in Model A detergent composition.

In a particular embodiment, the variant comprises one or more of the substitutions selected from the group consisting of; H1V, H2T, T5L, G7F, G7V, G7E, G7E, G7D, I9M, I9L, Q11L, Q11V, E14F, W15G, W15S, N19G, N19S, Q22C, Q22A, W24F, N25V, R26L, H28E, N29G, N29A, N30S, A31S, L34Y, K35L, I39L, T40Q, T40A, A41Q, I42V, I44T, A47G, W48C, W48I, W48Y, W48F, T51A, S52M, S52V, Q53V, Q53L, V56L, G59E, T74V, T74L, V75T, I89A, R90L, S91A, S91G, L92C, N95E, N95S, N95G, I97V, Q98V, Q98L, Y100W, K108V, F113M, F113V, F113E, F113Y, R116Q, V117G, N126G, N126A, N128S, N128E, Q129E, G133A, G133D, E138A, A139S, W140H, T141S, T141C, T141G, F143M, F143L, F145A, P146L, Q151L, K156F, K156Q, K156L, K156S, K156G, R158S, H161C, T165I, D166S, Q169L, S170A, S170V, R171A, Q172L, Q172E, L173I, A174V, N175G, K179L, R181A, R181G, G184D, K185G, A186S, A186D, T193S, Y203W, Y203L, D209S, D209M, D209V, H210N, E212G, E212I, V213C, V213W, N215C, L217S, N218S, R219L, V222E, N226C, T227L, L228F, K242A, F245G, L250C, H252C, V253A, V253L, T257V, G258P, K259L, N260W, N260G, V264L, K269W, L279Q, K281A, M286L, P292L, L293T, L293G, Y295F, L297W, Q299S, Q299L, Q299R, N306V, L312F, L312V, G315V, T316S, V318L, R320V, R320C, H321T, S323N, T327V, T327L, V329S, P336L, G337V, S342A, V344L, Q345L, G346R, W347L, P350S, P350Q, L351W, Q361V, Y363L, Y368H, Y372A, I374Y, S376R, S376L, V379L, P380V, S381V, D387Q, D387L, L390V, A392I, Q395E, Q395K, Q395R, H402L, F405L, T414A, E416V, N418M, N418G, A419M, M430L, S431A, G435N, W439E, W439R, W439N, K446G, V450T, G456Y, S459E, S459Q, N465L, N465R, D467C, G476Y, and W482F, wherein the numbering correspond to amino acid positions in the amino acid sequence set forth in SEQ ID NO: 3, and wherein the substitutions provides a variant having an IF of ≥1.0 for a measure of stability and an IF of ≥1.0 for a measure of specific activity in Model A detergent composition.

In one embodiment, the variant comprises a substitution in one or more positions selected from the group consisting of; H1, H2, T5, G7, I9, Q11, N19, Q22, W24, N25, R26, H28, N29, N30, A31, L34, K35, I39, T40, A41, I42, I44, A47, W48, T51, S52, Q53, V56, G59, T74, V75, T81, I89, R90, S91, L92, N95, I97, Q98, Y100, K108, F113, R116, V117, N126, N128, Q129, G133, E138, A139, W140, T141, F143, F145, P146, Q151, K156, R158, H161, T165, D166, Q169, S170, R171, Q172, L173, A174, N175, K179, R181, G184, K185, A186, T193, E194, Y203, D209, H210, E212, V213, N215, L217, N218, R219, V222, N226, T227, L228, K242, K245, L250, H252, V253, T257, G258, K259, N260, V264, K269, L279, K281, M286, P292, L293, Y295, L297, Q299, N306, L312, G315, T316, V318, R320, H321, S323, T327, V329, P336, G337, E341, S342, V344, Q345, G346, W347, P350, Q361, Y363, I374, S376, V379, P380, S381, D387, L390, A392, Q395, H402, F405, E416, N418, A419, S431, G435, W439, K446, V450, G456, S459, N465, D467, G476, and W482, wherein the positions correspond to amino acid positions in the amino acid sequence set forth in SEQ ID NO: 3, and wherein the one or more substitutions provide a variant having an IF of ≥1.0 for a measure of specific activity in Model X detergent composition and an IF of ≥1.0 for a measure of stability.

In one embodiment, the variant comprises one or more substitutions selected from the group consisting of; H1V, H2T, T5L, G7F, G7E, G7V, G7E, G7D, I9M, I9L, Q11L, Q11V, N19G, N19S, Q22C, Q22A, W24F, N25V, R26L, H28E, N29G, N29A, N30S, A31S, L34Y, K35L, I39L, T40A, T40Q, A41Q, I42V, I44T, A47G, W48C, W48I, W48Y, W48F, T51A, S52V, S52M, Q53L, Q53V, V56L, G59E, T74L, T74V, V75T, T81G, I89A, R90L, S91A, S91G, L92C, N95G, N95E, N95S, I97V, Q98V, Q98L, Y100W, K108V, F113M, F113V, F113E, F113Y, R116Q, V117G, N126G, N126A, N128S, N128E, Q129E, G133A, G133D, E138A, A139S, W140H, T141C, T141G, T141S, F143M, F143L, F145A, P146L, Q151L, K156Q, K156F, K156L, K156S, K156G, R158S, H161C, T165I, D166S, Q169L, S170A, S170V, R171A, Q172E, Q172L, L173I, A174V, N175G, K179L, R181A, R181G, G184D, K185G, A186S, A186D, A186H, T193S, Y203L, Y203W, D209S, D209M, D209V, H21 ON, E212G, E212I, V213C, V213W, N215C, L217S, N218S, R219L, V222E, N226C, T227L, L228F, K242A, F245G, L250C, H252C, V253A, V253L, T257V, G258P, K259L, N260W, V264L, K269W, L279Q, K281A, M286L, P292L, L293T, L293G, Y295F, L297W, Q299S, Q299L, Q299R, N306V, L312F, L312V, G315V, T316S, V318L, R320C, R320V, H321T, S323N, T327L, T327V, V329S, P336L, G337V, S342A, V344L, Q345L, G346R, W347L, P350S, P350Q, Q361V, Y363L, I374Y, S376R, S376L, V379L, P380V, S381V, D387Q, D387L, L390V, A392I, Q395E, Q395R, H402L, F405G, E416V, N418M, N418G, A419M, S431A, G435N, W439E, W439R, W439N, K446G, V450T, G456Y, S459Q, N465L, N465R, D467C, G476, and W482F wherein the positions correspond to amino acid positions in the amino acid sequence set forth in SEQ ID NO: 3, wherein the one or more substitutions provides a variant having an IF of ≥1.0 for a measure of specific activity in Model X detergent composition and an IF of ≥1.0 for a measure of stability.

In one embodiment, the variant comprises a substitution in one or more positions selected from the group consisting of; H1, G7, Q22, N25, R26, H28, N29, W48, S52, Q53, V56, G59, T74, V75, R90, N95, Q98, K108, F113, R116, V117, N128, Q129, G133, A139, W140, T141, F143, F145, P146, Q151, K156, T165, Q169, S170, R171, Q172, A174, K179, R181, K185, A186, T193, Y203, D209, E212, N215, L217, N226, K242, K259, N260, K269, K281, P292, L293, L297, N306, L312, G315, R320, H321, P336, V344, P350, Y363, Y368, S381, D387, A392, Q395, E416, N418, and S431; wherein the positions correspond to amino acid positions in the amino acid sequence set forth in SEQ ID NO: 3, which one or more substitutions provides an improvement factor of ≥1.3 for a measure of stability and an improvement factor of ≥1.3 for a measure of specific activity in Model A detergent composition.

In one embodiment, the variant comprises one or more substitutions selected from the group consisting of; H1V, G7F, G7V, G7E, G7E, Q22A, N25V, R26L, H28E, N29G, W48C, W48I, W48F, S52M, S52V, Q53V, Q53L, V56L, G59E, T74L, V75T, R90L, N95E, N95S, N95G, Q98V, Q98L, K108V, F113V, R116Q, V117G, N128S, N128E, Q129E, G133A, G133D, A139S, W140H, T141S, T141C, T141G, F143M, F143L, F145A, P146L, Q151L, K156F, K156Q, K156L, K156S, K156G, T165I, D166S, Q169L, S170A, S170V, R171A, Q172L, Q172E, A174V, K179L, R181A, R181G, K185G, A186S, A186D, T193S, Y203W, Y203L, D209S, D209M, D209V, E212I, N215C, L217S, N226C, K242A, K259L, N260W, K269W, K281A, P292L, L293T, L293G, L297W, N306V, L312F, L312V, G315V, R320V, H321T, P336L, V344L, P350Q, Y363L, Y368H, S381V, D387L, A392I, Q395K, Q395R, E416V, N418M, N418G, and S431A, wherein numbering is according to the amino acid sequence set forth in SEQ ID NO: 3, and wherein the one or more substitutions provides a variant having an IF of ≥1.3 for measure of stability and an IF of ≥1.3 for a measure of specific activity in Model A detergent composition.

In one embodiment, the variant comprises a substitution in one or more positions selected from the group consisting of; H1, T5, G7, Q22, N25, R26, N29, W48, S52, Q53, T74, R90, N95, Q98, K108, F113, R116, V117, N128, Q129, G133, A139, W140, T141, F143, F145, P146, Q151, K156, T165, D166, Q169, S170, R171, Q172, A174, K179, R181, K185, A186, Y203, E212, N215, N226, K242, N260, K269, L279, K281, L293, Q299, N306, L312, G315, R320, V344, P350, Y363, I374, V379, S381, D387, A392, Q395, E416, N418, and S431, wherein the positions correspond to amino acid positions in the amino acid sequence set forth in SEQ ID NO: 3, and wherein the substitution in the one or more positions provide a variant having an IF of ≥1.3 for a measure of specific activity in Model X detergent composition and an IF of ≥1.3 for a measure of stability.

In one embodiment, the variant comprises one or more substitutions selected from the group consisting of; H1V, T5L, G7F, G7E, G7V, G7E, Q22A, N25V, R26L, N29G, W48C, W48I, S52V, S52M, Q53L, Q53V, T74L, R90L, N95G, N95E, N95S, Q98V, Q98L, K108V, F113V, R116Q, V117G, N128S, N128E, Q129E, G133A, G133D, A139S, W140H, T141C, T141G, T141S, F143M, F145A, P146L, Q151L, K156Q, K156F, K156L, K156S, K156G, T165I, D166S, Q169L, S170A, S170V, R171A, Q172E, Q172L, A174V, K179L, R181A, R181G, K185G, A186S, A186D, Y203L, Y203W, E212G, E212I, N215C, N226C, K242A, N260W, K269W, L279Q, K281A, L293T, L293G, Q299S, Q299L, N306V, L312F, L312V, G315V, R320V, V344L, P350Q, Y363L, I374Y, V379L, S381V, D387L, A392I, Q395K, Q395R, E416V, N418M, N418G, and S431A, wherein the positions correspond to amino acid positions in the amino acid sequence set forth in SEQ ID NO: 3, and wherein the one or more substitutions provide a variant having an IF of ≥1.3 for a measure of specific activity in Model X detergent composition and an IF of ≥1.3 for a measure of stability.

In one embodiment, the variant comprises a substitution in one or more positions selected from the group consisting of; H1, G7, Q22, S52, Q53, G59, R116, V117, N128, A139, T141, F143, F145, P146, Q151, K156, T165, D166, Q169, S170, R171, R181, K185, A186, Y203, E212, N215, K242, K269, N306, L312, and N418, wherein numbering is according to the amino acid sequence set forth in SEQ ID NO: 3, and wherein the substitution in one or more positions provides a variant having an IF≥1.5 for a measure of specific activity in Model A detergent composition and an IF of ≥1.5 for a measure of stability.

In one embodiment, the variant comprises one or more substitution selected from the group consisting of; H1V, G7E, Q22A, S52V, Q53V, Q53L, G59E, R116Q, V117G, N128S, N128E, A139S, T141S, T141G, F143L, F145A, P146L, Q151L, K156F, K156L, K156S, K156G, T165I, D166S, Q169L, S170A, S170V, R171A, R181A, R181G, K185G, A186S, A186D, Y203W, Y203L, E212I, N215C, K242A, K269W, N306V, L312F, L312V, and N418G, wherein numbering is according to the amino acid sequence set forth in SEQ ID NO: 3, and wherein the substitution in one or more positions provides a variant having an IF≥1.5 for a measure of specific activity in Model A detergent composition and an IF of ≥1.5 for a measure of stability.

In one aspect the present invention relates to an alpha-amylase variant, wherein the variant is a mature form of an alpha-amylase having amylase activity and comprising a substitution at one or more positions selected from the group consisting of; E14, D20, Q22, G59, R116, A119, S132, G133, Y135, K156, R158, W159, Y160, K185, W187, Y202, D236, V238, K242, G337, E341, Y368, G369, D377, Y382, and K445; wherein the positions correspond to amino acids in the amino acid sequence set forth in SEQ ID NO: 3; and wherein the substitution provides at least one improved property selected from the group consisting of improved wash performance, improved detergent stability, and improved thermostability.

The term "thermostability" as used herein, refers to the ability of an enzyme to retain activity after exposure to an elevated temperature. The thermostability of an enzyme, such as an alpha-amylase or an alpha-amylase variant, is measure by its half-life ($t_{1/2}$) given in minutes, hours, or days, during which half the enzyme activity is lost under defined conditions. The half-life may be calculated by measuring residual alpha-amylase activity following exposure to (i.e. challenge by) an elevated temperature.

In another aspect, the present invention relates to an alpha-amylase variant, wherein the variant is a mature form of an alpha-amylase having amylase activity and comprising a substitution at one or more positions selected from the group consisting of; E14, D20, Q22, G59, R116, A119, S132, G133, Y135, K156, R158, W159, Y160, K185, W187, Y202, D236, V238, K242, G337, E341, Y368, G369, D377, Y382, and K445, wherein the positions correspond to amino acids in the amino acid sequence set forth in SEQ ID NO: 3; and wherein the substitution provides an alpha-amylase variant having an improvement factor of ≥1.0 for a measure of specific activity at pH 8.0 and 25° C., and an improvement factor of ≥1.0 for a measure of stability in a detergent composition and for thermostability.

In one embodiment, the variant comprises one or more substitutions selected from the group consisting of; D377V, W159D, K242E, R158Y, A119Y, D236P, R158E, Y135D, W187G, Y382L, R158V, G369I, G337M, K156G, W159E, Y160E, R158T, G59A, Y202S, K185V, S132D, Q22A, K156E, R116F, K185G, K242S, G133D, G369R, Y382E, D20R, Y368L, E341I, K445E, Y203V, V238W, and E14M, wherein the positions correspond to amino acid positions in the amino acid sequence set forth in SEQ ID NO: 3.

In one embodiment, the amino acid substituted with in the particular position is selected from the group consisting of A, C, D, E, F, G, H, I, K, L, M, N, P, Q, R, S, T, V, W, and Y, with the proviso that the amino acid substituted with is different from the naturally-occurring amino acid in said particular position.

The term "naturally-occurring amino acid" as used herein, refers to any amino acid from the group of A, C, D, E; F, G, H, I, K, L, M, N, P, Q, R, S, T, V, W, and Y, which is found in the parent alpha-amylase before any modification, e.g. in the wild-type amino acid sequence of the alpha-amylase.

In certain embodiments, the variant may comprise a pairwise deletion within a particular loop of the alpha-amylase which has been found to further stabilize the alpha-amylase. Thus, in one embodiment, the variant further comprises a pairwise deletion of the amino acid residues corresponding to R181, G182, D183 and G184 of the amino acid sequence set forth in SEQ ID NO: 3, with the proviso that when the amino acids in positions corresponding to R181 and/or G184 has been substituted, the pairwise deletion is in the positions corresponding to G182 and D183 of the amino acid sequence set forth in SEQ ID NO: 3.

The term "pairwise deletion" as used herein, refers to one deletion in two separate positions. Such positions may be adjacent to one another but are not limited to such adjacent pairs. A pairwise deletion may thus, also be deletion of one amino acid and another amino acid which may be up to three amino acids further downstream or upstream from the first deletion. Accordingly, in one embodiment, the variant comprises a pairwise deletion of the amino acids residues selected from the group consisting of; R181+G182, R181+D183, R181+G184, G182+D183, G182+G182, and D183+G184, wherein numbering is according to the amino acid sequence set forth in SEQ ID NO: 3.

In a particular embodiment, the pairwise deletion is in the positions corresponding to positions G182 and D183 of the amino acid sequence set forth in SEQ ID NO: 3.

In a further aspect, the present invention relates to an alpha-amylase variant, wherein said variant is a mature form having amylase activity and comprising a) a deletion and/or substitution at two or more positions corresponding to positions R181, G182, D183, and G184 of the amino acid sequence set forth in SEQ ID NO: 3; and b) a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3.

In one embodiment, the variant comprises a) a pairwise deletion of the amino acids residues selected from the group consisting of; R181+G182, R181+D183, R181+G184, G182+D183, G182+G182, and D183+G184, wherein numbering is according to the amino acid sequence set forth in SEQ ID NO: 3, and b) one or more substitutions selected from the group consisting of; H1V, H1L, H1G, H1S, H1C, H2T, H2L, H2M, H2E, H2P, H2G, D3R, D3Y, D3W, D3S, D3F, D3C, D3A, G4Q, G4D, G4R, T5L, T5F, T5W, T5Q, T5G, T5E, T5V, G7F, G7V, G7E, G7E, G7D, G7L, G7A, G7R, G7S, G7N, T8A, T8S, I9C, I9M, I9L, M10L, Q11C, Q11L, Q11V, Q11M, Y12V, Y12A, Y12F, F13Y, F13I, E14Q, E14L, E14M, E14S, E14F, W15G, W15S, W15I, W15F, W15H, N16R, N16G, N16Q, V17D, V17G, V17E, V17Q, V17A, V17T, V17L, P18L, N19G, N19S, N19Y, N19T, N19V, D20R, Q22C, Q22A, Q22Y, Q22N, Q22S, Q22M, Q22T, Q22E, H23W, W24H, W24F, N25V, N25R, N25L, N25T, N25S, N25G, N25E, N25E, R26L, R26E, R26G, R26D, R26M, R26I, R26S, R26W, R26A, R26F, L27A, L27M, H28A, H28E, H28R, H28M, H28W, H28K, H28I, N29G, N29K, N29V, N29W, N29C, N29L, N29A, N30S, N30R, N30H, N30L, N30T, N30E, A31W, A31S, A31G, A31R, A31V, Q32D, Q32G, Q32L, Q32A, N33F, N33A, N33R, N33D, L34F, L34Y, K35L, K35E, K35W, K35Q, N36R, N36Q, N36A, N36E, N36V, N36P, N36W, N36T, A37R, A37G, A37T, A37S, A37E, G38N, G38M, G38Y, G38K, I39M, I39L, I39V, T40D, T40E, T40Q, T40A, T40S, A41E, A41N, A41M, A41Q, A41 D, I42A, I42V, I42L, W43R, I44T, I44L, I44V, P45A, P46G, A47S, A47G, A47T, W48G, W48L, W48C, W48I, W48H, W48A, W48M, W48P, W48Q, W48Y, W48F, K49Q, G50P, G50S, G50N, T51S, T51G, T51P, T51L, T51C, T51A, S52M, S52V, S52C, S52F, S52A, S52D, S52K, S52N, S52E, S52T, S52I, S52L, Q53V, Q53L, Q53M, Q53G, N54G, N54K, N54V, N54T, N54L, N54I, N54S, D55G, D55V, D55I, V56L, V56M, V56T, G59E, G59S, G59A, A60V, A60F, A60S, A60W, A60L, A60G, A60T, Y61F, L63V, L63P, L63I, L63H, L63K, L63C, L63G, L63A, Y64W, Y64S, Y64V, Y64I, Y64H, Y64M, Y64C, Y64R, Y64G, Y64L, Y64A, L66M, E68D, E68S, E68M, E68C, E68T, E68V, E68Q, E68Y, F69H, F69W, N70G, N70A, N70T, N70S, N70E, Q71N, Q71E, Q71D, Q71I, Q71V, K72Y, K72R, G73V, G73C, G73L, G73E, T74V, T74L, T74N, V75T, V75E, V75G, R76S, R76G, R76A, R76V, T77A, T77S, T77V, K78L, K78T, K78A, T81W, T81L, T81G, K82A, K82G, A83G, A83E, A83Q, A83R, A83S, A83F, A83V, E84F, E84D, E84R, E84W, L85V, E86L, E86D, E86W, E86R, R87M, R87A, R87E, A88S, A88G, A88V, I89H, I89P, I89A, I89L, R90L, R90G, S91E, S91A, S91G, S91V, S91T, L92C, L92F, K93W, K93G, K93L, N95L, N95W, N95C, N95E, N95S, N95G, N95D, N95R, G96Q, G96R, I97M, I97V, I97L, Q98C, Q98M, Q98T, Q98V, Q98L, Q98F, Q98W, Q98P, Q98H, V99I, V99L, V99S, V99T, V99G, V99E, Y100V, Y100F, Y100W, V103G, V103A, V103S, V103T, H107Q, H107M, K108V, G109A, G109D, G109F, G109S, G110C, A111S, D112V, D112F, D112C, D112K, D112E, F113L, F113M, F113V, F113E, F113K, F113C, F113D, F113Q, F113Y, T114S, T114V, T114L, E115C, E115A, R116N, R116L, R116I, R116D, R116T, R116G, R116E, R116S, R116C, R116V, R116Q, R116K, R116F, R116H, R116W, V117C, V117L, V117S, V117W, V117A, V117G, V117I, V117M, V117E, Q118V, Q118G, Q118E, Q118F, Q118R, A119Y, A119W, V120I, V120D, V120L, V120C, V120A, V120N, E121P, E121G, E121V, E121M, E121D, V122E, V122P, V122L, V122I, V122F, N123G, N123A, N123E, N123W, N123T, N123P, N123K, N123V, P124R, P124G, Q125E, Q125T, N126E, N126G, N126A, N126R, N126T, R127R, R127S, R127C, R127W, R127L, R127V, R127F, R127Y, N128C, N128S, N128E, N128P, N128G, N128A, Q129L, Q129C, Q129E, E130C, V131L, V131E, V131I, S132A, S132H, S132P, S132C, S132E, S132D, A132Q, S132N, G133S, G133T, G133L, G133V, G133I, G133E, G133A, G133D, G133R, T134V, T134D, T134E, Y135L, Y135V, Y135S, Y135R, Y135T, Y135W, Y135K, Y135G, Y135P, Y135M, Y135D, Y135H, Y135F, Y135E, Q136E, Q136W, Q136G, I137A, I137S, I137G, I137V, E138A, E138Y, E138T, E138L, A139M, A139S, A139G, A139V, A139T, A139P, W140Y, W140S, W140A, W140H, T141M, T141S, T141C, T141G, G142D, G142E, G142R, G142A, F143M, F143L, F143I, N144C, N144M, N144K, N144G, N144R, F145C, F145S, F145A, F145N, F145Q, F145T, F145H, P146S, P146V, P146C, P146L, P146M, P146T, G147V, G147P, G147D, G147S, G147I, G147L, G147C, G149C, G149Y, G149L, G149A, N150C, N150D, N150E, Q151T, Q151C, Q151L, A151I, S153C, S153G, S153T, S154M, S154E, S154A, S154V, F155H, F155T, F155L, F155W, K156Y, K156V, K156A, K156D, K156W, K156P, K156E, K156C, K156F, K156Q, K156L, K156S, K156G, K156N, K156T, W157L, R158M, R158A, R158G, R158Q, R158W, R158L, R158T, R158V, R158E, R158Y, R158S, W159N, W159G, W159T, W159C, W159E, W159D, W159S, W159H, Y160Q, Y160M, Y160T, Y160A, Y160S, Y160V, Y160G, Y160I, Y160L, Y160E, Y160W, Y160R, Y160H, H161N, H161C, F162M, F162L, F162Y, F162I, D163S, D163K, D163A, D163R, D163L, G164S, G164T, G164C, T165L, T165M, T165S, T165G, T165I, T165V, T165E, D166T, D166N, D166S, W167Y, W167G, W167D, W167F D168M, D168S, D168G, Q169A, Q169L, Q169S, Q169V, Q169F, Q169E, S170A, S170V, S170Q, S170W, S170G, S170F, S170T, S170L, R171F, R171S, R171K, R171V, R171A, R171M, Q172S, Q172L, Q172E, Q172C, Q172R, Q172G, Q172W, Q172K, L173G, L173N, L173M, L173S, L173Y, L173V, L173I, L173A, L173F, A174G, A174V, A174L, A174M, A174K, A174S, N175L, N175V, N175I, N175G, N175S, R176E, R176W, R176G, R176M, R176Y, R176M, R176T, R176K, I177L, I177S, I177G, Y178V, Y178R, Y178K, Y178W, K179C, K179E, K179S, K179W, K179A, K179G, K179T, K179F, K179L, F180A, F180L, R181K, R181P, R181S, R181V, R181Q, R181E, R181A, R181G, R181D, G184L, G184R, G184V, G184T, G184D, K185A, K185D, K185N, K185V, K185G, A186C, A186S, A186D, A186T, A186Q, A186V, A186N, A186E, A186H, W187G, D188Q, D188G, D188R, D188M, D188L, D188V, W189R, W189A, W189G, W189C, E190D, E190N, E190A, V191M, V191A, D192E, D192Q, D192S, T193K, T193V, T193C, T193P, T193S, T193D, T193R, T193G, E194S, E194D, E194L, E194Q, N195R, N195A, N195T, N195F, G196A, G196V, G196P, N197G, N197V, N197Y, N197C, N197D, Y198W, Y198A, Y198G, D199G, D199S, D199A, Y200W, Y200F, Y200C, Y200V, Y200T, Y200L, Y200A, Y200G, Y200S, M202T, M202L, Y203F, Y203G, Y203C, Y203I, Y203Q, Y203H, Y203T, Y203M, Y203S, Y203V, Y203W, Y203L, A204P, A204R, A204C, A204H, A204W, A204F, A204L, A204Y, A204D, A204G, D205C, D205R, D205A, D205L, V206H, V206Q, V206P, V206A, V206S, V206K, V206L, V206I, V206M, V206F, V206Y, M208R, M208P, M208L, M208C, D209C, D209E, D209H, D209F, D209Y, D209S, D209M, D209V, D209Q, D209L, D209I, H210F, H210V, H210A, H210W, H210L, H210G, H210D, H210E, H210Q, H210N, P211G, P211W, P211C, E212F, E212M, E212D, E212G, E212I, E212Y, E212R, E212C, E212K, V213M, V213T, V213G, V213C, V213W, V213R, V213F, I214P, I214V, N215D, N215V, N215C, N215T, L217V, L217C, L217P, L217T, L217G, L217S, L217A, L217W, N218S, N218D, N218R, N218L, N218M, R219H, R219W, R219S, R219I, R219A, R219M, R219T, R219E, R219Y, R219D, R219C, R219L, W220L, W220I, W220P, W220E, W220R, W220A, W220S, G221S, G221A,
V222F, V222C, V222E, V222L, W223Y, W223F, W223L,
Y224L, A225K, N226Q, N226C, N226M, N226E, N226K,
N226R, T227S, T227M, T227C, T227L, T227Y, T227R,
L228A, L228F, L228M, N229T, N229S, L230S, L230A,
L230T, L230V, D231E, D231C, D231G, D231P, F233A,
F233L, F233T, F233P, F233M, V238C, V238W, V238A,
H240W, I241L, K242C, K242Y, K242P, K242W, K242G,
K242L, K242R, K242S, K242E, K242A, K242H, S244Q,
F245C, F245V, F245D, F245G, F245A, M246L, M246F,
M246V, M246I, R247Y, R247G, R247M, D248G, D248R,
W249L, W249F, L250W, L250T, L250A, L250C, L250F,
L250Y, G251K, G251M, G251Q, H252E, H252W, H252C,
H252T, H252F, H252V, V253S, V253W, V253A, V253L,
R254Q, R254S, G255C, G255E, G255L, Q256P, T257V,
G258V, G258C, G258I, G258L, G258P, G258F, G258D,
K259V, K259Q, K259I, K259L, K259A, K259S, K259D,
K259C, N260E, N260D, N260C, N260W, N260S, N260R,
N260G, L261G, L261D, L261T, F262Q, F262L, F262E,
F262R, F262P, F262V, A263L, A263C, V264T, V264L,
Y267V, Y267L, W268V, W268Y, K269L, K269W, K269Q,
K269R, N270D, N270A, N270M, N270G, D271E, D271V,
D271C, L272M, G273W, G273R, G273V, G273E, A274S,
A274D, A274E, L275G, L275E, L275A, L275R, L275K,
E276R, E276L, N277D, Y278G, Y278S, L279V, L279Q,
L279Q, L279M, S280C, S280R, S280E, S280D, K281L,
K281W, K281G, K281A, T282G, T282A, T282C, T282R,
T282I, N283G, N283E, N283Q, N283V, N283A, W284T,
W284I, W284S, W284E W284C, W284V, W284A, T285E,
T285F, T285S, T285W, T285M, T285P, M286D, M286L,
M286C, S287V, S287Q, S287T, S287E, S287P, S287L,
S287W, S287C, A288L, A288Y, A288V, V291T, P292A,
P292Q, P292R, P292L, P292G, L293A, L293E, L293T,
L293G, L293Y, L293Q, H294G, H294A, H294W, H294Q,
H294S, Y295H, Y295S, Y295I, Y295A, Y295F, N296A,
N296Y, N296M, N296F, N296S, N296K, N296H, L297S,
L297W, L297H, Y298V, Y298P, Q299I, Q299S, Q299L,
Q299R, Q299A, Q299H, Q299P, A300V, A300C, S301A,
S301R, S301Q, N302I, N302T, N302M, N302S, S303I,
S303E, S303A, S303M, S304I, S304P, S304G, S304L,
S304F, S304A, S304M, G305V, G305L, G305S, G305Q,
G305F, G305I, N306V, N306L, N306D, N306S, N306T,
Y307F, Y307W, M309L, R310A, R31 OT, N311L, N311R,
N311C, N311Y, L312F, L312V, L312I, L313S, L313M,
L313I, N314Y, N314F, N314D, G315I, G315V, G315T,
G315R, G315F, T316K, T316S, T316C, T316G, V318C,
V318E, V318A, V318L, Q319L, Q319I, Q319A, Q319P,
Q319H, Q319D, Q319F, R320L, R320V, R320C, R320A,
R320S, H321E, H321V, H321C, H321T, H321G, H321R,
H321S, P322E, P322C, S323N, A325V, A325S, V326I,
V326G, V326A, V326C, V326T, T327S, T327V, T327L,
T327Q, T327E, F328M, F328C, V329A, V329S, V329C,
V329I, N331C N331V, N331I, T334A, T334S, P336M,
P336E, P336D, P336R, P336L, P336W, P336S, P336K,
G337T, G337C, G337M, G337V, G337F, E338T, E338A,
E338H, E341C, E341D, E341I, E341P, E341M, E341F,
E341K, E341S, E341T, S342G, S342T, S342A, V344S,
V344L, Q345K, Q345C, Q345V, Q345I, Q345L, Q345W,
Q345N, G346H, G346A, G346L, G346N, G346Q, G346V,
G346R, G346S, W347L, W347R, W347V, W347C, F348Q,
F348S, F348C, F348P, F348M, K349G, K349A, K349Y,
K349L, K349S, P350L, P350G, P350S, P350Q, P350D,
P350E, L351M, L351S, L351W, L351H, L351Q, A352S,
A352C, A354C, T355V, T355A, T355L, T355Y, T355F,
L357C, L357T, L357S, L357H, T358V, T358F, T358S,
T358L, E360S, E360D, E360C, E360G, E360A, E360M,
Q361P, Q361R, Q361A, Q361E, Q361V, Q361G, Q361D, Q361S, G362Y, G362R, G362C, G362N, G362M, G362V,
Y363Q, Y363I, Y363A, Y363L, Y363R, Y363V, Q365D,
Q365M, Q365L, Q365T, Q365C, Q365S, V366L, V366A,
V366I, V366C, F367L, F367S, F367A, Y368M, Y368T,
Y368I, Y368L, Y368A, Y368S, Y368Q, Y368V, Y368H,
G369K, G369S, G369A, G369E, G369R, G369I, G369L,
D370A, D370T, Y372S, Y372I, Y372L, Y372G, Y372A,
G373C, G373S, G373T, G373Q, G373W, G373R, I374Y,
I374S, I374M, I374L, P375L, P375A, P375T, P375E,
P375S, P375V, P375R, S376A, S376N, S376P, S376W,
S376R, S376L, S376V, S376I, S376Q, S376F, S376E,
S376T, D377C, D377L, D377V, D377S, D377G, D377T,
V379F, V379P, V379L, V379S, P380L, P380G, P380E,
P380A, P380I, P380V, P380Y, S381N, S381L, S381A,
S381I, S381V, Y382I, Y382A, Y382E, Y382V, Y382L,
Y382K, Y382R, R383G, R383S, R383P, R383V, Q384A,
Q384P, Q384L, Q384H, Q384R, Q384Y, Q384S, Q384V,
Q384T, Q384G, Q384E, I386T, I386L, I386M, I386W,
I386V, D387H, D387V, D387Q, D387L, P388G, P388T,
P388M, P388W, P388V, P388S, P388R, P388K, P388L,
L389S, L389H, L389A, L389V, L389F, L389M, L390S,
L390F, L390I, L390G, L390V, L390T, L390N, L390H,
L390C, K391L, K391Y, K391A, K391Q, A392I, A392M,
A392T, Q394S, Q394R, Q394N, Q394L, Q394T, Q394M,
Q395W, Q395N, Q395L, Q395E, Q395K, Q395R, Q395V,
Q395S, Q395M, Y396T, Y396L, Y396R, Y396W, A397C,
A397G, A397S, Y398S, Y398C, Y398N, Y398K, R400L,
R400C, R400K, R400S, R400M, R400E, R400I, H402V,
H402E, H402M, H402A, H402S, H402P, H402Y, H402L,
H402D, H402R, H402T, D403E, D403P, D403Q, D403I,
Y404K, Y404F, Y404W, F405C, F405V, F405I, F405P,
F405W, F405G, F405A, D406E, D406V, D406T, D406M,
D406S, H407C, H407D, W408R, W408P, W408C, W408Y,
W408G, W408D, D409G, V410I, V410Q, V410L, V410E,
I411A, I411L, I411V, T414V, 414A, R415F, R415L, R415A,
R415Q, E416C, E416V, E416L, E416A, E416Q, N418L,
N418A, N418C, N418M, N418G, N418R, N418F, A419E,
A419C, A419M, A419G, A419V, A419L, A419Q, A419R,
S420E, S420T, S420V, S420M, H421V, H421C, H421A,
H421R, H421T, P422Y, P422V, P422H, P422D, P422R, S424C,
S424A, S424L, G425A, G425V, L426S, L426A, A427V,
A427S, T428L, T428N, T428A, T428G, I429V, I429A,
M430R, M430L, M430A, M430T, S431A, S431T, S431F,
D432Q, D432P, G435E, G435N, G435M, G435I, G435S,
G436M, G436E, G436L, G436T, S437G, S437Q, S437L,
K438T, W439C, W439H, W439E, W439A, W439R,
W439T, W439N, W439T, W439R, W439N, M440L,
Y441N, Y441H, Y441Q, Y441K, V442I, R444A, R444S,
R444L, R444V, R444P, Q445L, Q445S, Q445C, Q445E,
Q445R, K446Q, K446G, K446T, K446P, A447G, A447Q,
A447E, A447T, A447R, A447S, G448S, G448R, V450A,
V450T, V450Q, V450R, W451L, H452A, H452T, H452C,
H452G, H452Y, H452R, H452V, D453E, M454R, M454L,
M454V, M454Q, M454S, T455L, T455S, G456V, G456R,
G456Y, G456K, G456L, N457V, N457I, N457G, N457R,
S459V, S459C, S459P, S459M, S459T, S459E, S459Q,
S459R, G460S, G460D, G460E, T463C, T463V, T463L,
T463D, T463H, T463M, T463A, T463Q, I464V, N465G,
N465Q, N465L, N465R, Q466L, Q466C, Q466E, D467V,
D467C, W469M, W469E, W469T, W469N, H471Q, F473Y,
F473C, F473R, F473E, F473G, F473T, F473V, N475T,
N475H, N475G, G476F, G476K, G476Y, G477Q, G477F,
G477K, G477L, V481Q, V481S, and W482F, wherein the
numbering is according to the amino acid sequence set forth
in SEQ ID NO: 3.

The variants according to the present invention may further comprise one or more additional alterations than those described above at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide may be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In one embodiment, the variant comprises a modification in 1, 2, 3, 4, 5, 6, 7, 8, 9, 10, 11, 12, 13, 14, 15, 16, 17, 18, 19, or 20 positions.

In one embodiment, the variant comprises a substitution at 1, 2, 3, 4, 5, 6, 7, 8, 9, or 10 positions.

In any embodiment disclosed herein, the stability may be determined as described in Example [stability], and the specific activity may be determined as described in Example [spec. act.] when using Model A detergent composition or Model X detergent composition.

The variants according to the present invention may consist of 400 to 485 amino acids, e.g., 410 to 485, 425 to 485, and 440 to 485 amino acids.

Polynucleotides

The present invention also relates to polynucleotides encoding a variant of the present invention. Thus, in particular, the present invention relates to a polynucleotide encoding a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482, wherein the positions correspond to amino acid positions in the amino acid sequence set forth in SEQ ID NO: 3.

The term "polynucleotides encoding" as used herein, refers to a polynucleotide that encodes a mature polypeptide having alpha-amylase having alpha-amylase activity. In one aspect, the polypeptide coding sequence is the nucleotide sequence set forth in SEQ ID NO: 1.

In one embodiment, the polynucleotide encoding a variant according to the present invention as at least 80%, such as at least 85%, such as at least 90%, such as at least 95%, such as at least 96%, such as at least 97%, such as at least 98%, such as at least 99% but less than 100% sequence identity to the polynucleotide of SEQ ID NO: 1.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences. Thus, in particular, the present invention relates to a nucleic acid construct comprising a polypeptide encoding a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482 of the amino acid sequence set forth in SEQ ID NO: 3, wherein the polypeptide is operately linked to one or more control sequences.

The term "nucleic acid construct" as used herein, refers to a nucleic acid molecule, either single- or double-stranded, which is isolated from a naturally occurring gene or is modified to contain segments of nucleic acids in a manner that would not otherwise exist in nature or which is synthetic, which comprises one or more control sequences. A nucleic acid encompasses DNA, RNA, heteroduplexes, and synthetic molecules capable of encoding a polypeptide. Nucleic acids may be single stranded or double stranded, and may be chemical modifications. The terms "nucleic acids" and "polynucleotide" may be used interchangeably, but constitute the same meaning and purpose. Because the genetic code is degenerate, more than one codon may be used to encode a particular amino acid, and the present compositions and methods encompass nucleotide sequences which encode a particular amino acid sequence. Unless otherwise indicated by context, nucleic acids are written left to right in 5' to 3' orientation; amino acids sequences are written left to right in amino to carboxy orientation, respectively.

The term "operably linked" as used herein, refers to a configuration in which a control sequence is placed at an appropriate position relative to the coding sequence of a polynucleotide such that the control sequence directs expression of the coding sequence.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter comprises transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

The term "promoter" as used herein, refers to a regulatory sequence that is involved in binding RNA polymerase to initiate transcription of a gene, and may be an inducible promoter or a constitutive promoter. The skilled person would know of possible promoters that are suitable for the particular nucleic acid construct used.

Expression Vectors

The present invention also relates to recombinant expression vectors comprising a polynucleotide encoding a variant of the present invention, a promoter, and transcriptional and translational stop signals. Thus, the present invention relates to an expression vector, optionally recombinant, comprising a polynucleotide encoding a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482 of the amino acid sequence set forth in SEQ ID NO: 3, a promotor, and transcriptional and translational stop signals.

The term "expression vector" as used herein, refers to a linear or circular DNA molecule that comprises a polynucleotide encoding a variant and is operably linked to control sequences that provide for its expression.

The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

The skilled person would know which expression vector is the most suitable for specific expression systems. Thus, the present invention is not limited to any specific expression vector, but any expression vector comprising the polynucleotide encoding a variant according to the invention is considered part of the present invention.

Host Cells

The present invention also relates to recombinant host cells, comprising a polynucleotide encoding a variant of the present invention operably linked to one or more control sequences that direct the production of a variant of the present invention. Thus, the present invention relates to a host cell, optionally a recombinant host cell, comprising a polynucleotide encoding a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482 of the amino acid sequence set forth in SEQ ID NO: 3, operably linked to one or more control sequences that direct the production of the variant.

The term "host cell" as used herein, refers to any cell type that is susceptible to transformation, transfection, transduction, or the like with a nucleic acid construct or expression vector comprising a polynucleotide of the present invention. The term "host cell" encompasses any progeny of a parent host cell that is not identical to the parent host cell due to mutations that occur during replication.

A construct or vector comprising a polynucleotide is introduced into a host cell so that the construct or vector is maintained as a chromosomal integrant or as a self-replicating extrachromosomal vector as described earlier. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

Methods According to the Invention

The present invention also relates to methods of producing a variant, comprising: (a) cultivating a host cell of the present invention under conditions suitable for expression of the variant; and (b) recovering the variant. Thus, the present invention relates to a method of producing a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482 of the amino acid sequence set forth in SEQ ID NO:3, wherein the method comprises the steps of a) cultivating a host cell according to the invention under conditions suitable for expression of the variant, and b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the polypeptides having alpha amylase activity. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

In a particular embodiment, the method of producing a variant comprises the steps of a) introducing a deletion and/or substitution at two or more positions corresponding to positions 181, 182, 183, and 184 of the amino acid sequence set forth in SEQ ID NO: 3; and b) introducing a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3.

Furthermore, the present invention relates to methods for obtaining a variant, comprising introducing into a parent alpha-amylase having at least 80% sequence identity to the polypeptide of SEQ ID NO: 4:

(a) a substitution and/or deletion of two or more positions in the parent alpha-amylase said positions corresponding to positions 181, 182, 183, and 184 of the mature polypeptide of SEQ ID NO: 3; and (b) a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3, wherein the resulting variant has at least 80%, such as at least 85%, such as at least 90%, such as at least 95%, such as at least 97%, but less than 100% sequence identity with the mature polypeptide of SEQ ID NOs: 3 or 4, wherein said variant has alpha-amylase activity;

(c) recovering said variant.

The variants may be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent polypeptide and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure may be used in the present invention. There are many commercial kits available that can be used to prepare variants. The skilled person in the art is well-aware of such commercial kits and how to use them.

Synthetic gene construction entails in vitro synthesis of a designed polynucleotide molecule to encode a polypeptide of interest. Gene synthesis may be performed utilizing a number of techniques, such as the multiplex microchip-based technology described by Tian et al. (2004, *Nature* 432:

1050-1054) and similar technologies wherein oligonucle-otides are synthesized and assembled upon photo-program-mable microfluidic chips.

Single or multiple amino acid substitutions, deletions, and/or insertions may be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that may be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods may be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides may be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthe-sized, in combination with PCR techniques. Defined regions of genes may thus be synthesized de novo, while other regions may be amplified using site-specific mutagenic primers, while yet other regions may be subjected to error-prone PCR or non-error prone PCR amplification. Poly-nucleotide subsequences may then be shuffled.

The present invention also relates to a method of improv-ing performance, such as wash performance, of a parent alpha-amylase having the amino acid sequence of SEQ ID NO: 3 or 4, or having at least 65% sequence identity hereto, said method comprising the steps of a) introducing a pair-wise deletion and/or substitution at two or more positions corresponding to positions 181, 182, 183, and 184 of the amino acid sequence set forth in SEQ ID NO: 3; and b) introducing a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions cor-respond to amino acid positions in the amino acid sequence set forth in SEQ ID NO: 3; said method thereby providing an alpha-amylase variant of said parent alpha-amylase, wherein said variant has at least 65%, such as at least 70%, such as at least 75%, such as at least 80%, such as at least 85%, such as at least 90%, such as at least 95%, such as at least 97%, such as at least 99%, but less than 100%, sequence identity to the amino acid sequence as set forth in SEQ ID NOs: 3 or 4, and wherein said variant has alpha-amylase activity and improved performance as compared to said parent alpha-amylase, wherein the variant has at least 80%, at least 85%, at least 90%, at least 95%, at least 97%, at least 98%, at least 99%, but less than 100% sequence identity with the amino acid sequence set forth in SEQ ID NOs: 3 or 4, and wherein the variant has alpha-amylase activity and improved performance compared to the parent alpha-amylase.

In one embodiment, the variant has at least 50%, such as at least 60%, or at least 70%, or at least 80%, or at least 90%, or at least 100% of the activity of the parent polypeptide having the amino acid sequence of SEQ ID NO: 3.

In one embodiment, the activity is determined according to a Phadebas assay.

The alpha-amylase activity may be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The con-centration of blue is proportional to the alpha-amylase activity in the sample.

The variant sample to be analyzed is diluted in activity buffer with the desired pH. Two substrate tablets are sus-pended in 5 mL activity buffer and mixed on magnetic stirrer. During mixing of substrate transfer 150 µl to micro-titer plate (MTP) or PCR-MTP. Add 30 µl diluted amylase sample to 150 µl substrate and mix. Incubate for 15 minutes at 37° C. The reaction is stopped by adding 30 µl 1 M NaOH and mix. Centrifuge MTP for 5 minutes at 4000×g. Transfer 100 μl to new MTP and measure absorbance at 620 nm.

The alpha-amylase sample should be diluted so that the absorbance at 620 nm is between 0 and 2.2, and is within the linear range of the activity assay.

Thus, in one embodiment, the activity is determined by a method comprising the steps of:

a) incubating an alpha-amylase variant according to the invention with a dyed amylose substrate for 15 minute at 37° C.; and b) measuring the absorption at OD 620 nm.

In a further embodiment, the activity is determined by a method comprising the steps of:

a) incubating an alpha-amylase variant according to the invention with a dyed amylose substrate for 15 minute at 37° C.; and b) centrifuging the sample;

c) transferring the supernatant to reader plate, and d) measuring the absorption at OD 620 nm.

In another aspect, the present invention relates to a method of improving the stability, such as stability in a detergent composition and thermostability, of a parent alpha-amylase having the amino acid sequence of SEQ ID NO: 3 or 4, or having at least 65% sequence identity hereto, said method comprising the steps of a) introducing a pairwise deletion and/or substitution at two or more positions corresponding to positions 181, 182, 183, and 184 of the amino acid sequence set forth in SEQ ID NO: 3; and b) introducing a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3; said method thereby providing an alpha-amylase variant of said parent alpha-amylase, wherein said variant has at least 80%, such as at least 85%, such as at least 90%, such as at least 95%, such as at least 97%, such as at least 99%, but less than 100%, sequence identity to the amino acid sequence as set forth in SEQ ID NOs: 3 or 4, and wherein said variant has alpha-amylase activity and improved stability as compared to said parent alpha-amylase.

In one embodiment, the stability is determined according to a Phadebas assay.

In particular, the stability may be determined according to an assay comprising the steps of:

a) incubating the variant to be tested at 43° C. for 16 hrs in a detergent composition, such as Model A detergent composition, and another sample at 4° C. for 16 hrs, b) adding the sample comprising the variant to be tested to a substrate plate, c) measuring the absorbance at 620 nm, and d) calculating the % residual activity as the ratio between the sample incubated at 43° C. and the sample incubated at 4° C.

The stability may be determined by other methods known in the art.

In one embodiment, the variant has at least 50%, such as at least 60%, or at least 70%, or at least 80%, or at least 90%, or at least 100% of the activity of the parent alpha-amylase having the amino acid sequence of SEQ ID NO: 3 or 4.

Fermentation Broth Formulations or Cell Compositions

The present invention also relates to a fermentation broth formulation or a cell composition comprising a polypeptide of the present invention. Thus, in one embodiment, the fermentation broth formulation or the cell composition comprises a polynucleotide encoding a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3, a nucleic acid construct encoding a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3, or an expression vector encoding a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3. The fermentation broth product may further comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In one embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a particular embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one embodiment, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may comprise the unfractionated contents of the fermentation materials derived at the end of the fermentation. Typically, the cell-killed whole broth or composition comprises the spent culture medium and cell debris present after the microbial cells (e.g., filamentous fungal cells) are grown to saturation, incubated under carbon-limiting conditions to allow protein synthesis. In some embodiments, the cell-killed whole broth or composition comprises the spent cell culture medium, extracellular enzymes, and killed filamentous fungal cells. In some embodiments, the microbial cells present in the cell-killed whole broth or composition may be permeabilized and/or lysed using methods known in the art.

A whole broth or cell composition as described herein is typically a liquid, but may comprise insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a variant according to the invention. Thus, the invention relates to a composition comprising a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3.

In one embodiment, the composition comprises a variant comprising a) a deletion and/or a substitution at two or more positions corresponding to positions R181, G182, D183, and G184 of the amino acid sequence as set forth in SEQ ID NOs: 7 or 10, and b) a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96,I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3. Preferably, the compositions are enriched in such a variant. The term "enriched" as used herein, refers to that the alpha-amylase activity of the composition has been increased, e.g., with an enrichment factor of at least 1.1.

The compositions may comprise a variant of the present invention as the major enzymatic component, e.g., a mono-component composition. In another embodiment, the composition further comprises at least one further active component.

The term "active component" as used herein, refers to any biological or non-biological molecule which in itself is active. For example, an active component is an enzyme.

Thus, in one embodiment, the further active component is an enzyme, such as a protease, lipase, cellulose, pectate lyase and mannanase. Thus, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, lichenase, mannosidase, mutanase, oxidase, pectinolytic enzyme, peroxidase, phytase, polyphenoloxidase, proteolytic enzyme, ribonuclease, transglutaminase, or xylanase.

In one embodiment, the composition is a detergent composition, such as a liquid or powder detergent composition.

In one embodiment, the composition is a liquid laundry or liquid dish wash composition, such as an Automatic Dish Wash (ADW) liquid detergent composition, or a powder laundry, such as a soap bar, or powder dish wash composition, such as an ADW unit dose detergent composition.

The choice of additional components is within the skills of the skilled person in the art and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In one embodiment of the present invention, the variant of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor. The term "protein" in this context is contemplated to be understood to include a variant according to the present invention.

A composition for use in automatic dish wash (ADW), for example, may include 0.0001%-50%, such as 0.001%-20%, such as 0.01%-10%, such as 0.05-5% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The variants of the invention as well as the further active components, such as additional enzymes, may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. Such detergent compositions are all embodiments of the invention.

A variant of the present invention may also be incorporated in the detergent formulations disclosed in WO97/07202, which is hereby incorporated by reference.

Examples are given herein of preferred uses of the compositions of the present invention. The dosage of the composition and other conditions under which the composition is used may be determined on the basis of methods known in the art.

In particular, a composition according to the present invention further comprises a chelator.

The term "chelator" as used herein, refers to chemicals which form molecules with certain metal ions, inactivating the ions so that they cannot react with other elements. Thus, a chelator may be defined as a binding agent that suppresses chemical activity by forming chelates. Chelation is the formation or presence of two or more separate bindings between a ligand and a single central atom. The ligand may be any organic compound, a silicate or a phosphate. In the present context the term "chelating agents" comprises chelants, chelating agent, chelating agents, complexing agents, or sequestering agents that forms water-soluble complexes with metal ions such as calcium and magnesium. The chelate effect describes the enhanced affinity of chelating ligands for a metal ion compared to the affinity of a collection of similar nonchelating ligands for the same metal. Chelating agents having binding capacity with metal ions, in particular calcium (Ca2+) ions, and has been used widely in detergents and compositions in general for wash, such as laundry or dish wash. Chelating agents have however shown themselves to inhibit enzymatic activity. The term chelating agent is used in the present application interchangeably with "complexing agent" or "chelating agent" or "chelant".

Since most alpha-amylases are calcium sensitive the presence of chelating agents these may impair the enzyme activity. The calcium sensitivity of alpha-amylases can be determined by incubating a given alpha-amylase in the presence of a strong chelating agent and analyze the impact of this incubation on the activity of the alpha-amylase in question. A calcium sensitive alpha-amylase will lose a major part or all of its activity during the incubation. Chelating agent may be present in the composition in an amount from 0.0001 wt % to 20 wt %, preferably from 0.01 to 10 wt %, more preferably from 0.1 to 5 wt %.

Non-limiting examples of chelating agents are; EDTA, DTMPA, HEDP, and citrate. Thus, in one embodiment, the composition comprises a variant according to the invention and a chelating agent, such as EDTA, DTMPA, HEDP or citrate.

The term "EDTA" as used herein, refers to ethylene-diamine-tetra-acetic acid which falls under the definition of "strong chelating agents".

The term "DTMPA" as used herein, refers to diethylenetriamine penta(methylene phosphonic acid). DTMPA can inhibit the scale formation of carbonate, sulfate and phosphate.

The term "HEDP" as used herein, refers to hydroxyethane diphosphonic acid, which falls under the definition of "strong chelating agents".

The chelate effect or the chelating effect describes the enhanced affinity of chelating ligands for a metal ion compared to the affinity of a collection of similar nonchelating ligands for the same metal. However, the strength of this chelate effect can be determined by various types of assays or measure methods thereby differentiating or ranking the chelating agents according to their chelating effect (or strength).

In an assay the chelating agents may be characterized by their ability to reduce the concentration of free calcium ions ($Ca^{2+}$) from 2.0 mM to 0.10 mM or less at pH 8.0, e.g. by using a test based on the method described by M. K. Nagarajan et al., JAOCS, Vol. 61, no. 9 (September 1984), pp. 1475-1478.

For reference, a chelator having the same ability to reduce the concentration of free calcium ions ($Ca^{2+}$) from 2.0 mM to 0.10 mM at pH as EDTA at equal concentrations of the chelator are said to be strong chelators.

The composition of the present invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivatives thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polylactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients may be separated physically from each other by compartments in water dissolvable pouches or in different layers of tablets. Thereby negative storage interaction between components may be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Another form of composition is in the form of a soap bar, such as a laundry soap bar, and may be used for hand washing laundry, fabrics and/or textiles. The term "soap bar" as used herein, refers to includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term "solid" as used herein, refers to a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The soap bar may also comprise complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the soap bars by any single method. The premix of the invention may be added to the soap at different stages of the process. For example, the premix comprising a soap, an enzyme, optionally one or more additional enzymes, a protease inhibitor, and a salt of a monovalent cation and an organic anion may be prepared and the mixture may then plodded. The enzyme and optional additional enzymes may be added at the same time as an enzyme inhibitor, e.g. a protease inhibitor, for example in liquid form. Besides the mixing step and the plodding step, the process may further comprise the steps of milling, extruding, cutting, stamping, cooling and/or wrapping.

Uses

The present invention further relates to the use of a variant according to the present invention in a cleaning process such as laundry or hard surface cleaning including automated dish wash and industrial cleaning. The soils and stains that are important for cleaning are composed of many different substances, and a range of different enzymes, all with different substrate specificities, have been developed for use in detergents both in relation to laundry and hard surface cleaning, such as dishwashing. These enzymes are considered to provide an enzyme detergency benefit, since they specifically improve stain removal in the cleaning process that they are used in, compared to the same process without enzymes. Stain removing enzymes that are known in the art include enzymes such as proteases, amylases, lipases, cutinases, cellulases, endoglucanases, xyloglucanases, pectinases, pectin lyases, xanthanases, peroxidase, haloperoxygenases, catalases and mannanases.

In one embodiment, the invention relates the use of variants of the present invention in detergent compositions, for use in cleaning hard-surfaces, such as dish wash, or in laundering or for stain removal. In another embodiment, the invention relates to the use of an alpha-amylase variant according to the invention in a cleaning process such as laundry or hard surface cleaning including, but not limited to, dish wash and industrial cleaning. Thus, in one embodiment, the invention relates to the use of a variant comprising an alteration in one or more positions corresponding to the positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3 in a cleaning process such as laundry or hard surface cleaning including dish wash and industrial cleaning.

In a particular embodiment, the invention relates to the use of a variant comprising a) a substitution and/or deletion of two, three or four positions in the parent alpha-amylase said positions corresponding to positions R181, G182, D183, and G184 of the mature polypeptide of SEQ ID NO: 4; and b) a substitution in one or more positions corresponding to positions H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3, in a cleaning process such as laundry or hard surface cleaning including dish wash and industrial cleaning.

In one embodiment of the invention relates the use of a composition according to the invention comprising a variant of the present invention together with one or more surfactants and optionally one or more detergent components, selected from the list comprising of hydrotropes, builders and co-builders, bleaching systems, polymers, fabric hueing agents and adjunct materials, or any mixture thereof in detergent compositions and in detergent applications.

A further embodiment is the use of the composition according to the invention comprising a variant of the present invention together with one or more surfactants, and one or more additional enzymes selected from the group comprising of proteases, lipases, cutinases, cellulases, endoglucanases, xyloglucanases, pectinases, pectin lyases, xanthanases, peroxidase, haloperoxygenases, catalases and mannanases, or any mixture thereof in detergent compositions and in detergent applications.

In another aspect, the invention relates to a laundering process which may be for household laundering as well as industrial laundering. Furthermore, the invention relates to a process for the laundering of textiles (e.g. fabrics, garments, cloths etc.) where the process comprises treating the textile with a washing solution containing a detergent composition and an alpha-amylase of the present invention. The laundering can for example be carried out using a household or an industrial washing machine or be carried out by hand using a detergent composition containing a glucoamylase of the invention.

In another aspect, the invention relates to a dish wash process which may be for household dish wash as well as industrial dish wash. The term "dish wash" as used herein, refers to both manual dish wash and automated dish wash. Furthermore, the invention relates to a process for the washing of hard surfaces (e.g. cutlery such as knives, forks, spoons; crockery such as plates, glasses, bowls; and pans) where the process comprises treating the hard surface with a washing solution containing a detergent composition and an alpha-amylase variant of the present invention. The hard surface washing can for example be carried out using a household or an industrial dishwasher or be carried out by hand using a detergent composition containing an alpha-amylase of the invention, optionally together with one or more further enzymes selected from the group comprising of proteases, amylases, lipases, cutinases, cellulases, endoglucanases, xyloglucanases, pectinases, pectin lyases, xanthanases, peroxidase, haloperoxygenases, catalases, mannanases, or any mixture thereof.

In a further aspect, the invention relates to a method for removing a stain from a surface comprising contacting the surface with a composition comprising an alpha-amylase of the present invention together with one or more surfactants and optionally one or more detergent components selected from the list comprising of hydrotropes, builders and co-builders, bleaching systems, polymers, fabric hueing agents and adjunct materials, or any mixture thereof in detergent compositions and in detergent applications. A further aspect is a method for removing a stain from a surface comprising contacting the surface with a composition comprising an alpha-amylase variant of the present invention together with one or more surfactants, one or more additional enzymes selected from the group comprising of proteases, lipases, cutinases, cellulases, endoglucanases, xyloglucanases, pectinases, pectin lyases, xanthanases, peroxidase, haloperoxygenases, catalases and mannanases, or any mixture thereof in detergent compositions and in detergent applications.

The present invention is further described by the following examples that should not be construed as limiting the scope of the invention.

EXAMPLES

Example 1: Generation of Variants According to the Invention

The variants of the present invention have been generated by site-directed mutagenesis. Genomic DNA prepared from the organism containing amylase gene at the Pel locus was used as template for generating the site-directed mutants.

Mutagenic forward primer and PnMi4490 (CAATCCAAGAGAACCCTGATACGGATG—SEQ ID NO: 5) reverse primer was used to generate a ~3.8 kb fragment. This fragment was used as a megaprimer along with PnMi4491 (CGGAACGCCTGGCTGACAACACG—SEQ ID NO: 6) forward primer to get 6 kb insertion cassette. To enable integration in the Pel locus by double cross-over upon transformation, along with the amylase and cat genes, the cassette contained upstream and downstream Pel sequences at the ends. Selection was done on LB Agar containing chloramphenicol and the mutation was confirmed by DNA sequencing of amylase gene.

A library of variants were generated with a substitution in different positions selected from the following positions; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, K72, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, F113, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3.

TABLE 1

| Varients according to the invention | | | | |
|---|---|---|---|---|
| H1V | Q98T | Y178R | L275R | P375V |
| H1G | Q98F | Y178K | L275K | P375R |
| H1S | Q98W | Y178W | E276R | S376A |
| H1C | Q98P | K179L | E276L | S376N |
| H1L | Q98H | K179C | N277D | S376P |
| H2L | V99I | K179E | Y278G | S376R |
| H2T | V99L | K179S | Y278S | S376W |
| H2M | V99S | K179W | L279Q | S376L |
| H2E | V99T | K179A | L279V | S376V |
| H2P | V99G | K179G | L279G | S376I |
| H2G | V99E | K179T | L279M | S376Q |
| D3C | Y100W | K179F | S280C | S376F |

TABLE 1-continued

| Varients according to the invention | | | | |
|---|---|---|---|---|
| D3A | Y100V | F180A | S280R | S376E |
| D3R | Y100F | F180L | S280E | S376T |
| D3Y | V103G | R181K | S280D | D377C |
| D3W | V103A | R181P | K281L | D377L |
| D3S | V103S | R181S | K281A | D377V |
| D3F | V103T | R181A | K281W | D377S |
| G4Q | H107Q | R181V | K281G | D377G |
| G4D | H107M | R181Q | T282G | D377T |
| G4R | K108V | R181G | T282A | V379L |
| T5L | G109A | R181E | T282C | V379F |
| T5Q | G109S | R181D | T282R | V379P |
| T5G | G109D | G184L | T282I | V379S |
| T5E | G109F | G184R | N283G | P380L |
| T5V | G110C | G184V | N283E | P380V |
| T5F | A111S | G184T | N283Q | P380G |
| T5W | D112E | G184D | N283V | P380E |
| G7F | D112V | K185A | N283A | P380A |
| G7R | D112F | K185D | W284T | P380I |
| G7V | D112C | K185N | W284I | P380Y |
| G7E | D112K | K185G | W284S | S381N |
| G7E | F113M | K185V | W284E | S381V |
| G7D | F113V | A186N | W284C | S381L |
| G7L | F113L | A186E | W284V | S381A |
| G7A | F113C | A186S | W284A | S381I |
| G7S | F113E | A186C | T285E | Y382I |
| G7N | F113D | A186D | T285F | Y382A |
| T8A | F113K | A186T | T285S | Y382E |
| T8S | F113Q | A186Q | T285W | Y382V |
| I9C | F113Y | A186V | T285M | Y382L |
| I9M | T114S | A186H | T285P | Y382K |
| I9L | T114V | W187G | M286L | Y382R |
| M10L | T114L | D188Q | M286D | R383G |
| Q11C | E115C | D188G | M286C | R383S |
| Q11L | E115A | D188R | S287V | R383P |
| Q11V | R116N | D188M | S287Q | R383V |
| Q11M | R116L | D188L | S287T | R383Q |
| Y12V | R116I | D188V | S287E | Q384A |
| Y12A | R116Q | W189R | S287P | Q384P |
| Y12F | R116D | W189A | S287L | Q384L |
| F13Y | R116T | W189G | S287W | Q384H |
| F13I | R116G | W189C | S287C | Q384Y |
| E14L | R116E | E190D | A288L | Q384S |
| E14M | R116S | E190N | A288Y | Q384V |
| E14S | R116C | E190A | A288V | Q384T |
| E14Q | R116V | V191M | V291T | Q384G |
| E14F | R116F | V191A | P292A | Q384E |
| W15G | R116K | D192E | P292Q | I386T |
| W15F | R116H | D192Q | P292L | I386L |
| W15S | R116W | D192S | P292R | I386M |
| W15I | V117C | T193S | P292G | I386W |
| W15H | V117L | T193K | L293A | I386V |
| N16G | V117S | T193V | L293E | D387H |
| N16Q | V117W | T193C | L293T | D387Q |
| N16R | V117A | T193P | L293G | D387V |
| V17D | V117G | T193D | L293Y | D387L |
| V17G | V117E | T193R | L293Q | P388G |
| V17E | V117I | T193G | H294A | P388T |
| V17Q | V117M | E194S | H294W | P388M |
| V17A | Q118V | E194D | H294Q | P388W |
| V17T | Q118G | E194L | H294S | P388V |
| V17L | Q118E | E194Q | H294S | P388S |
| P18L | Q118F | N195R | Y295H | P388R |
| N19Y | Q118R | N195A | Y295S | P388K |
| N19T | A119Y | N195T | Y295I | P388L |
| N19G | A119W | N195F | Y295A | L389S |
| N19S | V120I | G196A | Y295F | L389H |
| N19V | V120D | G196V | N296A | L389A |
| D20R | V120L | G196P | N296Y | L389V |
| Q22N | V120C | N197G | N296M | L389F |
| Q22C | V120A | N197V | N296F | L389M |
| Q22S | V120N | N197Y | N296S | L390V |
| Q22M | E121P | N197C | N296K | L390S |
| Q22T | E121G | N197D | N296H | L390I |
| Q22E | E121V | Y198W | L297S | L390G |
| Q22A | E121M | Y198A | L297W | L390T |
| Q22Y | E121D | Y198G | L297H | L390F |
| H23W | V122E | D199G | Y298V | L390N |
| W24H | V122P | D199S | Y298P | L390H |

TABLE 1-continued

| Varients according to the invention | | | | |
|---|---|---|---|---|
| W24F | V122L | D199A | Q299S | L390C |
| N25V | V122I | Y200W | Q299L | K391L |
| N25S | V122F | Y200F | Q299R | K391Y |
| N25G | N123G | Y200C | Q299I | K391A |
| N25E | N123A | Y200V | Q299A | K391Q |
| N25E | N123E | Y200T | Q299H | A392I |
| N25R | N123W | Y200L | Q299P | A392M |
| N25L | N123T | Y200A | A300V | A392T |
| N25T | N123P | Y200G | A300C | Q394S |
| R26G | N123K | Y200S | S301A | Q394R |
| R26D | N123V | M202T | S301R | Q394N |
| R26M | P124R | M202L | S301Q | Q394L |
| R26I | P124G | Y203F | N302I | Q394T |
| R26S | Q125E | Y203G | N302T | Q394M |
| R26L | Q125T | Y203C | N302M | Q395W |
| R26W | N126E | Y203I | N302S | Q395E |
| R26A | N126G | Y203Q | S303I | Q395K |
| R26F | N126A | Y203H | S303E | Q395N |
| R26E | N126R | Y203W | S303A | Q395L |
| L27A | N126T | Y203T | S303M | Q395R |
| L27M | R127G | Y203L | S304I | Q395V |
| H28A | R127S | Y203M | S304P | Q395S |
| H28E | R127C | Y203S | S304G | Q395M |
| H28I | R127W | Y203V | S304L | Y396T |
| H28R | R127L | A204P | S304F | Y396L |
| H28M | R127V | A204R | S304A | Y396R |
| H28W | R127F | A204C | S304M | Y396W |
| H28K | R127Y | A204H | G305V | A397C |
| N29C | N128S | A204W | G305L | A397G |
| N29G | N128E | A204F | G305S | A397S |
| N29L | N128C | A204L | G305Q | Y398S |
| N29K | N128P | A204Y | G305F | Y398C |
| N29V | N128G | A204D | G305I | Y398N |
| N29W | N128A | A204G | N306V | Y398K |
| N29A | Q129L | D205C | N306L | R400L |
| N30S | Q129C | D205R | N306D | R400C |
| N30H | Q129E | D205A | N306S | R400K |
| N30L | E130C | D205L | N306T | R400S |
| N30T | V131L | V206H | Y307F | R400M |
| N30E | V131E | V206Q | Y307W | R400E |
| N30R | V131I | V206P | M309L | R400I |
| A31W | S132A | V206A | R310A | H402L |
| A31V | S132H | V206S | R310T | H402V |
| A31S | S132P | V206K | N311L | H402E |
| A31G | S132C | V206L | N311R | H402M |
| A31R | S132E | V206I | N311C | H402A |
| Q32D | S132D | V206M | N311Y | H402S |
| Q32G | S132V | V206F | L312P | H402P |
| Q32L | S132Q | V206Y | L312V | H402Y |
| Q32A | S132N | M208R | L312I | H402D |
| N33F | G133S | M208P | L313S | H402R |
| N33A | G133T | M208L | L313M | H402T |
| N33R | G133L | M208C | L313I | D403E |
| N33D | G133A | D209C | N314Y | D403P |
| L34F | G133V | D209S | N314F | D403Q |
| L34Y | G133I | D209M | N314C | D403I |
| K35L | G133E | D209E | G315I | Y404K |
| K35E | G133D | D209H | G315V | Y404F |
| K35W | G133R | D209F | G315T | Y404W |
| K35Q | T134V | D209Y | G315S | F405G |
| N36R | T134D | D209V | G315F | F405C |
| N36Q | T134E | D209Q | T316K | F405V |
| N36A | Y135L | D209L | T316S | F405I |
| N36E | Y135V | D209I | T316C | F405P |
| N36V | Y135S | H210V | T316G | F405W |
| N36P | Y135R | H210V | V318C | F405A |
| N36W | Y135T | H210A | V318L | D406E |
| N36T | Y135W | H210W | V318E | D406V |
| A37R | Y135K | H210L | V318A | D406F |
| A37G | Y135G | H210G | Q319L | D406M |
| A37T | Y135P | H210D | Q319I | D406S |
| A37S | Y135M | H210E | Q319A | H407C |
| A37E | Y135D | H210Q | Q319P | H407D |
| G38N | Y1315H | H210N | Q319H | W408R |
| G38M | Y135F | P211G | Q319D | W408P |
| G38Y | Y135E | P211W | Q319F | W408C |
| G38K | Q136E | P211C | R320V | W408Y |
| I39L | Q136W | E212G | R320L | W408G |

TABLE 1-continued

| Varients according to the invention | | | | |
|---|---|---|---|---|
| I39M | Q136G | E212F | R320C | W408D |
| I39V | I137A | E212M | R320A | D409R |
| T40Q | I137S | E212D | R320S | D409S |
| T40D | I137G | E212I | H321T | V410I |
| T40A | 1137V | E212Y | H321E | V410Q |
| T40E | E138A | E212R | H321V | V410L |
| T40S | E138Y | E212C | H321C | V410E |
| A41E | E138T | E212K | H321G | I411A |
| A41N | E138L | V213C | H321R | I411L |
| A41M | A139M | V213M | H321S | I411V |
| A41Q | A139S | V213T | P322E | T414A |
| A41D | A139G | V213G | P322C | T414V |
| I42V | A139V | V213W | S323N | R415F |
| I42A | A139T | V213R | A325V | R415L |
| I42L | A139P | V213F | A325S | R415A |
| W43R | W140Y | I214P | V326I | R415Q |
| I44T | W140S | 1214V | V326G | E416C |
| I44L | W140H | N215D | V326A | E416V |
| I44V | W140A | N215C | V326C | E416L |
| P45A | T141S | N215V | V326T | E416A |
| P46G | T141M | N215T | T327V | E416Q |
| A47S | T141C | L217V | T327L | N418L |
| A47G | T141G | L217C | T327S | N418M |
| A47T | G142D | L217P | T327Q | N418A |
| W48G | G142E | L217T | T327E | N418C |
| W48L | G142R | L217G | F328M | N418G |
| W48C | G142A | L217S | F328C | N418R |
| W48I | F143M | L217A | V329A | N418F |
| W48M | F143L | L217W | V329S | A419M |
| W48P | F143I | N218S | V329C | A419E |
| W48Q | N144C | N218D | V329I | A419C |
| W48H | N144M | N218R | N331C | A419V |
| W48A | N144K | N218L | N331V | A419L |
| W48Y | N144G | N218M | N331I | A419Q |
| W48F | N144R | R219L | T334A | A419R |
| K49Q | F145C | R219H | T334S | S420E |
| G50P | F145S | R219W | T334S | S420T |
| G50S | F145A | R219S | P336M | S420V |
| G50N | F145N | R219I | P336E | S420M |
| T51S | F145Q | R219A | P336D | H421V |
| T51G | F145T | R219M | P336L | H421C |
| T51P | F145H | R219T | P336R | H421A |
| T51L | P146S | R219E | P336W | H421R |
| T51C | P146L | R219Y | P336S | H421T |
| T51A | P146C | R219D | P336K | P422Y |
| S52M | P146M | R219C | G337T | P422H |
| S52V | P146T | W220L | G337C | P422D |
| S52I | G147V | W220I | G337V | P422R |
| S52L | G147P | W220P | G337M | S424C |
| S52C | G147D | W220E | G337F | S424A |
| S52F | G147S | W220R | E338T | S424L |
| S52A | G147I | W220A | E338A | G425A |
| S52D | G147L | W220S | E338H | G425V |
| S52K | G147C | G221S | E341C | L426S |
| S52N | G149C | G221A | E341D | L426A |
| S52E | G149Y | V222E | E341I | A427V |
| S52T | G149L | V222F | E341M | A427S |
| Q53G | G149A | V222C | E341F | T428L |
| Q53V | N150C | V222L | E341K | T428N |
| Q53L | N150D | W223Y | E341S | T428A |
| Q53M | N150E | W223F | E341T | T428G |
| N54G | Q151L | W223L | S342G | I429V |
| N54K | Q151T | Y224L | S342T | I429A |
| N54V | Q151C | A225K | S342A | M430L |
| N54T | Q151I | N226C | V344S | M430R |
| N54L | S153C | N226Q | V344L | M430A |
| N54I | S153G | N226M | Q345K | M430T |
| N54S | S153T | N226E | Q345C | S431A |
| D55V | S154M | N226K | Q345V | S431T |
| D55I | S154E | N226R | Q345L | S431F |
| D55G | S154A | T227S | Q345I | D432Q |
| V56L | S154V | T227L | Q345W | D432P |
| V56M | F155H | T227M | Q345N | G435E |
| V56T | F155T | T227C | G346H | G435M |
| G59E | F155L | T227Y | G346A | G435I |
| G59A | F155W | T227R | G346R | G435S |
| G59S | K156Y | L228A | G346L | G436M |
| A60S |  | L228F | G346N |  |

TABLE 1-continued

| Varients according to the invention | | | | |
|---|---|---|---|---|
| A60W | K156V | L228M | G346Q | G436E |
| A60L | K156A | N229T | G346V | G436L |
| A60G | K156F | N229S | G346S | G436T |
| A60V | K156D | L230S | W347L | S437G |
| A60F | K156Q | L230A | W347R | S437Q |
| A60T | K156L | L230T | W347V | S437L |
| Y61F | K156S | L230V | W347C | K438T |
| L63V | K156W | D231E | F348Q | W439E |
| L63P | K156P | D231C | F348S | W439C |
| L63I | K156E | D231G | F348C | W439H |
| L63H | K156C | D231P | F348P | W439A |
| L63K | K156G | F233A | F348M | W439R |
| L63C | K156N | F233L | K349G | W439T |
| L63G | K156T | F233T | K349A | W439N |
| L63A | W157L | F233P | K349Y | W439R |
| Y64W | R158M | F233M | K349L | W439N |
| Y64S | R158A | V238C | K349S | M440L |
| Y64V | R158G | V238W | P350S | Y441N |
| Y64I | R158Q | V238A | P350L | Y441H |
| Y64H | R158S | H240W | P350G | Y441Q |
| Y64M | R158W | I241L | P350Q | Y441K |
| Y64C | R158L | K242A | P350D | V442I |
| Y64R | R158T | K242C | P350E | R444A |
| Y64G | R158V | K242Y | L351W | R444S |
| Y64L | R158E | K242P | L351M | R444L |
| Y64A | R158Y | K242W | L351S | R444V |
| L66M | W159N | K242G | L351H | R444P |
| E68D | W159G | K242L | L351Q | Q445L |
| E68S | W159T | K242R | A352S | Q445S |
| E68M | W159C | K242S | A352C | Q445C |
| E68C | W159E | K242E | A354C | Q445E |
| E68T | W159D | K242Q | T355V | Q445R |
| E68V | W159S | K242H | T355A | K446G |
| E68Q | W159H | S244Q | T355L | K446Q |
| E68Y | Y160Q | F245C | T355Y | K446T |
| F69H | Y160M | F245V | T355F | K446P |
| F69W | Y160T | F245D | L357C | A447G |
| N70G | Y160A | F245G | L357T | A447Q |
| N70A | Y160S | F245A | L357S | A447E |
| N70T | Y160V | M246L | L357H | A447T |
| N70S | Y160G | M246F | T358V | A447R |
| N70E | Y160I | M246V | T358F | A447S |
| Q71N | Y160L | M246I | T358S | G448S |
| Q71E | Y160E | R247Y | T358L | G448R |
| Q71D | Y160W | R247G | E360S | V450T |
| Q71I | Y160R | R247M | E360D | V450A |
| Q71V | Y160H | D248G | E360C | V450Q |
| K72Y | H161C | D248R | E360G | V450R |
| K72R | H161N | W249L | E360A | W451L |
| G73V | F162M | W249F | E360M | H452A |
| G73L | F162L | L250C | Q361V | H452T |
| G73E | F162Y | L250W | Q361P | H452C |
| G73C | F162I | L250T | Q361R | H452G |
| T74V | D163S | L250A | Q361A | H452Y |
| T74L | D163K | L250F | Q361E | H452R |
| T74N | D163A | L250Y | Q361G | H452V |
| V75T | D163R | G251K | Q361D | D453E |
| V75G | D163L | G251M | Q361S | M454R |
| V75E | G164S | G251Q | G362Y | M454L |
| R76S | G164T | H252C | G362R | M454V |
| R76G | G164C | H252E | G362C | M454Q |
| R76A | T165L | H252W | G362N | M454S |
| R76V | T165M | H252T | G362M | T455L |
| T77A | T165S | H252F | G362V | T455S |
| T77S | T165G | H252V | Y363L | G456Y |
| T77V | T165I | V253A | Y363Q | G456V |
| K78L | T165V | V253L | Y363I | G456R |
| K78T | T165E | V253S | Y363A | G456K |
| K78A | D166T | V253W | Y363R | G456L |
| T81G | D166S | R254Q | Y363V | N457V |
| T81W | D166N | R254S | Q365D | N457I |
| T81L | W167Y | G255C | Q365M | N457G |
| K82A | W167G | G255E | Q365L | N457R |
| K82G | W167D | G255L | Q365T | S459E |
| A83G | W167F | Q256P | Q365C | S459Q |
| A83E | D168M | T257V | Q365S | S459V |
| A83Q | D168S | G258P | V366L | S459C |
| A83R | D168G | G258V | V366A | S459P |

TABLE 1-continued

| Varients according to the invention | | | | |
|---|---|---|---|---|
| A83S | Q169L | G258C | V366I | S459M |
| A83F | Q169A | G258I | V366C | S459T |
| A83V | Q169S | G258L | F367L | S459R |
| E84F | Q169V | G258F | F367S | G460S |
| E84D | Q169F | G258D | F367A | G460D |
| E84M | Q169E | K259L | Y368M | G460E |
| E84W | S170A | K259V | Y368T | G460E |
| L85V | S170V | K259Q | Y368H | T463C |
| E86L | S170Q | K259I | Y368I | T463V |
| E86D | S170W | K259A | Y368L | T463L |
| E86W | S170G | K259S | Y368A | T463D |
| E86R | S170F | K259D | Y368S | T463H |
| R87M | S170T | K259C | Y368Q | T463M |
| R87A | S170L | N260W | Y368V | T463A |
| R87E | R171F | N260E | G369K | T463Q |
| A88S | R171S | N260D | G369S | I464V |
| A88G | R171K | N260C | G369A | N465G |
| A88V | R171A | N260S | G369E | N465L |
| I89A | R171V | N260R | G369R | N465R |
| I89H | R171M | N260D | G369I | N465Q |
| I89P | Q172L | L261G | G369L | Q466L |
| I89L | Q172E | L261D | D370A | Q466C |
| R90L | Q172S | L261T | D370T | Q466E |
| R90G | Q172C | L261T | Y372A | D467C |
| S91A | Q172R | F262Q | Y372S | D467V |
| S91E | Q172G | F262L | Y372I | W469M |
| S91G | Q172W | F262E | Y372L | W469E |
| S91V | Q172K | F262P | Y372G | W469T |
| S91T | L173I | F262V | G373C | W469N |
| L92C | L173G | A263L | G373S | H471Q |
| L92F | L173M | A263C | G373T | F473Y |
| K93W | L173S | V264T | G373Q | F473C |
| K93G | L173Y | V264L | G373W | F473R |
| K93L | L173V | Y267V | G373R | F473E |
| N95L | L173L | Y267L | I374Y | F473G |
| N95E | L173A | W268V | I374S | F473T |
| N95W | L173F | W268Y | I374M | F473V |
| N95C | A174V | K269W | I374L | N475T |
| N95S | A174G | K269L | P375L | N475H |
| N95G | A174L | K269Q | P375A | N475G |
| N95D | A174M | K269R | P375T | G476F |
| N95R | A174K | N270D | P375E | G476Y |
| G96Q | A174S | N270A | P375S | G476K |
| G96R | N175L | N270M | | G477Q |
| I97M | N175V | N270G | | G477F |
| I97V | N175I | D271E | | G477K |
| I97L | N175G | D271V | | G477L |
| Q98V | N175S | D271C | | V481Q |
| Q98L | R176E | L272M | | V481S |
| Q98C | R176W | G273W | | W482F |
| Q98M | R176G | G273R | | |
| | R176V | G273V | | |
| | R176Y | G273E | | |
| | R176M | A274S | | |
| | R176T | A274D | | |
| | R176K | A274E | | |
| | I177L | L275G | | |
| | I177S | L275E | | |
| | I177G | L275A | | |
| | Y178V | | | |

Example 2: Specific Activity of Variants

In order to determine whether the variants generated as described and listed in Example 2 have a maintained or even improved activity, the variants were evaluated by the Phadebas assay. The following detergent compositions were prepared;

Preparation of Model X (0.175%):

1:2 molar ratio of CaCl2 and MgCl2 stock solution with 6000 dH (water hardness).

104.9 g of $CaCl_2 \cdot 2H_2O$ (0.713 M) was weighed into 1 liter bottle and to this 500 ml of type I water was added and stirred well. To this 72.5 g of $MgCl_2 \cdot 6H_2O$ (0.357 M) was

79 weighed and added, dissolved well and the final volume was made up to 1000 ml with type I water.

0.535 M Solution of NaHCO3

44.9 g of Sodium Hydrogen carbonate was dissolved in 100 ml of type I water.

Model X detergent with X Ionics with a Water Hardness of 12 (12° dH)

1.75 g of Model X detergent (as described above) was weighed and transferred into 1 litre bottle and to this 800 ml of type I water was added and mixed well. To this 35 mg of X-ionics was added and mixed well. To adjust the water hardness to 12° dH, 2 ml of 1:2 molar ratio of $CaCl_2$ and $MgCl_2$ stock solution with 6000° dH, 6 ml of 0.535 Molar solution of $NaHCO_3$ was added and mixed well. Finally the volume was made up to 1000 ml and the mixture was stirred for 10 min.

Preparation of Model A (0.33%):

4:1 Molar Ratio of CaCl2 and MgCl2 Stock Solution with 6000 dH (Water Hardness)

125.8 g of CaCl2·2H2O was weighed into 1 liter bottle and to this 500 ml of type I water was added and stirred well. To this 43.8 g of MgCl2·6H2O was weighed and added and dissolved well and the final volume was made up to 1000 ml with type I water.

0.535 M Solution of NaHCO3

44.9 g of Sodium Hydrogen carbonate was dissolved in 100 ml of type I water.

Model a Detergent with a Water Hardness of 15 (15° dH)

3.335 g of Model A detergent was weighed and transferred into 1 litre bottle and to this 865 ml of type I water was added and mixed well. To this 7.5 ml of 0.535 M $NaHCO_3$ was added, mixed well and made up the volume to 1 liter with type 1 water. To adjust the water hardness to 15° dH 2.5 ml of 4:1 molar ratio of $CaCl_2·2H_2O$ and $MgCl_2·6H_2O$ stock solution with 6000° dH was added and the mixture was stirred for 15 min.

Substrate: Phadebas Tablets (Magle Life Sciences)

1 tablet was suspended in 10 ml of the detergent solutions.

Buffer: 100 mM MOPS buffer pH 8

Experimental Procedure

Preparation of the Mother Plates:

Colonies were picked from the transformed plate by colony picker (KBiosystems) and inoculated in 96-well culture plate comprising TBGly media for growth. The cultures were grown for 3 days at 37° C. and the supernatant was recovered from the plates by centrifugation.

Preparation of the Substrate Plates:

The substrate solution was prepared by dissolving 1 tablet of phadebas in 10 ml of Model X/Model A detergent and 180 ul of the same was dispensed into 96 Well micro titer plate using multidrop instrument with constant stirring.

The culture supernatant was diluted to 100× with buffer and 20 ul of the diluted culture was added to the 180 ul of pre-dispensed substrate plate and mixed well. The plate was incubated for 20 min at 25° C. with shaking (900 rpm). After the incubation the plate was allowed to settle for 5 mins. 50 ul of the supernatant was transferred into 384 well plates and the absorbance was measured at 620 nm. The concentration of the expressed enzyme was determined by ELISA using specific antibodies. The specific activity was calculated by taking the ratio of the activity by concentration and the hits were identified as anything higher than the specific activity of the parent alpha-amylase. The Improvement Factor (IF) was calculated as: [Specific Activity of variant]/[Specific Activity of parent alpha-amylase].

80

TABLE 2

| The specific activity of the variants according to the invention obtained by the method described above are the following (amino acid substitutions refer to SEQ ID NO: 3); | | | | | |
|---|---|---|---|---|---|
| Substitution | Model A | Model X | Substitution | Model A | Model X |
| H1V | 1.5 | 1.3 | V206H | 1.3 | 1.2 |
| H1G | 1.5 | 1.4 | V206Q | 1.3 | 1.2 |
| H1S | 1.5 | 1.3 | V206P | 1.4 | 1.3 |
| H1C | 1.6 | 1.5 | M208R | 1.1 | 1.2 |
| H2L | 1.2 | 1.3 | M208P | 1.1 | 1.1 |
| H2T | 1.3 | 1.1 | M208L | 1.1 | 1.1 |
| H2M | 1.3 | 1.2 | M208C | 1.2 | 1.2 |
| H2E | 1.4 | 1.2 | D209C | 1.1 | 0.9 |
| H2P | 1.4 | 1.3 | D209S | 1.3 | 1.0 |
| H2G | 1.4 | 1.5 | D209M | 1.3 | 1.0 |
| D3C | 1.1 | 1.2 | D209E | 1.3 | 1.3 |
| D3A | 1.3 | 1.5 | D209H | 1.3 | 1.3 |
| G4Q | 1.3 | 1.3 | D209F | 1.3 | 0.8 |
| G4D | 1.4 | 1.4 | D209Y | 1.3 | 1.0 |
| G4R | 1.5 | | D209V | 1.4 | 1.1 |
| T5L | 1.1 | 1.3 | H210F | 0.5 | 1.6 |
| T5Q | 1.2 | 1.4 | H210V | 1.5 | 1.3 |
| T5G | 1.2 | 1.3 | H210A | 1.5 | 1.6 |
| T5E | 1.4 | 1.4 | H210W | 1.6 | 1.7 |
| T5V | 1.4 | 1.4 | H210L | 1.6 | 1.8 |
| G7F | 1.4 | 1.5 | H210G | 1.7 | 1.7 |
| G7R | 1.5 | 1.5 | H210D | 1.8 | 2.0 |
| G7V | 1.8 | 1.6 | H210E | 2.0 | 2.0 |
| G7E | 1.8 | 1.6 | P211G | 1.3 | 1.2 |
| G7E | 1.9 | 1.5 | P211W | 1.3 | 1.2 |
| G7D | 2.1 | 1.8 | P211C | 1.4 | 1.2 |
| T8A | 1.0 | 1.2 | E212G | 1.2 | 1.4 |
| T8S | 1.2 | 1.2 | E212F | 1.2 | 1.4 |
| I9C | 1.0 | 1.3 | E212M | 1.4 | 1.5 |
| I9M | 1.3 | 1.4 | E212D | 1.4 | 1.4 |
| I9L | 1.3 | 1.3 | E212I | 1.5 | 1.5 |
| M10L | 1.1 | 1.1 | V213C | 1.1 | 1.3 |
| Q11C | 1.1 | 1.3 | V213M | 1.1 | 1.2 |
| Q11L | 1.2 | 1.2 | V213T | 1.1 | 1.3 |
| Q11V | 1.5 | 1.4 | V213G | 1.1 | 1.1 |
| Y12V | 1.2 | 1.1 | V213W | 1.2 | 1.2 |
| Y12A | 1.3 | 1.3 | I214P | 1.3 | 1.2 |
| Y12F | 1.3 | 1.3 | N215D | 1.6 | 1.5 |
| F13Y | 1.4 | 1.3 | N215C | 1.7 | 1.4 |
| F13I | 1.7 | 1.6 | N215V | 1.7 | 1.6 |
| E14L | 1.9 | 1.0 | L217V | 1.1 | 1.3 |
| E14M | 2.0 | 1.4 | L217C | 1.3 | 1.4 |
| E14S | 2.0 | 1.2 | L217P | 1.4 | 1.4 |
| W15G | 1.5 | 0.5 | L217T | 1.5 | 1.3 |
| W15F | 1.6 | 1.1 | L217G | 1.5 | 1.3 |
| W15S | 2.0 | 0.5 | L217S | 1.7 | 1.2 |
| N16G | 1.5 | 1.4 | N218S | 1.1 | 1.2 |
| N16Q | 1.6 | 1.7 | R219L | 1.5 | 1.3 |
| P18L | 1.5 | 1.2 | R219H | 1.5 | 1.4 |
| N19Y | 1.5 | 1.4 | R219W | 1.5 | 1.3 |
| N19T | 1.5 | 1.6 | R219S | 1.5 | 1.3 |
| N19G | 1.6 | 1.6 | R219I | 1.5 | 1.5 |
| N19S | 1.7 | 1.6 | R219A | 1.5 | 1.3 |
| N19V | 1.7 | 1.6 | R219M | 1.5 | 1.4 |
| D20R | 2.1 | | R219T | 1.5 | 1.4 |
| Q22N | 1.3 | 1.4 | R219E | 1.5 | 1.4 |
| Q22C | 1.4 | 1.5 | R219Y | 1.7 | 1.6 |
| Q22S | 1.4 | 1.4 | R219D | 1.7 | 1.6 |
| Q22M | 1.5 | 1.4 | R219C | 1.7 | 1.6 |
| Q22T | 1.5 | 1.3 | V222E | 1.3 | 1.2 |
| Q22E | 1.5 | 1.3 | V222F | 1.3 | 1.2 |
| Q22A | 2.2 | 1.5 | V222C | 1.3 | 1.2 |
| W24H | 0.9 | 1.3 | W223Y | 1.7 | 1.6 |
| W24F | 1.3 | 1.5 | Y224L | 1.1 | 1.3 |
| N25V | 1.4 | 1.3 | A225K | 1.2 | 1.3 |
| N25S | 1.4 | 1.3 | N226C | 1.3 | 1.4 |
| N25G | 1.4 | 1.4 | N226Q | 1.4 | 1.5 |
| N25E | 1.4 | 1.5 | T227S | 1.2 | 1.2 |
| N25E | 1.5 | 1.4 | T227L | 1.2 | 1.2 |
| R26G | 1.5 | 1.5 | T227M | 1.2 | 1.1 |
| R26D | 1.5 | 1.4 | T227C | 1.2 | 1.2 |
| R26M | 1.5 | 1.3 | L228A | 1.2 | 1.2 |
| R26I | 1.5 | 1.4 | L228F | 1.3 | 1.2 |

81

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| R26S | 1.5 | 1.4 | N229T | 1.1 | 1.3 |
| R26L | 1.6 | 1.5 | N229S | 1.2 | 1.3 |
| R26W | 1.6 | 1.5 | L230S | 1.2 | 1.1 |
| R26A | 1.6 | 1.6 | L230A | 1.3 | 1.2 |
| R26F | 1.7 | 1.5 | L230T | 1.3 | 1.2 |
| L27A | 1.2 | 1.2 | L230V | 1.4 | 1.4 |
| L27M | 1.3 | 1.2 | D231E | 1.0 | |
| H28A | 1.2 | 1.3 | D231C | 1.0 | |
| H28E | 1.3 | 1.2 | D231G | 1.3 | |
| H28I | 1.3 | 1.3 | F233A | 1.3 | 1.3 |
| N29C | 1.3 | 1.3 | F233L | 1.3 | 1.3 |
| N29G | 1.6 | 1.7 | V238C | 1.7 | 1.5 |
| N29L | 1.6 | 1.5 | V238W | 2.1 | 2.0 |
| N30S | 1.2 | 1.3 | I241L | 1.5 | 1.4 |
| N30H | 1.3 | 1.2 | K242A | 1.5 | 1.7 |
| N30L | 1.4 | 1.3 | K242C | 1.5 | 1.5 |
| N30T | 1.4 | 1.2 | K242Y | 1.5 | 1.5 |
| N30E | 1.6 | 1.3 | K242P | 1.5 | 1.4 |
| A31W | 1.1 | 1.4 | K242W | 1.6 | 1.4 |
| A31V | 1.4 | 1.3 | K242G | 1.6 | 1.5 |
| A31S | 1.6 | 1.6 | K242L | 1.6 | 1.5 |
| Q32D | 1.4 | 1.3 | K242R | 1.8 | 1.9 |
| Q32G | 1.5 | 1.5 | K242S | 2.2 | 2.4 |
| Q32L | 1.6 | 1.5 | K242E | 2.9 | 3.2 |
| Q32A | 1.6 | 1.5 | F245C | 1.7 | 1.5 |
| N33F | 0.9 | 1.0 | F245V | 1.7 | 1.5 |
| N33A | 0.9 | 1.1 | F245D | 1.9 | 1.8 |
| N33R | 0.9 | 1.0 | F245G | 2.0 | 1.9 |
| L34F | 1.2 | 1.3 | M246L | 1.2 | 1.1 |
| L34Y | 1.4 | 1.4 | M246F | 1.2 | 0.8 |
| K35L | 1.3 | 1.1 | W249L | 1.3 | 1.3 |
| K35E | 1.3 | 1.1 | L250C | 1.1 | 1 |
| K35W | 1.3 | 1.0 | L250W | 1.1 | 1.1 |
| K35Q | 1.3 | 1.0 | L250T | 1.2 | 1.1 |
| N36R | 1.2 | 1.1 | L250A | 1.2 | 1.2 |
| N36Q | 1.3 | 1 | H252C | 1.2 | 1.2 |
| N36A | 1.3 | 1.3 | H252E | 1.2 | 1.3 |
| N36E | 1.3 | 1.4 | H252W | 1.2 | 1.1 |
| A37R | 1.0 | 1.3 | V253A | 1.1 | 1.1 |
| A37G | 1.1 | 1.4 | V253L | 1.1 | 1 |
| A37T | 1.3 | 1.3 | V253S | 1.1 | 0.9 |
| A37S | 1.3 | 1.2 | V253W | 1.1 | 1 |
| G38N | 1.0 | 1.1 | R254Q | 1.2 | 1.4 |
| I39L | 1.2 | 1.1 | R254S | 1.3 | 1.5 |
| I39M | 1.2 | 1.2 | G255C | 1.1 | 1 |
| T40Q | 1.1 | 1.1 | G255E | 1.2 | 1.2 |
| T40D | 1.1 | 1.0 | G255L | 1.2 | 1.1 |
| T40A | 1.2 | 1.0 | Q256P | 1.1 | 1.3 |
| T40E | 1.2 | 0.9 | T257V | 1.2 | 1.1 |
| A41E | 1.3 | 1.3 | G258P | 1.3 | 1.3 |
| A41N | 1.3 | 1.2 | G258V | 1.3 | 1.3 |
| A41M | 1.3 | 1.2 | G258C | 1.3 | 1.2 |
| A41Q | 1.4 | 1.4 | G258I | 1.3 | 1.3 |
| A41D | 1.4 | 1.3 | G258L | 1.9 | 1.9 |
| I42V | 1.1 | 1.3 | K259L | 1.3 | 1.2 |
| I42A | 1.1 | 1.2 | K259V | 1.3 | 1.2 |
| W43R | 1.2 | 1.3 | K259Q | 1.3 | 1.2 |
| I44T | 1.2 | 1.1 | K259I | 1.4 | 1.2 |
| P45A | 1.3 | 1.4 | N260W | 1.3 | 1.3 |
| P46G | 1.9 | 1.6 | N260E | 1.3 | 1.2 |
| A47S | 1.0 | 1.0 | N260D | 1.4 | 1.4 |
| A47G | 1.1 | 1.2 | N260C | 1.4 | 1.3 |
| W48G | 1.3 | 1.4 | L261G | 1.3 | 1.3 |
| W48L | 1.3 | 1.3 | L261D | 1.3 | 1.3 |
| W48C | 1.4 | 1.5 | F262Q | 1.5 | 1.8 |
| W48I | 1.4 | 1.4 | F262L | 1.5 | 1.5 |
| W48M | 1.4 | 1.4 | F262E | 1.6 | 1.6 |
| W48P | 1.4 | 1.4 | F262R | 1.6 | 1.6 |
| W48Q | 1.5 | 1.4 | F262P | 1.8 | 2.0 |
| G50P | 1.5 | 1.3 | F262V | 1.9 | 1.8 |
| G50S | 1.5 | 1.4 | A263L | 1.5 | 1.5 |
| G50N | 2.1 | 2.0 | A263C | 1.5 | 1.5 |
| T51S | 1.3 | 1.2 | V264T | 1.0 | 0.9 |

82

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| T51G | 1.7 | 1.8 | V264L | 1.1 | 1.1 |
| T51P | 1.8 | 1.2 | Y267V | 1.2 | 1.1 |
| T51L | 1.8 | 1.3 | Y267L | 1.3 | 1.1 |
| T51C | 1.9 | 1.8 | W268V | 1.2 | 0.7 |
| S52M | 1.4 | 1.3 | K269W | 1.5 | 1.5 |
| S52V | 1.6 | 1.4 | K269L | 1.8 | 1.6 |
| S52I | 1.7 | 1.7 | N270D | 1.6 | 1.6 |
| S52L | 1.8 | 1.7 | N270A | 1.6 | 1.4 |
| Q53G | 1.5 | 1.6 | N270M | 1.6 | 1.6 |
| Q53V | 1.6 | 1.7 | D271E | 1.1 | 1.3 |
| Q53L | 1.6 | 1.6 | D271V | 1.3 | 1.2 |
| N54G | 1.2 | 1.3 | D271C | 1.4 | 1.4 |
| N54K | 1.2 | 1.2 | G273W | 1.2 | 1.3 |
| N54V | 1.3 | 1.3 | G273R | 1.2 | 1.3 |
| D55V | 1.7 | 1.2 | G273V | 1.4 | 1.2 |
| D55I | 2.0 | 0.9 | A274S | 1.6 | 1.4 |
| V56L | 1.4 | 1.2 | A274D | 1.8 | 1.5 |
| V56M | 1.5 | 1.2 | A274E | 2.0 | 2.1 |
| G59E | 1.5 | 1.1 | E276R | 1.1 | 1.0 |
| G59A | 2.2 | 1.8 | Y278G | 1.2 | 1.1 |
| A60S | 1.5 | 1.6 | Y278S | 1.4 | 1.2 |
| A60W | 1.5 | 1.6 | L279Q | 1.2 | 1.4 |
| A60L | 1.7 | 1.5 | L279V | 1.3 | 1.3 |
| A60G | 2.0 | 1.9 | L279G | 1.4 | 1.6 |
| Y61F | 1.4 | 1.5 | S280C | 1.3 | 1.2 |
| L63V | 1.2 | 1.4 | K281L | 1.2 | 1.3 |
| L63P | 1.2 | 1.2 | K281A | 1.3 | 1.3 |
| L63I | 1.2 | 1.3 | K281W | 1.3 | 1.4 |
| L63H | 1.2 | 1.4 | K281G | 1.4 | 1.6 |
| L63K | 1.3 | 1.4 | T282G | 1.1 | 1.3 |
| Y64W | 1.5 | 1.5 | T282A | 1.1 | 1.3 |
| Y64S | 1.5 | 1.5 | T282C | 1.1 | 1.3 |
| Y64V | 1.6 | 1.6 | T282R | 1.2 | 1.3 |
| Y64I | 1.6 | 1.4 | T282I | 1.2 | 1.3 |
| Y64H | 1.6 | 1.5 | N283G | 1.0 | 1.3 |
| Y64M | 1.6 | 1.6 | N283E | 1.1 | 1.3 |
| Y64C | 1.7 | 1.6 | N283Q | 1.1 | 1.4 |
| Y64R | 1.7 | 1.6 | N283V | 1.2 | 1.4 |
| Y64G | 1.7 | 1.6 | N283A | 1.2 | 1.4 |
| Y64L | 1.7 | 1.6 | W284T | 1.1 | 1.3 |
| Y64A | 2.0 | 1.8 | W284I | 1.1 | 1.3 |
| L66M | 1.2 | 1.3 | W284S | 1.1 | 1.3 |
| E68D | 1.3 | 1.1 | W284E | 1.2 | 1.3 |
| F69H | 1.2 | 1.2 | W284C | 1.3 | 1.4 |
| F69W | 1.4 | 1.4 | W284V | 1.4 | 1.5 |
| N70G | 1.4 | 1.3 | W284A | 1.5 | 1.7 |
| N70A | 1.5 | 1.5 | T285E | 1.2 | 1.0 |
| N70T | 1.5 | 1.4 | T285F | 1.6 | 1.6 |
| N70S | 1.6 | 1.5 | T285S | 1.6 | 1.4 |
| N70E | 1.9 | 1.7 | M286L | 1.2 | 1.3 |
| Q71N | 1.4 | 1.4 | M286D | 1.3 | 1.1 |
| Q71E | 1.4 | 1.2 | S287V | 1.4 | 1.7 |
| Q71D | 1.5 | 1.5 | S287Q | 1.4 | 1.4 |
| Q71I | 1.7 | 1.4 | S287T | 1.4 | 1.3 |
| Q71V | 1.9 | 1.6 | S287E | 1.4 | 1.3 |
| K72Y | 1.5 | 1.4 | S287P | 1.4 | 1.5 |
| K72R | 2.0 | 1.9 | S287L | 1.5 | 1.5 |
| G73V | 1.4 | 1.4 | S287W | 1.6 | 1.7 |
| G73L | 1.6 | 1.7 | S287C | 1.8 | 1.6 |
| G73E | 1.6 | 1.6 | A288L | 1.2 | 1.1 |
| T74V | 1.6 | 1.3 | A288Y | 1.3 | 1.2 |
| T74L | 1.7 | 1.7 | V291T | 1.3 | 1.1 |
| V75T | 1.3 | 1.1 | P292A | 1.3 | 1.2 |
| V75V | 1.6 | 1.5 | P292Q | 1.3 | 1.2 |
| R76S | 1.3 | 1.1 | P292L | 1.3 | 1.2 |
| R76G | 1.4 | 1.3 | P292R | 1.5 | 1.5 |
| R76A | 1.5 | 1.5 | L293A | 1.0 | 1.2 |
| T77A | 1.1 | 1.0 | L293E | 1.2 | 1.2 |
| T77S | 1.5 | 1.5 | L293T | 1.3 | 1.3 |
| K78L | 1.5 | 1.3 | L293G | 1.3 | 1.4 |
| K78T | 1.6 | 1.3 | H294G | 1.3 | 1.1 |
| K78A | 1.6 | 1.3 | H294A | 1.3 | 1.3 |
| T81G | 0.9 | 1.1 | Y295H | 1.1 | 0.8 |

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| T81W | 1.0 | 1.1 | Y295S | 1.1 | 1.0 |
| T81L | 1.1 | 1.1 | N296A | 1.3 | 1.2 |
| K82A | 1.5 | 1.5 | N296Y | 1.4 | 1.3 |
| A83G | 1.3 | 1.3 | N296M | 1.6 | 1.4 |
| A83E | 1.4 | 1.3 | N296F | 1.6 | 1.4 |
| E84F | 1.1 | 1.0 | L297S | 1.2 | 1.1 |
| E84D | 1.2 | 1.1 | L297W | 1.4 | 1.2 |
| L85V | 1.2 | 1.0 | Y298V | 1.1 | 1.2 |
| E86L | 1.1 | 1.2 | Y298P | 1.1 | 1.2 |
| E86D | 1.1 | 1.1 | Q299S | 1.2 | 1.4 |
| R87M | 1.3 | 1.2 | Q299L | 1.2 | 1.3 |
| R87A | 1.4 | 1.4 | Q299R | 1.2 | 1.2 |
| R87E | 1.5 | 1.3 | Q299I | 1.5 | 1.7 |
| A88S | 1.1 | 1.1 | A300V | 1.2 | 1.2 |
| A88G | 1.1 | 1.1 | S301A | 1.1 | 1.0 |
| A88V | 1.2 | 1.3 | S301R | 1.2 | 1.2 |
| I89A | 1.4 | 1.4 | S301Q | 1.4 | 1.4 |
| I89H | 1.5 | 1.3 | N302I | 1.0 | 1.0 |
| I89P | 1.5 | 1.4 | N302T | 1.0 | 0.9 |
| R90L | 1.6 | 1.5 | N302M | 1.0 | 1.0 |
| R90G | 1.7 | 1.6 | S303I | 1.2 | 1.2 |
| S91A | 1.4 | 1.5 | S303E | 1.3 | 1.3 |
| S91E | 1.4 | 1.4 | S304I | 1.1 | 1.2 |
| S91G | 1.5 | 1.5 | S304P | 1.2 | 1.3 |
| L92C | 1.5 | 1.5 | G305V | 1.0 | 1.4 |
| K93W | 1.5 | 1.4 | G305L | 1.1 | 1.4 |
| K93G | 1.5 | 1.4 | G305S | 1.3 | 1.2 |
| K93L | 1.5 | 1.3 | N306V | 1.5 | 1.5 |
| N95L | 1.3 | 1.2 | Y307F | 1.0 | 1.0 |
| N95E | 1.4 | 1.3 | Y307W | 1.1 | 1.0 |
| N95W | 1.4 | 1.5 | M309L | 1.1 | 1.0 |
| N95C | 1.4 | 1.4 | L312F | 1.9 | 1.9 |
| N95S | 1.4 | 1.3 | L312V | 2.0 | 1.7 |
| N95G | 1.4 | 1.4 | L313S | 1.3 | 1.1 |
| G96Q | 1.2 | 1.2 | N314Y | 1.1 | 1.3 |
| I97M | 1.1 | 1.1 | N314F | 1.2 | 1.4 |
| I97V | 1.2 | 1.2 | N314D | 1.3 | 1.3 |
| Q98V | 1.3 | 1.3 | G315I | 1.2 | 1.5 |
| Q98L | 1.4 | 1.5 | G315V | 1.4 | 1.4 |
| Q98C | 1.4 | 1.5 | T316K | 1.1 | 0.9 |
| Q98M | 1.4 | 1.5 | T316S | 1.2 | 1.1 |
| Q98T | 1.5 | 1.5 | V318C | 1.2 | 1.1 |
| V99I | 1.3 | 1.3 | V318L | 1.3 | 1.2 |
| V99L | 1.3 | 1.3 | V318E | 1.4 | 1.3 |
| V99S | 1.4 | 1.4 | V318A | 1.7 | 1.5 |
| V99T | 1.4 | 1.4 | Q319L | 1.3 | 1.3 |
| Y100W | 1.5 | 1.4 | Q319I | 1.3 | 1.3 |
| Y100V | 1.5 | 1.5 | Q319A | 1.4 | 1.5 |
| Y100F | 1.6 | 1.5 | R320V | 1.3 | 1.3 |
| V103G | 1.2 | 1.3 | R320L | 1.3 | 1.4 |
| H107Q | 1.6 | 1.3 | R320C | 1.4 | 1.4 |
| K108V | 1.6 | 1.8 | H321T | 1.3 | 1.0 |
| G109A | 1.6 | 1.5 | H321E | 1.5 | 1.4 |
| G109S | 2.0 | 1.7 | H321V | 1.9 | 1.9 |
| D112E | 1.9 | 1.5 | H321C | 2.0 | 2.0 |
| F113M | 1.5 | 1.5 | P322E | 1.5 | 1.4 |
| F113V | 1.5 | 1.6 | P322C | 1.8 | 1.5 |
| F113L | 1.5 | 1.5 | A325V | 1.5 | 1.5 |
| F113C | 1.9 | 2.0 | A325S | 1.7 | 1.6 |
| F113E | 2.0 | 1.7 | V326I | 1.1 | 1.1 |
| F113D | 2.0 | 2 | T327V | 1.0 | 1.1 |
| E115C | 1.1 | 1.3 | T327L | 1.1 | 1.0 |
| E115A | 1.4 | 0.8 | T327S | 1.1 | 1.2 |
| R116N | 1.5 | 1.5 | V329A | 1.0 | 1.1 |
| R116L | 1.5 | 1.4 | V329S | 1.0 | 1.1 |
| R116I | 1.6 | 1.6 | N331C | 1.0 | 1.0 |
| R116Q | 1.7 | 1.7 | N331V | 1.1 | 1.0 |
| R116D | 1.7 | 1.8 | N331I | 1.1 | 1.0 |
| R116T | 1.7 | 1.7 | P336M | 1.3 | 1.2 |
| R116G | 1.7 | 1.7 | P336E | 1.4 | 1.2 |
| R116E | 1.8 | 1.7 | P336D | 1.4 | 1.2 |
| R116S | 1.8 | 2.0 | P336L | 1.4 | 1.2 |
| R116C | 1.8 | 1.8 | P336R | 1.4 | 1.1 |

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| R116V | 1.8 | 1.8 | G337T | 1.3 | 1.3 |
| R116F | 2.2 | 2.1 | G337C | 1.3 | 1.4 |
| V117C | 1.5 | 1.5 | G337V | 1.7 | 1.6 |
| V117L | 1.5 | 1.3 | G337M | 2.3 | 2.3 |
| V117S | 1.6 | 1.5 | E341C | 1.3 | 1.1 |
| V117W | 1.7 | 1.5 | E341D | 1.5 | 1.4 |
| V117A | 1.8 | 1.8 | E341I | 2.1 | 1.8 |
| V117G | 1.9 | 1.8 | S342G | 1.3 | 1.1 |
| V117E | 2.1 | 2.1 | S342T | 1.3 | 1.0 |
| A119Y | 2.7 | 3.1 | S342A | 1.9 | 1.6 |
| V120I | 1.1 | 1.3 | V344S | 1.2 | 1.2 |
| V120D | 1.2 | 1.4 | V344L | 1.4 | 1.4 |
| V120L | 1.4 | 1.5 | Q345K | 1.2 | 1.2 |
| E121P | 1.5 | 1.2 | Q345C | 1.2 | 1.5 |
| E121G | 1.6 | 1.3 | Q345V | 1.2 | 1.2 |
| E121V | 1.7 | 1.4 | Q345L | 1.3 | 1.1 |
| E121M | 1.7 | 1.4 | Q345I | 1.3 | 1.3 |
| E121D | 1.9 | 1.6 | G346H | 1.2 | 1.0 |
| V122E | 1.5 | 1.6 | G346A | 1.2 | 1.0 |
| V122P | 1.5 | 1.3 | G346R | 1.3 | 1.3 |
| N123G | 1.3 | 1.4 | G346L | 1.3 | 1.3 |
| N123A | 1.4 | 1.4 | G346N | 1.3 | 1.1 |
| N123E | 1.4 | 1.4 | G346Q | 1.3 | 1.4 |
| N123W | 1.4 | 1.4 | G346V | 1.4 | 1.5 |
| N123T | 1.5 | 1.6 | W347L | 1.2 | 1.0 |
| N123P | 1.6 | 1.4 | F348Q | 1.4 | 1.6 |
| Q125E | 1.2 | 1.2 | F348S | 1.4 | 1.6 |
| Q125T | 1.3 | 1.3 | F348C | 1.4 | 1.5 |
| N126E | 1.5 | 1.4 | K349G | 1.5 | 1.0 |
| N126G | 1.6 | 1.6 | K349A | 1.6 | 1.3 |
| N126A | 1.7 | 1.4 | K349Y | 1.7 | 1.2 |
| R127G | 1.5 | 1.5 | K349L | 1.7 | 1.6 |
| R127S | 1.5 | 1.5 | K349S | 2.3 | 1.9 |
| R127C | 1.6 | 1.5 | P350S | 1.4 | 1.4 |
| R127W | 1.7 | 1.6 | P350L | 1.4 | 1.6 |
| R127L | 1.7 | 1.6 | P350G | 1.6 | 1.6 |
| R127V | 1.7 | 1.5 | P350Q | 1.6 | 1.5 |
| R127F | 1.8 | 1.6 | L351W | 1.1 | 0.9 |
| R127Y | 1.9 | 1.8 | L351M | 1.3 | 1.3 |
| N128S | 1.5 | 1.4 | L351S | 1.4 | 1.3 |
| N128E | 1.6 | 1.5 | A352S | 1.2 | 1.1 |
| N128C | 1.6 | 1.5 | A352C | 1.3 | 1.3 |
| Q129L | 1.2 | 1.3 | T355V | 0.9 | 1.1 |
| Q129C | 1.4 | 1.3 | T355A | 1.1 | 1.1 |
| Q129E | 1.5 | 1.4 | L357C | 1.3 | 1.2 |
| E130C | 1.6 | 1.6 | L357T | 1.3 | 1.5 |
| V131L | 1.5 | 1.6 | L357S | 1.3 | 1.3 |
| V131E | 1.6 | 1.7 | T358V | 1.2 | 1.3 |
| S132A | 1.5 | 1.4 | T358F | 1.2 | 1.3 |
| S132H | 1.6 | 1.7 | T358S | 1.3 | |
| S132P | 1.7 | 1.6 | E360S | 0.9 | 1.1 |
| S132C | 1.7 | 1.6 | E360D | 1.0 | 1.2 |
| S132E | 1.9 | 1.8 | E360C | 1.1 | 1.4 |
| S132D | 2.2 | 2.1 | Q361V | 1.3 | 1.3 |
| G133S | 1.3 | 1.4 | Q361P | 1.3 | 1.3 |
| G133T | 1.3 | 1.2 | Q361R | 1.3 | 1.3 |
| G133L | 1.3 | 1.3 | Q361A | 1.4 | 1.4 |
| G133A | 1.4 | 1.3 | Q361E | 3.0 | 3.0 |
| G133V | 1.4 | 1.4 | G362Y | 1.5 | 1.3 |
| G133I | 1.4 | 1.4 | G362R | 1.6 | 1.7 |
| G133E | 1.8 | 1.8 | G362C | 1.6 | 1.5 |
| G133D | 2.2 | 1.8 | G362N | 1.6 | 1.5 |
| T134V | 1.5 | 1.6 | G362M | 1.7 | 1.5 |
| T134D | 1.7 | 1.7 | G362V | 1.9 | 1.6 |
| T134E | 1.7 | 1.8 | Y363L | 1.3 | 1.3 |
| Y135L | 1.5 | 1.3 | Y363Q | 1.4 | 1.3 |
| Y135V | 1.5 | 1.5 | Y363I | 1.4 | 1.4 |
| Y135S | 1.5 | 1.6 | Y363A | 1.5 | 1.5 |
| Y135R | 1.5 | 1.5 | Q365D | 1.2 | 1.3 |
| Y135T | 1.6 | 1.6 | V366L | 1.1 | 1.2 |
| Y135W | 1.7 | 1.8 | V366A | 1.2 | 1.2 |
| Y135K | 1.7 | 1.6 | Y368M | 1.3 | 1.3 |
| Y135G | 1.8 | 1.8 | Y368T | 1.3 | 1.1 |

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| Y135P | 1.9 | 1.6 | Y368H | 1.4 | 0.6 |
| Y135M | 2.0 | 2.1 | Y368I | 1.5 | 1.5 |
| Y135D | 2.5 | 2.6 | Y368L | 1.6 | 1.6 |
| I137A | 1.5 | 1.4 | Y368A | 1.6 | 0.7 |
| I137S | 1.8 | 1.6 | Y368S | 1.8 | 1.2 |
| I137G | 2.0 | 1.8 | Y368Q | 1.8 | 1.2 |
| E138A | 1.0 | 1 | Y368V | 2.1 | 2.1 |
| A139M | 1.5 | 1.3 | G369K | 1.7 | 0.6 |
| A139S | 1.6 | 1.5 | G369S | 1.7 | 0.7 |
| W140Y | 1.7 | 1.5 | G369A | 1.8 | 1.6 |
| W140S | 1.7 | 0.6 | G369E | 1.9 | 0.8 |
| W140H | 1.8 | 1.4 | G369R | 2.1 | 1.4 |
| W140A | 1.8 | 0.6 | G369I | 2.4 | 0.9 |
| T141S | 1.5 | 1.4 | D370A | 1.2 | 1.2 |
| T141M | 1.5 | 1.4 | D370T | 1.4 | 1.3 |
| T141C | 1.6 | 1.4 | Y372A | 1.1 | |
| T141G | 1.8 | 1.8 | Y372S | 1.3 | 1.3 |
| G142D | 1.5 | 1.6 | Y372I | 1.3 | 1.3 |
| G142E | 1.9 | 1.7 | Y372L | 1.4 | 1.4 |
| F143M | 1.5 | 1.4 | Y372G | 1.4 | 1.4 |
| F143L | 1.5 | 1.2 | G373C | 1.3 | 0.8 |
| N144C | 1.7 | 1.7 | G373S | 1.4 | 1.3 |
| F145C | 1.5 | 1.4 | I374Y | 1.2 | 1.4 |
| F145S | 1.6 | 1.3 | P375L | 1.2 | 1.3 |
| F145A | 1.7 | 1.5 | P375A | 1.2 | 1.3 |
| P146S | 1.5 | 1.3 | P375T | 1.2 | 1.4 |
| P146V | 1.5 | 1.3 | S376A | 1.1 | 1.0 |
| P146L | 1.6 | 1.6 | S376N | 1.1 | 1.0 |
| P146C | 1.8 | 1.6 | S376P | 1.2 | 1.1 |
| G147V | 1.5 | 1.4 | S376R | 1.2 | 1.1 |
| G147P | 1.5 | 1.5 | S376W | 1.3 | 1.2 |
| G147D | 1.5 | 1.5 | S376L | 1.4 | 1.5 |
| G147S | 1.5 | 1.7 | D377C | 1.2 | 1.0 |
| G147I | 1.6 | 1.5 | D377L | 1.5 | 1.2 |
| G147L | 1.6 | 1.6 | D377V | 3.2 | 2.0 |
| G147C | 1.7 | 1.4 | V379L | 1.2 | 1.4 |
| G149C | 1.7 | 1.8 | V379F | 1.3 | 1.4 |
| N150C | 1.5 | 1.4 | V379P | 1.5 | 1.6 |
| N150D | 1.6 | 1.6 | P380L | 1.2 | 1.2 |
| N150E | 1.8 | 1.7 | P380V | 1.3 | 1.3 |
| Q151L | 1.6 | 1.5 | P380G | 1.3 | 1.4 |
| Q151T | 1.6 | 1.4 | P380E | 1.3 | 1.3 |
| Q151C | 1.6 | 1.3 | P380A | 1.3 | 1.3 |
| S153C | 1.4 | 1.3 | P380I | 1.5 | 1.6 |
| F155H | 1.4 | 1.4 | S381N | 1.3 | 1.4 |
| F155T | 1.4 | 1.3 | S381V | 1.4 | 1.4 |
| F155L | 1.6 | 1.6 | S381L | 1.8 | 2.0 |
| K156Y | 1.5 | 1.6 | S381A | 2.1 | 2.2 |
| K156V | 1.6 | 1.5 | S381I | 2.4 | 2.7 |
| K156A | 1.6 | 1.6 | Y382I | 1.3 | 1.3 |
| K156F | 1.7 | 1.6 | Y382A | 1.4 | 1.3 |
| K156D | 1.7 | 1.7 | Y382E | 1.4 | 1.1 |
| K156Q | 1.9 | 1.7 | Y382V | 1.4 | 1.4 |
| K156L | 1.9 | 1.9 | Y382L | 1.5 | 1.3 |
| K156S | 1.9 | 1.7 | R383G | 1.2 | 1.3 |
| K156W | 1.9 | 1.9 | R383S | 1.3 | 1.2 |
| K156P | 1.9 | 1.9 | R383P | 1.3 | 1.0 |
| K156E | 2.0 | 1.8 | Q384A | 1.1 | 1.0 |
| K156C | 2.2 | 2.3 | Q384P | 1.1 | 1.2 |
| K156G | 2.3 | 2.2 | Q384L | 1.2 | 1.2 |
| W157L | 1.5 | 1.2 | Q384H | 1.3 | 1.3 |
| R158M | 1.5 | 1.4 | Q384R | 1.6 | 1.4 |
| R158A | 1.8 | 1.8 | Q384Y | 2.0 | 1.9 |
| R158G | 1.8 | 1.8 | I386T | 1.3 | 1.0 |
| R158Q | 1.9 | 1.9 | D387H | 1.3 | 1.2 |
| R158S | 2.0 | 1.9 | D387Q | 1.5 | 1.2 |
| R158W | 2.1 | 2.0 | D387V | 1.5 | 1.0 |
| R158L | 2.1 | 1.9 | D387L | 1.7 | 1.4 |
| R158T | 2.2 | 2.2 | P388G | 1.2 | 1.2 |
| R158V | 2.4 | 2.5 | P388T | 1.2 | 1.2 |
| R158E | 2.6 | 2.7 | P388M | 1.2 | 1.2 |
| R158Y | 2.9 | 2.0 | P388W | 1.3 | 1.4 |
| W159N | 1.5 | 1.5 | P388V | 1.3 | 1.3 |

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| W159G | 1.6 | 1.4 | L389S | 1.2 | 1.3 |
| W159T | 1.7 | 1.7 | L389H | 1.3 | 1.3 |
| W159C | 1.9 | 2.0 | L390V | 1.1 | 1.1 |
| W159E | 2.3 | 2.1 | L390S | 1.1 | 1.1 |
| W159D | 3.0 | 3.1 | L390F | 1.1 | 1.3 |
| Y160Q | 1.5 | 1.5 | L390I | 1.2 | 1.2 |
| Y160M | 1.5 | 1.3 | L390G | 1.2 | 1.2 |
| Y160T | 1.5 | 1.5 | K391L | 1.1 | 1.2 |
| Y160A | 1.5 | 1.3 | K391Y | 1.2 | 1.2 |
| Y160S | 1.7 | 1.7 | K391A | 1.2 | 1.2 |
| Y160V | 1.7 | 1.7 | A392I | 1.3 | 1.3 |
| Y160G | 1.7 | 1.5 | Q394S | 1.4 | 1.4 |
| Y160I | 1.7 | 1.6 | Q394R | 1.5 | 1.5 |
| Y160L | 1.8 | 1.7 | Q395W | 1.1 | 1.2 |
| Y160E | 2.2 | 2.0 | Q395E | 1.2 | 1.3 |
| H161C | 1.0 | 1.0 | Q395K | 1.3 | 1.3 |
| H161N | 1.0 | 1.0 | Q395N | 1.3 | 1.3 |
| F162M | 1.2 | 1.1 | Q395L | 1.3 | 1.0 |
| F162L | 1.3 | 1.1 | Q395R | 1.4 | 1.4 |
| F162Y | 1.3 | 1.3 | Y396T | 1.1 | 1.1 |
| F162I | 1.4 | 1.3 | Y396L | 1.2 | 1.1 |
| D163S | 1.1 | 1.4 | A397C | 1.3 | 1.3 |
| D163K | 1.4 | 1.4 | A397G | 1.5 | 1.5 |
| D163A | 1.4 | 1.3 | R400L | 1.5 | 1.2 |
| D163R | 1.4 | 1.1 | R400C | 1.5 | 1.3 |
| D163L | 1.7 | 1.7 | R400K | 1.5 | 1.3 |
| G164S | 1.5 | 1.1 | R400S | 1.5 | 1.3 |
| G164T | 1.7 | 1.1 | R400M | 1.6 | 1.4 |
| G164C | 1.7 | 1.1 | H402L | 1.2 | 1.4 |
| T165L | 1.4 | 1.3 | H402V | 1.2 | 1.3 |
| T165M | 1.4 | 1.4 | H402E | 1.3 | 1.2 |
| T165S | 1.4 | 1.3 | H402M | 1.3 | 1.3 |
| T165G | 1.6 | 1.5 | H402A | 1.3 | 1.3 |
| T165I | 1.8 | 1.6 | H402S | 1.4 | 1.4 |
| D166T | 1.7 | 1.3 | H402P | 1.5 | 1.5 |
| D166S | 1.8 | 1.4 | H402Y | 1.5 | 1.3 |
| D166N | 2.0 | 1.3 | D403E | 1.0 | 1.1 |
| W167Y | 1.4 | 1.5 | F405G | 1.2 | 1.2 |
| W167C | 1.4 | 1.3 | F405C | 1.2 | 1.1 |
| W167D | 2.0 | 1.7 | F405V | 1.2 | 1.2 |
| D168M | 1.3 | 1.5 | F405I | 1.3 | 1.2 |
| D168S | 1.3 | 1.4 | F405P | 1.3 | 1.2 |
| D168G | 1.5 | 1.6 | F405W | 1.3 | 1.2 |
| Q169L | 1.6 | 1.8 | D406E | 1.3 | 1.2 |
| Q169A | 1.6 | 0.0 | H407C | 1.3 | 1.3 |
| S170A | 1.5 | 1.3 | H407D | 1.5 | 1.2 |
| S170V | 1.7 | 1.3 | W408R | 1.4 | 1.2 |
| R171F | 1.5 | 1.4 | W408P | 1.5 | 1.4 |
| R171S | 1.5 | 1.4 | W408C | 1.5 | 1.4 |
| R171K | 1.5 | 1.5 | W408Y | 1.6 | 1.5 |
| R171A | 1.6 | 1.4 | W408G | 1.6 | 1.3 |
| R171V | 1.8 | 1.8 | W408D | 1.6 | 1.3 |
| Q172L | 1.3 | 1.3 | V410I | 1.3 | 1.3 |
| Q172E | 1.4 | 1.4 | V410Q | 1.4 | 1.7 |
| Q172S | 1.7 | 1.6 | I411A | 0.9 | 1.1 |
| L173I | 1.4 | 1.3 | I411L | 1.0 | 1.2 |
| L173G | 1.4 | 1.4 | I411V | 1.0 | 1.3 |
| L173N | 1.4 | 1.4 | T414A | 1.3 | 0.5 |
| L173M | 1.5 | 1.5 | T414V | 1.3 | 1.2 |
| L173S | 1.5 | 1.5 | R415F | 1.5 | 1.2 |
| L173Y | 1.5 | 1.4 | R415L | 1.6 | 1.4 |
| L173V | 1.7 | 1.6 | E416C | 1.2 | 1.2 |
| A174V | 1.4 | 1.3 | E416V | 1.3 | 1.3 |
| A174G | 1.4 | 1.4 | N418L | 1.2 | 1.3 |
| N175L | 1.3 | 1.6 | N418M | 1.4 | 1.3 |
| N175V | 1.4 | 1.6 | N418A | 1.4 | 1.3 |
| N175I | 1.5 | 1.7 | N418C | 1.5 | 1.4 |
| N175G | 1.5 | 1.7 | N418G | 1.9 | 1.8 |
| R176E | 1.4 | 1.4 | A419M | 1.2 | 1.2 |
| R176W | 1.4 | 1.3 | A419E | 1.3 | 1.1 |
| R176G | 1.5 | 1.5 | A419C | 1.3 | 1.2 |
| R176M | 1.6 | 1.5 | S420E | 1.1 | 1.0 |
| I177L | 1.4 | 1.3 | S420T | 1.1 | 1.0 |

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| I177S | 1.4 | 1.3 | S420V | 1.1 | 1.0 |
| I177G | 1.4 | 1.5 | H421V | 1.3 | 1.3 |
| Y178V | 1.5 | 1.4 | H421C | 1.4 | 1.3 |
| Y178R | 1.6 | 1.4 | H421A | 1.4 | 1.2 |
| Y178K | 2.0 | 1.7 | H421R | 1.5 | 1.4 |
| K179L | 1.4 | 1.5 | S424C | 1.1 | 0.9 |
| K179C | 1.6 | 1.5 | S424A | 1.1 | 1.1 |
| K179E | 1.6 | 1.5 | G425A | 1.3 | 1.4 |
| K179S | 1.7 | 1.5 | A427V | 1.2 | 1.1 |
| K179W | 1.7 | 1.5 | T428L | 1.0 | 0.9 |
| K179A | 1.8 | 1.7 | T428N | 1.1 | 1.1 |
| K179G | 1.8 | 1.6 | T428A | 1.1 | 1.1 |
| K179T | 1.8 | 1.7 | T428G | 1.2 | 1.2 |
| K179F | 1.9 | 1.6 | I429V | 1.2 | 1.1 |
| F180A | 1.3 | 1.3 | I429A | 1.2 | 1.2 |
| F180L | 1.4 | 1.4 | M430L | 1.1 | 0.9 |
| R181K | 1.4 | 1.4 | M430R | 1.3 | 1.1 |
| R181P | 1.4 | 1.5 | S431A | 1.4 | 1.4 |
| R181S | 1.4 | 1.5 | G435N | 1.7 | 1.5 |
| R181A | 1.5 | 1.5 | G435E | 2.0 | 1.7 |
| R181V | 1.6 | 1.7 | G436M | 1.3 | 1.4 |
| R181Q | 1.9 | 1.9 | G436E | 1.3 | 1.4 |
| R181G | 2.0 | 1.9 | G436L | 1.3 | 1.3 |
| R181E | 2.0 | 1.9 | G436T | 1.4 | 1.4 |
| G184L | 1.2 | 1.0 | S437G | 1.1 | 1.1 |
| G184R | 1.4 | 1.3 | S437Q | 1.2 | 1.3 |
| G184V | 1.4 | 1.4 | S437L | 1.2 | 1.3 |
| K185A | 1.9 | 1.7 | K438T | 1.1 | 1.1 |
| K185D | 2.0 | 1.9 | W439E | 1.3 | 1.2 |
| K185N | 2.0 | 1.7 | W439C | 1.3 | 1.3 |
| K185G | 2.2 | 1.9 | W439H | 1.3 | 1.4 |
| K185V | 2.2 | 1.8 | M440L | 1.4 | 1.2 |
| A186S | 1.5 | 1.6 | Y441N | 1.0 | 1.0 |
| A186C | 1.5 | 1.5 | Y441H | 1.0 | 1.0 |
| A186D | 1.6 | 1.5 | Y441Q | 1.0 | 1.0 |
| W187G | 2.4 | 1.6 | V442I | 1.2 | 1.2 |
| D188Q | 1.4 | 1.4 | R444A | 1.3 | 1.2 |
| D188G | 1.4 | 1.4 | R444S | 1.3 | 1.2 |
| D188R | 1.4 | 1.3 | R444L | 1.3 | 1.1 |
| D188M | 1.6 | 1.5 | R444V | 1.4 | 1.4 |
| D188L | 1.6 | 1.4 | R444P | 1.5 | 1.3 |
| D188V | 1.8 | 1.6 | Q445L | 1.2 | 1.3 |
| W189R | 1.6 | 0.9 | Q445S | 1.3 | 1.3 |
| W189A | 1.6 | 1.0 | Q445C | 1.4 | 1.5 |
| W189G | 1.7 | 0.9 | Q445E | 2.1 | 2.0 |
| W189C | 1.8 | 1.1 | K446G | 1.0 | 1.0 |
| E190D | 1.3 | 1.0 | K446Q | 1.0 | 1.0 |
| E190N | 1.3 | 1.0 | A447G | 1.3 | 1.3 |
| E190A | 1.3 | 1.2 | A447Q | 1.3 | 1.3 |
| V191M | 1.6 | 1.3 | A447E | 1.4 | 1.5 |
| V191A | 1.6 | 1.1 | A447T | 1.5 | 1.4 |
| D192E | 1.1 | 1.0 | G448S | 1.3 | 1.2 |
| D192Q | 1.2 | 1.0 | V450T | 1.1 | 1.1 |
| D192S | 1.2 | 1.0 | V450A | 1.1 | 1.1 |
| T193S | 1.3 | 1.1 | H452A | 1.2 | 1.2 |
| T193K | 1.3 | 1.2 | H452T | 1.2 | 1.1 |
| T193V | 1.3 | 1.2 | D453E | 1.1 | 1.0 |
| T193C | 1.4 | 1.2 | M454R | 1.2 | 1.2 |
| T193P | 1.4 | 1.3 | M454L | 1.2 | 1.0 |
| E194S | 1.1 | 1.0 | M454V | 1.6 | 1.1 |
| E194D | 1.2 | 1.0 | T455L | 1.1 | 1.0 |
| E194L | 1.3 | 1.0 | T455S | 1.2 | 1.1 |
| E194Q | 1.9 | 1.6 | G456Y | 1.2 | 1.2 |
| N195R | 1.3 | 1.1 | G456V | 1.2 | 1.2 |
| N195A | 1.3 | 1.1 | G456R | 1.5 | 1.6 |
| G196A | 1.3 | 1.2 | N457V | 1.1 | 1.2 |
| G196V | 1.3 | 1.1 | N457I | 1.1 | 1.2 |
| N197G | 1.3 | 1.1 | N457G | 1.1 | 1.1 |
| N197V | 1.3 | 1.2 | N457R | 1.2 | 1.2 |
| N197Y | 1.3 | 1.2 | S459E | 1.2 | 0.1 |
| N197C | 1.4 | 1.2 | S459Q | 1.2 | 1.2 |
| N197D | 1.4 | 1.2 | S459V | 1.2 | 1.2 |
| Y198W | 1.2 | 1.1 | S459C | 1.2 | 1.1 |

TABLE 2-continued

The specific activity of the variants according to the invention
obtained by the method described above are the following
(amino acid substitutions refer to SEQ ID NO: 3);

| Substitution | Model A | Model X | Substitution | Model A | Model X |
|---|---|---|---|---|---|
| D199G | 1.5 | 1.5 | S459P | 1.2 | 1.1 |
| D199S | 1.6 | 1.5 | S459M | 1.3 | 1.3 |
| D199A | 1.7 | 1.5 | S459T | 1.5 | 1.5 |
| Y200W | 1.6 | 1.4 | G460S | 1.2 | 1.2 |
| Y200F | 1.7 | 1.5 | G460D | 1.2 | 1.1 |
| Y200C | 1.7 | 1.6 | G460E | 1.3 | 1.2 |
| Y200V | 1.8 | 1.4 | T463C | 1.1 | 1.2 |
| Y200T | 1.8 | 1.6 | T463V | 1.1 | 1.2 |
| Y200L | 1.8 | 1.6 | T463L | 1.1 | 1.0 |
| Y200A | 1.9 | 1.7 | T463D | 1.2 | 1.2 |
| Y200G | 2.0 | 1.8 | T463H | 1.2 | 1.3 |
| Y200S | 2.2 | 2.0 | I464V | 1.1 | 1.0 |
| M202T | 1.8 | 1.5 | N465G | 1.1 | 1.1 |
| Y203F | 1.5 | 1.3 | N465L | 1.4 | 1.3 |
| Y203G | 1.5 | 1.3 | N465R | 1.5 | 1.6 |
| Y203C | 1.5 | 1.2 | N465Q | 1.5 | 1.4 |
| Y203I | 1.6 | 1.4 | Q466L | 1.1 | 1.1 |
| Y203Q | 1.6 | 1.4 | Q466C | 1.1 | 1.1 |
| Y203H | 1.7 | 1.4 | Q466E | 1.1 | 1.2 |
| Y203W | 1.8 | 1.3 | D467C | 1.2 | 1.1 |
| Y203T | 1.9 | 1.4 | D467V | 1.4 | 1.3 |
| Y203L | 2.0 | 1.6 | W469M | 1.0 | 1.4 |
| Y203M | 2.0 | 1.7 | W469E | 1.2 | 1.4 |
| Y203S | 2.1 | 1.2 | W469T | 1.3 | 1.3 |
| Y203V | 2.1 | 1.7 | H471Q | 1.3 | 1.1 |
| A204P | 1.5 | 1.3 | F473Y | 1.2 | 1.1 |
| A204R | 1.5 | 1.4 | F473C | 1.2 | 1.1 |
| A204C | 1.5 | 1.3 | F473R | 1.2 | 1.3 |
| A204H | 1.6 | 1.4 | N475T | 1.2 | 1.1 |
| A204W | 1.6 | 1.4 | N475H | 1.4 | 1.3 |
| A204F | 1.7 | 1.4 | G477Q | 1.6 | 1.4 |
| A204L | 1.8 | 1.6 | G477F | 1.6 | 1.5 |
| A204Y | 1.8 | 1.5 | G477K | 1.6 | 1.5 |
| A204D | 2.0 | 1.6 | G477L | 1.8 | 1.8 |
| A204G | 2.1 | 1.7 | V481Q | 1.2 | 1.1 |
| D205C | 1.8 | 1.6 | V481S | 1.6 | 1.5 |
|  |  |  | W482F | 1.1 | 1.0 |

The variants that showed an IF of at least 1.0 for at least one of the Model detergents are considered to have an improved performance when compared to the parent alpha-amylase, i.e. the alpha-amylase having the amino acid sequence set forth in SEQ ID NO: 3.

Example 3: Stability of Variants

The variants generated as described and listed in Example 1, were further evaluated for stability in Model detergents. Substrate: Phadebas Tablets (Magle Life Sciences) 1 tablet was suspended in 10 ml of the detergent solutions. Assay Procedure:

20 ul of culture supernatant was transferred into two 96Well plates named as Unstress and Stress. To this 80 ul of detergent mixed with EDTA was added, and mixed well. The Unstressed plate was incubated at 4° C. for 16 hrs and Stressed plates were incubated at 43° C. for 16 hrs. The Unstress and Stress samples were diluted 20× in buffer. 20 ul of the diluted culture was added to the pre-dispensed substrate plate and mixed well. The plate was incubated for 20 min at 25° C. with shaking (900 rpm). After the incubation the plate was allowed to settle for 5 mins. 50 ul of the supernatant was transferred into 384 well plates and the absorbance was measured at 620 nm.

The stability was calculated as % Residual activity of the ratio between Stress and Unstress sample (% RA=stress/unstress*100). The Improvement Factor (IF) was calculated as: % RA of variant/% RA of WT.

TABLE 3

The stability results obtained are listed below

| Substitution | Stability | Substitution | Stability | Substitution | Stability |
| --- | --- | --- | --- | --- | --- |
| H1V | 1.6 | E212G | 1.7 | F405G | 1.4 |
| H1L | 1.5 | E212I | 2.1 | F405A | 1.2 |
| H2T | 1.2 | E212Y | 1.4 | D406V | 1.1 |
| D3R | 1.3 | E212R | 1.4 | D406T | 1.1 |
| D3Y | 1.4 | E212C | 1.5 | D406M | 1.1 |
| D3W | 1.4 | E212K | 1.8 | D406S | 1.2 |
| D3S | 1.5 | V213C | 1.2 | D409G | 1.2 |
| D3F | 1.5 | V213W | 1.9 | V410L | 1.3 |
| T5L | 1.3 | V213R | 1.6 | V410E | 2.1 |
| T5F | 1.2 | V213F | 1.6 | T414A | 1.0 |
| T5W | 1.2 | I214V | 1.3 | R415A | 1.0 |
| G7F | 1.6 | N215C | 1.7 | R415Q | 1.3 |
| G7V | 1.3 | N215T | 2.0 | E416V | 1.4 |
| G7E | 1.4 | L217S | 1.3 | E416L | 1.2 |
| G7E | 1.7 | L217A | 1.2 | E416A | 1.3 |
| G7D | 1.2 | L217W | 1.3 | E416Q | 1.5 |
| G7L | 1.3 | N218S | 1.4 | N418M | 1.5 |
| G7A | 1.7 | N218D | 1.6 | N418G | 1.6 |
| I9M | 1.0 | N218R | 1.6 | N418R | 1.7 |
| I9L | 1.2 | N218L | 1.8 | N418F | 1.9 |
| Q11L | 1.1 | N218M | 2.0 | A419M | 1.5 |
| Q11V | 1.0 | R219L | 1.1 | A419G | 1.2 |
| Q11M | 1.0 | W220L | 1.5 | A419V | 1.4 |
| E14Q | 1.4 | W220I | 1.6 | A419L | 1.5 |
| W15G | 1.1 | W220P | 1.7 | A419Q | 1.6 |
| W15S | 1.0 | W220E | 1.7 | A419R | 1.8 |
| W15I | 1.2 | W220R | 1.8 | S420M | 1.8 |
| N16R | 1.5 | W220A | 1.8 | H421T | 1.1 |
| V17D | 1.5 | W220S | 1.8 | P422Y | 1.7 |
| V17G | 1.5 | G221S | 1.0 | P422H | 1.8 |
| V17E | 1.5 | G221A | 1.5 | P422D | 1.8 |
| V17Q | 1.6 | V222E | 1.1 | P422R | 1.9 |
| V17A | 1.6 | V222L | 1.1 | S424L | 1.2 |
| V17T | 1.7 | W223F | 1.1 | G425V | 1.2 |
| V17L | 1.7 | W223L | 1.2 | L426S | 1.2 |
| N19G | 1.1 | N226C | 2.4 | L426A | 1.3 |
| N19S | 1.1 | N226M | 1.9 | A427S | 1.3 |
| Q22C | 1.2 | N226E | 2.0 | M430L | 1.6 |
| Q22A | 1.5 | N226K | 2.2 | M430A | 1.2 |
| Q22Y | 1.5 | N226R | 2.3 | M430T | 1.3 |
| H23W | 1.2 | T227L | 1.3 | S431A | 1.5 |
| W24F | 1.2 | T227Y | 1.2 | S431T | 1.2 |
| N25V | 1.4 | T227R | 1.2 | S431F | 2.4 |
| N25R | 1.2 | L228F | 1.2 | D432Q | 1.2 |
| N25L | 1.2 | L228M | 1.0 | D432P | 1.2 |
| N25T | 1.3 | D231P | 1.2 | G435N | 1.2 |
| R26L | 1.3 | F233T | 2.5 | G435M | 1.3 |
| R26E | 1.3 | F233P | 2.6 | G435I | 1.4 |
| H28E | 1.6 | F233M | 3.2 | G435S | 1.6 |
| H28R | 1.4 | W238A | 1.2 | W439E | 1.2 |
| H28M | 1.5 | H240W | 1.3 | W439A | 1.4 |
| H28W | 1.7 | K242A | 1.9 | Y441K | 1.2 |
| H28K | 1.8 | F245G | 1.0 | Q445R | 1.6 |
| N29G | 1.3 | F245A | 1.0 | K446G | 1.4 |
| N29K | 1.1 | R247Y | 1.2 | K446T | 1.1 |
| N29V | 1.3 | R247G | 1.3 | K446P | 1.3 |
| N29W | 1.4 | R247M | 1.3 | A447R | 1.1 |
| N30S | 1.1 | D248G | 1.6 | A447S | 1.5 |
| N30R | 1.1 | D248R | 1.6 | G448R | 1.0 |
| A31S | 1.0 | W249F | 1.1 | V450T | 1.1 |
| A31G | 1.0 | L250C | 1.4 | V450Q | 1.1 |
| A31R | 1.0 | L250F | 1.3 | V450R | 1.2 |
| N33D | 3.3 | L250Y | 1.6 | W451L | 1.0 |
| L34Y | 1.0 | G251K | 1.6 | H452C | 1.1 |
| K35L | 1.0 | G251M | 1.7 | H452G | 1.1 |
| N36V | 1.7 | G251Q | 1.9 | H452Y | 1.1 |
| N36P | 1.7 | H252C | 1.4 | H452R | 1.1 |
| N36W | 1.8 | H252T | 1.4 | H452V | 1.4 |
| A37E | 1.4 | H252F | 1.5 | M454Q | 1.3 |
| G38M | 1.1 | H252V | 1.6 | M454S | 1.5 |
| G38Y | 1.3 | V253A | 1.0 | G456Y | 1.2 |
| G38K | 1.3 | V253L | 1.1 | G456K | 1.1 |
| I39L | 1.2 | T257V | 1.3 | G456L | 1.1 |
| I39V | 1.2 | G258P | 1.1 | S459E | 1.1 |
| T40Q | 1.7 | G258F | 1.1 | S459Q | 1.2 |
| T40A | 1.3 | G258D | 3.2 | S459R | 1.1 |

TABLE 3-continued

The stability results obtained are listed below

| Substitution | Stability | Substitution | Stability | Substitution | Stability |
| --- | --- | --- | --- | --- | --- |
| T40S | 2.3 | K259L | 1.3 | T463M | 1.1 |
| A41Q | 1.2 | K259A | 1.3 | T463A | 1.1 |
| I42V | 1.1 | K259S | 1.3 | T463Q | 1.1 |
| I42L | 1.2 | K259D | 1.4 | N465L | 1.1 |
| I44T | 1.2 | K259C | 1.4 | N465R | 1.1 |
| I44L | 1.1 | N260W | 1.5 | D467C | 1.1 |
| I44V | 1.1 | N260S | 1.4 | F473E | 1.2 |
| A47G | 1.0 | N260R | 1.5 | F473G | 1.3 |
| A47T | 1.0 | L261T | 1.3 | F473T | 1.4 |
| W48C | 1.7 | V264L | 1.0 | F473V | 1.5 |
| W48I | 2.0 | W268Y | 1.1 | N475G | 1.5 |
| W48H | 1.8 | K269W | 1.8 | G476F | 1.1 |
| W48A | 1.8 | K269Q | 1.3 | W482F | 1.0 |
| K49Q | 1.1 | K269R | 1.3 | | |
| S52M | 1.6 | L272M | 1.2 | | |
| S52V | 1.8 | G273E | 1.5 | | |
| S52C | 1.5 | L275G | 1.2 | | |
| S52F | 1.5 | L275E | 1.2 | | |
| S52A | 1.6 | L275A | 1.4 | | |
| S52D | 1.7 | L275R | 1.4 | | |
| S52K | 1.7 | L275K | 1.4 | | |
| S52N | 1.8 | E276L | 1.6 | | |
| S52E | 1.8 | N277D | 1.5 | | |
| S52T | 1.8 | L279Q | 1.4 | | |
| Q53V | 1.5 | L279M | 1.3 | | |
| Q53L | 1.8 | S280R | 1.0 | | |
| Q53M | 1.6 | S280E | 1.0 | | |
| N54T | 1.7 | S280D | 1.1 | | |
| N54L | 1.8 | K281A | 1.4 | | |
| N54I | 1.9 | T285W | 1.4 | | |
| D55G | 1.8 | T285M | 1.5 | | |
| V56L | 1.7 | T285P | 2.1 | | |
| G59E | 1.7 | M286C | 1.2 | | |
| G59S | 1.4 | M286C | 1.2 | | |
| A60V | 1.6 | P292L | 1.8 | | |
| A60F | 2.4 | P292G | 1.7 | | |
| L63C | 1.2 | L293T | 1.3 | | |
| L63G | 1.2 | L293G | 1.5 | | |
| L63A | 1.3 | L293Y | 1.3 | | |
| E68S | 1.3 | L293Q | 2.1 | | |
| E68M | 1.3 | H294W | 1.2 | | |
| E68C | 1.3 | H294Q | 1.2 | | |
| E68T | 1.4 | H294S | 1.5 | | |
| E68V | 1.4 | Y295I | 1.1 | | |
| E68Q | 1.4 | Y295A | 1.2 | | |
| E68Y | 1.4 | N296S | 1.3 | | |
| G73C | 1.2 | N296K | 1.4 | | |
| T74V | 1.2 | N296H | 1.9 | | |
| T74L | 1.3 | L297W | 1.4 | | |
| T74N | 1.0 | L297H | 1.2 | | |
| V75T | 2.4 | Q299S | 1.4 | | |
| V75E | 1.4 | Q299L | 1.8 | | |
| R76V | 2.6 | Q299R | 2.1 | | |
| T77V | 1.1 | Q299A | 1.4 | | |
| T81G | 1.2 | Q299H | 1.4 | | |
| K82G | 1.0 | Q299P | 1.6 | | |
| A83Q | 1.2 | A300C | 1.2 | | |
| A83R | 1.2 | N302S | 1.2 | | |
| A83S | 1.2 | S303A | 1.1 | | |
| A83F | 1.2 | S303M | 1.3 | | |
| A83V | 1.2 | S304G | 1.6 | | |
| E84M | 1.0 | S304L | 1.6 | | |
| E84W | 1.1 | S304F | 1.7 | | |
| E86W | 1.3 | S304A | 1.8 | | |
| E86R | 1.3 | S304M | 1.9 | | |
| I89A | 1.0 | G305Q | 1.1 | | |
| I89L | 1.1 | G305F | 1.9 | | |
| R90L | 1.3 | G305I | 2.0 | | |
| S91A | 1.1 | N306V | 2.0 | | |
| S91G | 1.2 | N306L | 1.8 | | |
| S91V | 1.1 | N306D | 1.9 | | |
| S91T | 1.3 | N306S | 2.0 | | |
| L92C | 1.2 | N306T | 2.0 | | |
| L92F | 1.1 | R310A | 1.4 | | |
| N95E | 1.8 | R310T | 1.5 | | |
| N95S | 1.8 | N311L | 1.2 | | |

TABLE 3-continued

The stability results obtained are listed below

| Substitution | Stability | Substitution | Stability | Substitution | Stability |
|---|---|---|---|---|---|
| N95G | 3.5 | N311R | 1.3 | | |
| N95D | 1.7 | N311C | 1.8 | | |
| N95R | 1.8 | N311Y | 1.8 | | |
| G96R | 1.1 | L312F | 2.0 | | |
| I97V | 1.1 | L312V | 1.6 | | |
| I97L | 1.3 | L312I | 1.4 | | |
| Q98V | 1.3 | L313M | 1.4 | | |
| Q98L | 1.4 | L313I | 1.4 | | |
| Q98F | 1.1 | G315V | 1.3 | | |
| Q98W | 1.3 | G315T | 1.2 | | |
| Q98P | 1.3 | G315R | 1.3 | | |
| Q98H | 1.4 | G315F | 1.4 | | |
| V99G | 1.6 | T316S | 1.3 | | |
| V99E | 2.6 | T316C | 1.2 | | |
| Y100W | 1.2 | T316G | 1.2 | | |
| V103A | 1.0 | V318L | 1.0 | | |
| V103S | 1.4 | Q319P | 1.3 | | |
| V103T | 1.4 | Q319H | 1.6 | | |
| H107M | 1.2 | Q319D | 1.6 | | |
| K108V | 1.4 | Q319F | 1.7 | | |
| G109D | 1.5 | R320V | 1.6 | | |
| G109F | 1.6 | R320C | 1.0 | | |
| G110C | 1.4 | R320A | 1.1 | | |
| A111S | 1.8 | R320S | 1.1 | | |
| D112V | 1.1 | H321T | 1.4 | | |
| D112F | 1.2 | H321G | 1.2 | | |
| D112C | 1.3 | H321R | 1.5 | | |
| D112K | 2.9 | H321S | 1.6 | | |
| F113M | 1.2 | V326G | 1.0 | | |
| F113V | 1.4 | V326A | 1.0 | | |
| F113E | 1.2 | V326C | 1.0 | | |
| F113K | 1.8 | V326T | 1.1 | | |
| T114S | 1.2 | T327V | 2.2 | | |
| T114V | 1.4 | T327L | 1.3 | | |
| T114L | 1.5 | T327Q | 1.1 | | |
| R116Q | 1.5 | T327E | 1.6 | | |
| R116K | 1.6 | F328M | 1.1 | | |
| V117G | 1.5 | F328C | 1.1 | | |
| V117I | 1.7 | V329S | 1.0 | | |
| V117M | 1.7 | V329C | 1.1 | | |
| Q118V | 1.5 | V329I | 1.1 | | |
| Q118G | 1.5 | T334A | 1.4 | | |
| Q118E | 1.6 | T334S | 1.6 | | |
| Q118F | 1.7 | P336L | 2.0 | | |
| Q118R | 1.8 | P336W | 1.5 | | |
| V120C | 1.1 | P336S | 1.6 | | |
| V120A | 1.1 | P336K | 1.8 | | |
| V120N | 1.2 | G337V | 1.1 | | |
| V122L | 3.2 | G337F | 1.1 | | |
| N123K | 1.5 | E338T | 1.0 | | |
| N123V | 1.5 | E338A | 1.6 | | |
| P124R | 1.3 | E338H | 2.6 | | |
| P124G | 1.5 | E341P | 1.4 | | |
| N126G | 1.1 | E341M | 1.7 | | |
| N126A | 1.1 | E341F | 1.9 | | |
| N126R | 1.1 | E341K | 1.9 | | |
| N126T | 1.7 | E341S | 2.2 | | |
| N128S | 1.7 | S342A | 1.2 | | |
| N128E | 1.7 | V344L | 1.4 | | |
| N128P | 1.5 | Q345L | 1.0 | | |
| N128G | 1.5 | Q345W | 1.0 | | |
| N128A | 2.0 | Q345N | 1.0 | | |
| Q129E | 1.3 | G346R | 1.0 | | |
| V131I | 1.6 | G346S | 1.7 | | |
| G133A | 1.3 | W347L | 1.9 | | |
| G133D | 1.4 | W347R | 1.6 | | |
| G133R | 1.2 | W347V | 1.6 | | |
| Q136E | 1.8 | W347C | 1.7 | | |
| Q136W | 2.0 | F348P | 1.0 | | |
| Q136G | 2.0 | F348M | 1.3 | | |
| I137V | 1.5 | P350S | 1.1 | | |
| E138A | 1.4 | P350Q | 1.3 | | |
| E138Y | 1.3 | P350D | 1.1 | | |
| E138T | 1.5 | P350E | 1.1 | | |
| E138L | 2.2 | L351W | 1.2 | | |
| A139S | 2.2 | L351H | 1.5 | | |

TABLE 3-continued

The stability results obtained are listed below

| Substitution | Stability | Substitution | Stability | Substitution | Stability |
|---|---|---|---|---|---|
| A139G | 2.0 | L351Q | 1.6 | | |
| A139V | 2.0 | A354C | 2.1 | | |
| A139T | 2.3 | T355L | 1.1 | | |
| A139P | 2.6 | T355Y | 1.2 | | |
| W140H | 1.3 | T355F | 1.2 | | |
| T141S | 1.8 | L357H | 1.0 | | |
| T141C | 1.3 | T358L | 1.3 | | |
| T141G | 1.5 | E360G | 1.2 | | |
| G142R | 1.5 | E360A | 1.2 | | |
| G142A | 1.9 | E360M | 1.4 | | |
| F143M | 1.4 | Q361V | 1.0 | | |
| F143L | 1.8 | Q361G | 1.0 | | |
| F143I | 1.3 | Q361D | 1.0 | | |
| N144M | 1.4 | Q361S | 1.3 | | |
| N144K | 1.4 | Y363L | 1.4 | | |
| N144G | 1.6 | Y363R | 1.5 | | |
| N144R | 1.8 | Y363V | 1.9 | | |
| F145A | 2.5 | Q365M | 1.0 | | |
| F145N | 1.8 | Q365L | 1.1 | | |
| F145Q | 1.8 | Q365T | 1.1 | | |
| F145T | 2.0 | Q365C | 1.1 | | |
| F145H | 2.1 | Q365S | 1.3 | | |
| P146L | 1.7 | V366I | 1.0 | | |
| P146M | 1.6 | V366C | 1.0 | | |
| P146T | 1.8 | F367L | 1.2 | | |
| G149Y | 1.8 | F367S | 1.2 | | |
| G149L | 1.8 | F367A | 1.3 | | |
| G149A | 1.9 | Y368H | 1.3 | | |
| Q151L | 3.7 | G369L | 1.3 | | |
| S153G | 1.3 | Y372A | 1.1 | | |
| S153T | 1.5 | G373T | 1.4 | | |
| S154M | 2.3 | G373Q | 1.5 | | |
| S154E | 2.4 | G373W | 1.5 | | |
| S154A | 2.4 | G373R | 1.6 | | |
| S154V | 2.4 | I374Y | 1.5 | | |
| F155W | 1.2 | I374S | 1.5 | | |
| K156F | 2.1 | I374M | 1.5 | | |
| K156Q | 1.4 | I374L | 1.6 | | |
| K156L | 2.0 | P375E | 1.5 | | |
| K156S | 2.1 | P375S | 1.5 | | |
| K156G | 2.0 | P375V | 1.6 | | |
| K156N | 1.2 | P375R | 1.6 | | |
| K156T | 1.2 | S376R | 1.5 | | |
| R158S | 1.0 | S376L | 1.1 | | |
| Y160W | 1.1 | S376V | 1.3 | | |
| Y160R | 1.1 | S376I | 1.4 | | |
| Y160H | 1.5 | S376Q | 1.4 | | |
| H161C | 1.1 | S376F | 1.5 | | |
| T165I | 1.5 | S376E | 1.7 | | |
| T165V | 1.1 | S376T | 1.7 | | |
| T165E | 1.1 | D377S | 1.0 | | |
| D166S | 1.6 | D377G | 1.3 | | |
| Q169L | 1.6 | D377T | 1.9 | | |
| Q169S | 1.6 | V379L | 2.0 | | |
| Q169V | 1.8 | V379S | 1.5 | | |
| Q169F | 2.2 | P380V | 1.1 | | |
| S170A | 2.5 | P380Y | 1.1 | | |
| S170V | 2.3 | S381V | 1.7 | | |
| S170Q | 1.8 | Y382K | 1.3 | | |
| S170W | 1.8 | Y382R | 2.7 | | |
| S170G | 1.8 | R383V | 1.1 | | |
| S170F | 1.8 | Q384S | 1.2 | | |
| S170T | 1.9 | Q384V | 1.2 | | |
| S170L | 2.2 | Q384T | 1.3 | | |
| R171A | 1.6 | Q384G | 1.3 | | |
| R171M | 1.6 | Q384E | 1.5 | | |
| Q172L | 1.8 | I386L | 1.1 | | |
| Q172E | 1.8 | I386M | 1.1 | | |
| Q172C | 1.5 | I386W | 1.2 | | |
| Q172R | 1.8 | I386V | 1.2 | | |
| Q172Q | 1.9 | D387Q | 1.2 | | |
| Q172W | 2.1 | D387L | 1.4 | | |
| L173I | 1.2 | P388S | 1.5 | | |
| L173A | 1.2 | P388R | 1.5 | | |
| A174V | 1.4 | P388K | 1.7 | | |
| A174L | 1.4 | P388L | 1.7 | | |

TABLE 3-continued

| Substitution | Stability | Substitution | Stability | Substitution | Stability |
|---|---|---|---|---|---|
| A174M | 1.4 | L389A | 1.6 | | |
| A174K | 1.6 | L389V | 1.6 | | |
| N175G | 1.2 | L389F | 1.7 | | |
| N175S | 1.4 | L389M | 1.8 | | |
| R176Y | 1.5 | L390V | 1.5 | | |
| R176M | 1.6 | L390T | 1.2 | | |
| R176T | 1.8 | L390N | 1.3 | | |
| R176K | 2.2 | L390H | 1.3 | | |
| Y178W | 1.1 | L390C | 1.5 | | |
| K179L | 1.5 | K391Q | 1.3 | | |
| R181A | 1.8 | A392I | 1.4 | | |
| R181G | 1.8 | A392M | 1.3 | | |
| R181D | 1.5 | A392T | 1.4 | | |
| K185G | 3.5 | Q394N | 1.5 | | |
| A186S | 2.1 | Q394L | 1.7 | | |
| A186D | 1.7 | Q394T | 1.9 | | |
| A186T | 1.7 | Q394M | 1.9 | | |
| A186Q | 1.8 | Q395E | 1.2 | | |
| A186V | 2 | Q395K | 1.4 | | |
| T193S | 1.6 | Q395R | 1.5 | | |
| T193D | 1.5 | Q395V | 1.0 | | |
| T193R | 1.5 | Q395S | 1.0 | | |
| T193G | 2.6 | Q395M | 1.0 | | |
| N195T | 1.5 | Y396R | 1.2 | | |
| N195F | 1.9 | Y396W | 1.3 | | |
| G196P | 1.2 | A397S | 1.3 | | |
| Y198A | 1.0 | Y398S | 1.3 | | |
| Y198G | 1.2 | Y398C | 1.4 | | |
| Y203W | 1.6 | Y398N | 1.4 | | |
| Y203L | 2.0 | Y398K | 1.6 | | |
| D205R | 1.3 | R400E | 1.5 | | |
| D205A | 1.6 | R400I | 1.5 | | |
| D205L | 2.9 | H402L | 1.1 | | |
| V206A | 2.1 | H402D | 1.1 | | |
| V206S | 2.1 | H402R | 1.3 | | |
| V206K | 2.4 | H402T | 1.5 | | |
| D209S | 2.2 | D403P | 1.1 | | |
| D209M | 2.2 | D403Q | 1.1 | | |
| D209V | 2.6 | D403I | 1.2 | | |
| D209Q | 1.5 | Y404K | 1.3 | | |
| D209L | 1.9 | Y404F | 1.7 | | |
| D209I | 2.5 | Y404W | 1.8 | | |

The variants having an IF of at least 1.0 were considered to have an improved stability compared to the parent alpha-amylase, i.e. the alpha-amylase having an amino acid sequence as set forth in SEQ ID NO: 3.

Example 4: Mean Hit Values of Variants

As can be seen from FIG. 1-3, a large number of variants have been generated and tested for specific activity in Model A and Model X detergent compositions as well as for stability. In particular, FIG. 1 shows the Improvement Factor (IF) as a measure for the specific activity of the variants in Model A detergent composition, FIG. 2 shows the IF as a measure of the specific activity of the variants in Model X detergent composition, and FIG. 3 shows the IF as a measure for the stability of the variants in Model A detergent composition. A mean hit value for each position which has been subject for modifications have been calculated (see Table 4).

TABLE 4

| | Mean hit value for each position | | |
|---|---|---|---|
| Position | Model A | Model X | Stability |
| 1 | 1.2 | 1.2 | 1.2 |
| 2 | 1.2 | 1.1 | 1.5 |

TABLE 4-continued

| | Mean hit value for each position | | |
|---|---|---|---|
| Position | Model A | Model X | Stability |
| 3 | 1.0 | 1.1 | 1.2 |
| 4 | 1.0 | 1.1 | 1.1 |
| 5 | 1.1 | 1.2 | 1.1 |
| 6 | 1.3 | 1.4 | 1.1 |
| 7 | 1.4 | 1.3 | 1.3 |
| 8 | 1.1 | 1.1 | 1.9 |
| 9 | 1.1 | 1.2 | 1.7 |
| 10 | 1.1 | 1.2 | 1.2 |
| 11 | 1.1 | 1.1 | 1.6 |
| 12 | 1.1 | 1.1 | 2.2 |
| 13 | 1.2 | 1.1 | 1.5 |
| 14 | 1.5 | 1.1 | 1.5 |
| 15 | 1.2 | 1.1 | 1.2 |
| 16 | 1.2 | 1.2 | 1.2 |
| 17 | 1.2 | 1.2 | 1.4 |
| 18 | 1.2 | 1.2 | 1.8 |
| 19 | 1.3 | 1.3 | 1.2 |
| 20 | 1.0 | 1.0 | 1.5 |
| 21 | 1.1 | 1.1 | 1.0 |
| 22 | 1.2 | 1.2 | 1.2 |
| 23 | 1.2 | 1.2 | 1.2 |
| 24 | 1.7 | 1.6 | 1.0 |
| 25 | 1.2 | 1.2 | 1.1 |
| 26 | 1.3 | 1.3 | 1.3 |
| 27 | 1.1 | 1.1 | 1.3 |
| 28 | 1.1 | 1.1 | 1.3 |
| 29 | 1.1 | 1.1 | 1.1 |
| 30 | 1.1 | 1.1 | 1.1 |
| 31 | 1.1 | 1.2 | 1.0 |
| 32 | 1.2 | 1.2 | |
| 33 | 2.5 | 1.0 | 1.5 |
| 34 | 1.2 | 1.1 | 1.4 |
| 35 | 1.1 | 1.1 | 1.0 |
| 36 | 1.1 | 1.1 | 1.3 |
| 37 | 1.1 | 1.1 | 1.1 |
| 38 | 1.2 | 1.5 | 1.1 |
| 39 | 1.4 | 1.4 | 1.1 |
| 40 | 1.1 | 1.0 | 1.3 |
| 41 | 1.2 | 1.1 | 1.2 |
| 42 | 1.0 | 1.2 | 1.6 |
| 43 | 1.2 | 1.2 | 1.9 |
| 44 | 1.1 | 1.1 | 1.3 |
| 45 | 1.6 | 1.6 | 1.4 |
| 46 | 1.4 | 1.5 | 1.6 |
| 47 | 1.0 | 1.1 | 1.3 |
| 48 | 1.3 | 1.3 | 2.0 |
| 49 | 1.0 | 1.4 | 1.8 |
| 50 | 1.3 | 1.4 | 1.3 |
| 51 | | | 1.3 |
| 52 | 1.2 | 1.2 | 1.4 |
| 53 | 1.2 | 1.2 | 1.3 |
| 54 | 1.1 | 1.1 | 1.3 |
| 55 | 1.3 | 1.3 | 1.1 |
| 56 | 1.2 | 1.2 | 1.6 |
| 57 | 1.1 | 1.4 | 1.1 |
| 58 | 1.2 | 1.1 | 1.8 |
| 59 | 1.2 | 1.2 | 1.5 |
| 60 | 1.3 | 1.3 | 1.6 |
| 61 | 1.2 | 1.6 | 2.0 |
| 62 | 1.4 | 1.1 | 2.1 |
| 63 | 1.1 | 1.3 | 1.1 |
| 64 | 1.2 | 1.2 | 1.7 |
| 65 | 1.4 | 1.7 | 1.8 |
| 66 | 1.1 | 1.1 | 1.2 |
| 67 | 1.7 | 1.2 | 1.8 |
| 68 | 1.1 | 1.1 | 1.3 |
| 69 | 1.1 | 1.1 | 1.5 |
| 70 | 1.2 | 1.2 | 1.5 |
| 71 | 1.3 | 1.2 | 2.2 |
| 72 | 1.3 | 1.3 | 1.3 |
| 73 | 1.2 | 1.2 | 1.2 |
| 74 | 1.2 | 1.2 | 1.6 |
| 75 | 1.1 | 1.1 | 1.3 |
| 76 | 1.2 | 1.2 | 1.8 |
| 77 | 1.1 | 1.1 | 1.8 |
| 78 | 1.3 | 1.1 | 1.9 |

TABLE 4-continued

| Mean hit value for each position | | | |
|---|---|---|---|
| Position | Model A | Model X | Stability |
| 79 | 1.3 | 1.1 | 1.7 |
| 80 | 2.0 | 1.7 | 1.1 |
| 81 | 1.0 | 1.0 | 1.1 |
| 82 | 1.4 | 1.3 | 1.6 |
| 83 | 1.1 | 1.1 | 1.2 |
| 84 | 1.4 | 1.0 | 1.9 |
| 85 | 1.0 | 1.0 | 1.2 |
| 86 | 1.3 | 1.0 | 1.1 |
| 87 | 1.2 | 1.1 | 1.3 |
| 88 | 1.1 | 1.1 | 1.5 |
| 89 | 1.3 | 1.2 | 1.3 |
| 90 | 1.3 | 1.3 | 1.3 |
| 91 | 1.2 | 1.2 | 1.1 |
| 92 | 1.4 | 1.2 | 1.9 |
| 93 | 1.2 | 1.2 | 1.6 |
| 94 | 1.1 | 1.1 | 1.0 |
| 95 | 1.2 | 1.1 | 1.6 |
| 96 | 1.0 | 1.1 | 1.1 |
| 97 | 1.1 | 1.1 | 1.2 |
| 98 | 1.3 | 1.2 | 1.1 |
| 99 | 1.2 | 1.2 | 1.4 |
| 100 | 1.3 | 1.3 | 1.4 |
| 101 | 1.2 | 1.2 | 1.6 |
| 102 | 1.3 | 1.1 | 2.0 |
| 103 | 1.1 | 1.1 | 1.5 |
| 104 | 1.1 | 1.1 | 1.9 |
| 105 | 1.5 | 1.1 | 2.1 |
| 106 | 1.0 | | 2.0 |
| 107 | 1.2 | 1.1 | 1.7 |
| 108 | 1.2 | 1.3 | 1.2 |
| 109 | 1.4 | 1.4 | 1.3 |
| 110 | 1.5 | 1.4 | 1.1 |
| 111 | 1.4 | 1.1 | 1.3 |
| 112 | 1.6 | 1.4 | 1.7 |
| 113 | 1.4 | 1.3 | 1.6 |
| 114 | 1.2 | 1.2 | 1.2 |
| 115 | 1.2 | 1.1 | |
| 116 | 1.4 | 1.4 | 1.4 |
| 117 | 1.7 | 1.3 | 1.3 |
| 118 | 1.3 | 1.3 | 1.4 |
| 119 | 1.3 | 1.2 | 1.4 |
| 120 | 1.1 | 1.2 | 1.2 |
| 121 | 1.3 | 1.3 | 1.0 |
| 122 | 1.2 | 1.1 | 1.6 |
| 123 | 1.2 | 1.2 | 1.4 |
| 124 | 1.3 | 1.2 | 1.2 |
| 125 | 1.1 | 1.1 | 1.8 |
| 126 | 1.2 | 1.2 | 1.5 |
| 127 | 1.6 | 1.5 | 1.2 |
| 128 | 1.3 | 1.2 | 1.3 |
| 129 | 1.2 | 1.2 | 1.5 |
| 130 | 1.2 | 1.2 | 1.8 |
| 131 | 1.2 | 1.2 | 1.3 |
| 132 | 1.3 | 1.3 | 1.4 |
| 133 | 1.2 | 1.2 | 1.4 |
| 134 | 1.2 | 1.2 | 1.6 |
| 135 | 1.5 | 1.5 | 1.5 |
| 136 | 1.2 | 1.2 | 1.6 |
| 137 | 1.3 | 1.2 | 1.2 |
| 138 | 1.0 | 1.0 | 1.3 |
| 139 | 1.3 | 1.2 | 1.7 |
| 140 | 1.4 | 1.3 | 1.0 |
| 141 | 1.3 | 1.3 | 1.9 |
| 142 | 1.2 | 1.2 | 1.3 |
| 143 | 1.2 | 1.2 | 1.7 |
| 144 | 1.2 | 1.1 | 1.2 |
| 145 | 1.2 | 1.2 | 2.3 |
| 146 | 1.2 | 1.2 | 1.3 |
| 147 | 1.2 | 1.2 | 1.1 |
| 148 | 1.3 | 1.1 | 1.4 |
| 149 | 1.2 | 1.2 | 1.2 |
| 150 | 1.2 | 1.1 | 2.2 |
| 151 | 1.3 | 1.3 | 1.7 |
| 152 | 1.3 | 1.1 | 1.1 |
| 153 | 1.1 | 1.1 | 2.0 |
| 154 | 1.1 | 1.1 | 2.5 |

TABLE 4-continued

| Mean hit value for each position | | | |
|---|---|---|---|
| Position | Model A | Model X | Stability |
| 155 | 1.2 | 1.2 | 1.2 |
| 156 | 1.4 | 1.4 | 1.8 |
| 157 | 1.1 | 1.1 | 1.2 |
| 158 | 1.5 | 1.5 | 1.1 |
| 159 | 1.3 | 1.3 | |
| 160 | 1.4 | 1.4 | 1.2 |
| 161 | 1.0 | 1.0 | 1.8 |
| 162 | 1.2 | 1.2 | 1.4 |
| 163 | 1.4 | 1.4 | 2.0 |
| 164 | 1.3 | 1.3 | |
| 165 | 1.4 | 1.3 | 1.1 |
| 166 | 1.5 | 1.3 | 1.5 |
| 167 | 1.3 | 1.4 | 1.6 |
| 168 | 1.5 | 1.2 | 1.5 |
| 169 | 1.2 | 1.2 | 1.8 |
| 170 | 1.3 | 1.2 | 1.6 |
| 171 | 1.8 | 1.7 | 1.6 |
| 172 | 1.1 | 1.1 | 1.6 |
| 173 | 1.3 | 1.3 | 1.4 |
| 174 | 1.2 | 1.2 | 1.1 |
| 175 | 1.2 | 1.2 | 1.6 |
| 176 | 1.6 | 1.5 | 1.6 |
| 177 | 1.4 | 1.2 | 2.2 |
| 178 | 1.2 | 1.2 | 1.8 |
| 179 | 1.6 | 1.5 | 1.3 |
| 180 | 1.1 | 1.1 | 1.5 |
| 181 | 1.5 | 1.6 | 1.3 |
| 184 | 1.1 | 1.1 | 1.0 |
| 185 | 1.7 | 1.5 | 1.0 |
| 186 | 1.2 | 1.1 | 1.3 |
| 187 | 1.3 | 1.2 | 1.8 |
| 188 | 1.3 | 1.2 | 1.8 |
| 189 | 1.1 | 1.1 | 1.3 |
| 190 | 1.2 | 1.1 | 2.4 |
| 191 | 1.2 | 1.1 | 1.3 |
| 192 | 1.1 | 1.0 | 2.3 |
| 193 | 1.1 | 1.1 | 1.3 |
| 194 | 1.1 | 1.1 | 1.4 |
| 195 | 1.0 | 1.1 | 1.4 |
| 196 | 1.1 | 1.1 | 1.1 |
| 197 | 1.1 | 1.1 | 1.1 |
| 198 | 1.0 | 1.6 | 1.1 |
| 199 | 1.3 | 1.3 | 1.5 |
| 200 | 1.0 | 1.0 | 2.1 |
| 201 | 1.0 | 1.2 | |
| 202 | 1.2 | 1.1 | 1.0 |
| 203 | 1.5 | 1.3 | 1.3 |
| 204 | 1.0 | 1.1 | 1.5 |
| 205 | 1.9 | 1.4 | 2.1 |
| 206 | 1.1 | 1.1 | 2.3 |
| 207 | 1.1 | 1.1 | 2.0 |
| 208 | 1.0 | 1.0 | |
| 209 | 1.1 | 1.2 | 1.5 |
| 210 | 1.3 | 1.4 | 1.3 |
| 211 | 1.2 | 1.3 | 1.9 |
| 212 | 1.0 | 1.1 | 1.7 |
| 213 | 1.1 | 1.1 | 1.5 |
| 213 | 1.1 | 1.2 | 1.8 |
| 214 | 1.1 | 1.0 | 1.3 |
| 215 | 1.3 | 1.2 | 1.7 |
| 216 | 1.1 | 1.1 | 1.3 |
| 217 | 1.2 | 1.2 | 1.3 |
| 218 | 1.1 | 1.1 | 1.3 |
| 219 | 1.4 | 1.3 | 1.3 |
| 220 | 1.3 | 1.4 | 2.0 |
| 221 | 1.1 | 1.1 | 1.9 |
| 222 | 1.1 | 1.1 | 1.1 |
| 223 | 1.5 | 1.4 | 1.2 |
| 224 | 1.1 | 1.1 | 1.6 |
| 225 | 1.1 | 1.1 | 1.3 |
| 226 | 1.1 | 1.1 | 1.7 |
| 227 | 1.1 | 1.1 | 1.4 |
| 228 | 1.1 | 1.1 | 1.9 |
| 229 | 1.1 | 1.1 | 1.2 |
| 230 | 1.1 | 1.1 | 2.0 |
| 231 | 1.1 | 1.0 | 2.0 |

TABLE 4-continued

| Mean hit value for each position | | | |
|---|---|---|---|
| Position | Model A | Model X | Stability |
| 232 | 1.0 | 1.0 | 1.7 |
| 233 | 1.1 | 1.2 | 1.5 |
| 234 | 1.3 | 1.0 | 2.1 |
| 235 | 1.1 | 1.1 | 1.4 |
| 236 | 2.6 | | 1.9 |
| 237 | 1.1 | 1.1 | 2.0 |
| 238 | 1.3 | 1.2 | 1.2 |
| 239 | 1.1 | 1.1 | 1.6 |
| 240 | | | 2.0 |
| 241 | 1.1 | 1.0 | 1.8 |
| 242 | 1.3 | 1.4 | 2.0 |
| 243 | 1.1 | 1.1 | 2.0 |
| 244 | 1.0 | 1.0 | 1.4 |
| 245 | 1.5 | 1.5 | 1.8 |
| 246 | 1.1 | 1.1 | 1.4 |
| 247 | 1.2 | 1.2 | 1.2 |
| 248 | 1.1 | 1.1 | 1.4 |
| 249 | 1.1 | 1.1 | 1.6 |
| 250 | 1.1 | 1.1 | 1.3 |
| 251 | 1.1 | 1.1 | 1.2 |
| 252 | 1.1 | 1.0 | 1.2 |
| 253 | 1.2 | 1.2 | 1.8 |
| 254 | 1.1 | 1.1 | 1.0 |
| 255 | 1.0 | 1.0 | 1.4 |
| 256 | 1.1 | 1.1 | 1.8 |
| 257 | 1.0 | 1.0 | 2.2 |
| 258 | 1.1 | 1.1 | 1.0 |
| 259 | 1.1 | 1.1 | 1.1 |
| 260 | 1.1 | 1.1 | 1.2 |
| 261 | 1.1 | 1.1 | 1.1 |
| 262 | 1.3 | 1.5 | 1.1 |
| 263 | 1.2 | 1.2 | 1.1 |
| 264 | 1.1 | 1.1 | 1.7 |
| 265 | 1.2 | 1.2 | 1.4 |
| 266 | 1.3 | 1.2 | 1.7 |
| 267 | 1.1 | 1.1 | 2.1 |
| 268 | 1.1 | 1.0 | 1.8 |
| 269 | 1.2 | 1.3 | 1.4 |
| 269 | 1.3 | 1.2 | 1.5 |
| 270 | 1.2 | 1.3 | 1.2 |
| 271 | 1.1 | 1.3 | 1.6 |
| 272 | 1.3 | 1.1 | 1.6 |
| 273 | 1.1 | 1.2 | 1.2 |
| 274 | 1.2 | 1.2 | 1.1 |
| 275 | 1.1 | 1.1 | 1.7 |
| 276 | 1.1 | 1.2 | 1.4 |
| 277 | 1.0 | 1.0 | 2.6 |
| 278 | 1.1 | 1.0 | 1.9 |
| 279 | 1.2 | 1.2 | 1.4 |
| 280 | 1.1 | 1.1 | 1.4 |
| 281 | 1.1 | 1.1 | 1.4 |
| 282 | 1.0 | 1.1 | 1.8 |
| 283 | 1.1 | 1.1 | 1.4 |
| 284 | 1.2 | 1.2 | 1.1 |
| 285 | 1.0 | 1.0 | 1.2 |
| 286 | 1.1 | 1.1 | 1.2 |
| 287 | 1.2 | 1.3 | 1.6 |
| 288 | 1.1 | 1.2 | 1.4 |
| 289 | 1.3 | 1.5 | 1.2 |
| 290 | 1.2 | 2.1 | 2.2 |
| 291 | 1.1 | 1.1 | 1.4 |
| 292 | 1.1 | 1.1 | 1.6 |
| 293 | 1.2 | 1.2 | 1.2 |
| 294 | 1.1 | 1.1 | 1.4 |
| 295 | 1.1 | 1.1 | 1.1 |
| 296 | 1.2 | 1.2 | 1.4 |
| 297 | 1.1 | 1.1 | 1.7 |
| 298 | 1.0 | 1.2 | 1.4 |
| 299 | 1.2 | 1.1 | 1.7 |
| 300 | 1.1 | 1.1 | 1.5 |
| 301 | 1.1 | 1.2 | 1.2 |
| 302 | 1.2 | 1.1 | 1.2 |
| 303 | 1.1 | 1.1 | 1.2 |
| 304 | 1.0 | 1.0 | 1.5 |
| 305 | 1.1 | 1.2 | 1.1 |
| 306 | 1.0 | 1.1 | 1.4 |

TABLE 4-continued

| Mean hit value for each position | | | |
|---|---|---|---|
| Position | Model A | Model X | Stability |
| 307 | 1.0 | 1.0 | 1.5 |
| 308 | 1.5 | 1.6 | 1.9 |
| 309 | 1.0 | 1.1 | 1.7 |
| 310 | 1.2 | 1.1 | 1.4 |
| 311 | 1.2 | 1.2 | 1.3 |
| 312 | 1.2 | 1.3 | 1.5 |
| 313 | 1.1 | 1.0 | 1.5 |
| 314 | 1.2 | 1.1 | 1.2 |
| 315 | 1.1 | 1.1 | 1.2 |
| 316 | 1.0 | 1.1 | 1.4 |
| 317 | 1.1 | 1.3 | 2.1 |
| 318 | 1.1 | 1.1 | 1.4 |
| 319 | 1.3 | 1.2 | 2.6 |
| 320 | 1.3 | 1.1 | 1.5 |
| 321 | 1.2 | 1.2 | 1.3 |
| 322 | 1.2 | 1.4 | 1.3 |
| 323 | 1.1 | 1.2 | 1.2 |
| 324 | 1.2 | 1.2 | 1.5 |
| 325 | 1.1 | 1.1 | 2.1 |
| 326 | 1.0 | 1.1 | 1.3 |
| 327 | 1.1 | 1.1 | 1.3 |
| 328 | 1.1 | 1.7 | 1.5 |
| 329 | 1.1 | 1.0 | 1.5 |
| 330 | | | 2.5 |
| 331 | 1.2 | 1.1 | 1.1 |
| 332 | 1.2 | 1.4 | 1.3 |
| 333 | | | 2.4 |
| 334 | 1.1 | 1.1 | 1.6 |
| 335 | 1.1 | 1.1 | 1.3 |
| 336 | 1.2 | 1.2 | 1.3 |
| 337 | 1.5 | 1.2 | 1.3 |
| 338 | 1.0 | 1.1 | 1.3 |
| 339 | 1.1 | 1.4 | 2.0 |
| 340 | 1.0 | 1.0 | 1.6 |
| 341 | 1.2 | 1.1 | 1.4 |
| 342 | 1.1 | 1.1 | 1.3 |
| 343 | 1.2 | 1.1 | 1.6 |
| 344 | 1.1 | 1.1 | 1.0 |
| 345 | 1.1 | 1.1 | 1.0 |
| 346 | 1.1 | 1.2 | 1.3 |
| 347 | 1.2 | 1.3 | 1.5 |
| 348 | 1.2 | 1.2 | 1.1 |
| 349 | 1.7 | 1.2 | 1.7 |
| 350 | 1.3 | 1.3 | 1.7 |
| 351 | 1.2 | 1.2 | 1.5 |
| 352 | 1.2 | 1.4 | 1.8 |
| 353 | 1.0 | 1.0 | 2.0 |
| 354 | 1.1 | 1.1 | 1.2 |
| 355 | 1.0 | 1.0 | 1.6 |
| 356 | 1.1 | 1.1 | 1.2 |
| 357 | 1.1 | 1.1 | 1.0 |
| 358 | 1.1 | 1.2 | 1.6 |
| 359 | 1.1 | 1.0 | 1.4 |
| 360 | 1.1 | 1.1 | 1.1 |
| 361 | 1.1 | 1.2 | 1.3 |
| 362 | 1.3 | 1.3 | 1.4 |
| 363 | 1.2 | 1.2 | 1.3 |
| 364 | 1.2 | 1.2 | 1.0 |
| 365 | 1.0 | 1.1 | 1.5 |
| 366 | 1.1 | 1.1 | 1.1 |
| 367 | 1.5 | 1.2 | 1.8 |
| 368 | 1.2 | 1.2 | 1.1 |
| 369 | 1.7 | 1.4 | 1.6 |
| 370 | 1.2 | 1.2 | 2.1 |
| 371 | 1.1 | 1.1 | 1.1 |
| 372 | 1.1 | 1.1 | 1.2 |
| 373 | 1.1 | 1.1 | 1.1 |
| 374 | 1.1 | 1.1 | 1.2 |
| 375 | 1.0 | 1.1 | 1.2 |
| 376 | 1.2 | 1.2 | 1.1 |
| 377 | 1.2 | 1.2 | 1.4 |
| 378 | 1.1 | 1.1 | 1.9 |
| 379 | 1.1 | 1.1 | 1.5 |
| 380 | 1.2 | 1.2 | 1.2 |
| 381 | 1.2 | 1.1 | 2.2 |
| 382 | 1.2 | 1.2 | 1.8 |

TABLE 4-continued

| | Mean hit value for each position | | |
|---|---|---|---|
| Position | Model A | Model X | Stability |
| 383 | 1.1 | 1.1 | 1.7 |
| 384 | 1.0 | 1.1 | 1.1 |
| 385 | 1.1 | 1.1 | 1.2 |
| 386 | 1.2 | 1.1 | 1.3 |
| 387 | 1.1 | 1.1 | 1.2 |
| 388 | 1.1 | 1.1 | 1.2 |
| 389 | 1.2 | 1.2 | 1.4 |
| 390 | 1.1 | 1.1 | 1.3 |
| 391 | 1.1 | 1.1 | 1.3 |
| 392 | 1.0 | 1.1 | 1.1 |
| 393 | 1.2 | 1.1 | 1.2 |
| 394 | 1.1 | 1.1 | 1.0 |
| 395 | 1.2 | 1.1 | 1.5 |
| 396 | 1.1 | 1.1 | 1.2 |
| 397 | 1.1 | 1.1 | 1.1 |
| 398 | 1.0 | 1.0 | 1.2 |
| 399 | 1.1 | 1.2 | 1.3 |
| 400 | 1.2 | 1.1 | 1.2 |
| 401 | 1.2 | 1.1 | 1.1 |
| 402 | 1.2 | 1.2 | 1.2 |
| 403 | 1.0 | 1.1 | 1.4 |
| 404 | 1.0 | 1.0 | 1.1 |
| 405 | 1.1 | 1.2 | 1.4 |
| 406 | 1.3 | 1.3 | 1.3 |
| 407 | 1.2 | 1.3 | 1.7 |
| 408 | 1.2 | 1.1 | 1.9 |
| 409 | 1.5 | 1.4 | 2.1 |
| 410 | 1.2 | 1.2 | 1.3 |
| 411 | 1.1 | 1.1 | 1.5 |
| 412 | 1.3 | 1.2 | 2.0 |
| 413 | 1.4 | 1.2 | 1.6 |
| 414 | 1.1 | 1.1 | 1.9 |
| 415 | 1.1 | 1.1 | 1.7 |
| 416 | 1.3 | 1.2 | 1.2 |
| 417 | 1.0 | 1.2 | 1.4 |
| 418 | 1.2 | 1.2 | 1.3 |
| 419 | 1.1 | 1.1 | 1.3 |
| 420 | 1.0 | 1.0 | 1.7 |
| 421 | 1.1 | 1.1 | 1.3 |
| 422 | 1.0 | 1.5 | 1.5 |
| 423 | 1.0 | 1.1 | 1.2 |
| 424 | 1.1 | 1.0 | 1.4 |
| 425 | 1.2 | 1.2 | 1.9 |
| 426 | 1.0 | 1.0 | 1.1 |
| 427 | 1.1 | 1.3 | 1.1 |
| 428 | 1.1 | 1.2 | 2.0 |
| 429 | 1.1 | 1.2 | 2.9 |
| 430 | 1.0 | 1.0 | 1.3 |
| 431 | 1.1 | 1.2 | 1.3 |
| 432 | 1.0 | 1.9 | 1.5 |
| 433 | 1.1 | 1.1 | 1.0 |
| 434 | 1.2 | 1.2 | 1.2 |
| 435 | 1.3 | 1.3 | 1.1 |
| 436 | 1.1 | 1.2 | 1.1 |
| 437 | 1.1 | 1.1 | 1.1 |
| 438 | 1.0 | 1.0 | 1.1 |
| 439 | 1.1 | 1.2 | 1.4 |
| 440 | 1.1 | 1.2 | 1.6 |
| 441 | 1.0 | 1.0 | 1.0 |
| 442 | 1.1 | 1.1 | 1.2 |
| 443 | 1.1 | 1.1 | |
| 444 | 1.1 | 1.1 | 1.6 |
| 445 | 1.1 | 1.0 | 1.2 |
| 446 | 1.0 | 1.0 | 1.1 |
| 447 | 1.1 | 1.1 | 1.1 |
| 448 | 1.1 | 1.1 | 1.0 |
| 449 | 1.1 | 1.1 | 1.2 |
| 450 | 1.0 | 1.0 | 1.2 |
| 451 | 1.1 | 1.1 | 1.7 |
| 452 | 1.0 | 1.1 | 1.1 |
| 453 | 1.1 | 1.3 | 2.3 |
| 454 | 1.1 | 1.0 | 1.3 |
| 455 | 1.1 | 1.1 | 1.6 |
| 456 | 1.1 | 1.1 | 1.1 |
| 457 | 1.0 | 1.1 | 1.2 |
| 458 | 1.1 | 1.1 | 1.1 |

TABLE 4-continued

| | Mean hit value for each position | | |
|---|---|---|---|
| Position | Model A | Model X | Stability |
| 459 | 1.1 | 1.1 | 1.2 |
| 460 | 1.1 | 1.1 | 1.3 |
| 461 | 1.1 | 1.1 | 1.1 |
| 462 | 1.1 | 1.1 | 1.1 |
| 463 | 1.0 | 1.0 | 1.1 |
| 464 | 1.1 | 1.1 | |
| 465 | 1.1 | 1.1 | 1.4 |
| 466 | 1.0 | 1.0 | 2.2 |
| 467 | 1.1 | 1.1 | 1.7 |
| 468 | 1.3 | 1.1 | 1.9 |
| 469 | 1.1 | 1.1 | |
| 470 | 1.0 | 1.0 | 1.5 |
| 471 | 1.1 | 1.1 | 1.2 |
| 472 | 2.2 | 1.2 | 1.9 |
| 473 | 1.2 | 1.1 | 1.2 |
| 474 | 1.2 | 1.3 | 1.8 |
| 475 | 1.1 | 1.1 | 1.9 |
| 476 | 1.4 | 1.3 | 1.3 |
| 477 | 1.4 | 1.3 | 1.2 |
| 478 | 1.0 | 1.1 | 1.2 |
| 479 | 1.0 | 1.0 | 2.2 |
| 480 | 1.1 | 1.2 | 1.7 |
| 481 | 1.0 | 1.1 | 1.0 |
| 482 | 1.1 | 1.2 | 1.9 |
| 483 | 1.1 | 1.1 | 1.0 |

As can be seen from the table above, each of the tested positions have an IF of at least 1.0 for at least one of the conditions the variants have been tested for, i.e. specific activity in Model A and/or Model X detergent compositions, and/or stability in Model A detergent composition.

Example 5: Specific Activity and Stability of Variants of the Invention

In order to determine whether the variants generated as described and listed in Example 2 have a maintained or even improved activity, the variants were evaluated by the Phadebas assay. The following detergent compositions were prepared;

Preparation of Model X (0.175%):

1:2 molar ratio of CaCl2 and MgCl2 stock solution with 6000 dH (water hardness).

104.9 g of $CaCl_2 \cdot 2H_2O$ (0.713M) was weighed into 1 liter bottle and to this 500 ml of type I water was added and stirred well. To this 72.5 g of MgCl2·6H2O (0.357M) was weighed and added, dissolved well and the final volume was made up to 1000 ml with type I water.

0.535 M Solution of NaHCO3

44.9 g of Sodium Hydrogen carbonate was dissolved in 100 ml of type I water.

Model X Detergent with X Ionics with a Water Hardness of 12 (12° dH)

1.75 g of Model X detergent (as described above) was weighed and transferred into 1 litre bottle and to this 800 ml of type I water was added and mixed well. To this 35 mg of X-ionics was added and mixed well. To adjust the water hardness to 12° dH, 2 ml of 1:2 molar ratio of $CaCl_2$ and $MgCl_2$ stock solution with 6000° dH, 6 ml of 0.535 Molar solution of $NaHCO_3$ was added and mixed well. Finally the volume was made up to 1000 ml and the mixture was stirred for 10 min.

Preparation of Model A (0.33%):
4:1 Molar Ratio of CaCl2 and MgCl2 Stock Solution with 6000 dH (Water Hardness)

125.8 g of CaCl2·2H2O was weighed into 1 liter bottle and to this 500 ml of type I water was added and stirred well. To this 43.8 g of MgCl2·6H2O was weighed and added and dissolved well and the final volume was made up to 1000 ml with type I water.

0.535 M Solution of NaHCO3

44.9 g of Sodium Hydrogen carbonate was dissolved in 100 ml of type I water.

Model A Detergent with a Water Hardness of 15 (15° dH)

3.335 g of Model A detergent was weighed and transferred into 1 litre bottle and to this 865 ml of type I water was added and mixed well. To this 7.5 ml of 0.535 M NaHCO$_3$ was added, mixed well and made up the volume to 1 liter with type 1 water. To adjust the water hardness to 15° dH 2.5 ml of 4:1 molar ratio of CaCl$_2$·2H$_2$O and MgCl$_2$·6H$_2$O stock solution with 6000° dH was added and the mixture was stirred for 15 min.

Substrate: Phadebas Tablets (Magle Life Sciences)

1 tablet was suspended in 10 ml of the detergent solutions.

Buffer: 100 mM MOPS Buffer pH 8

Experimental Procedure

Preparation of the Mother Plates:

Colonies were picked from the transformed plate by colony picker (KBiosystems) and inoculated in 96-well culture plate comprising TBGly media for growth. The cultures were grown for 3 days at 37° C. and the supernatant was recovered from the plates by centrifugation.

Preparation of the Substrate Plates:

The substrate solution was prepared by dissolving 1 tablet of phadebas in 10 ml of Model X/Model A detergent and 180 ul of the same was dispensed into 96 Well micro titer plate using multidrop instrument with constant stirring.

The culture supernatant was diluted to 100× with buffer and 20 ul of the diluted culture was added to the 180 ul of pre-dispensed substrate plate and mixed well. The plate was incubated for 20 min at 25° C. with shaking (900 rpm). After the incubation the plate was allowed to settle for 5 mins. 50 ul of the supernatant was transferred into 384 well plates and the absorbance was measured at 620 nm. The concentration of the expressed enzyme was determined by ELISA using specific antibodies. The specific activity was calculated by taking the ratio of the activity by concentration and the hits were identified as anything higher than the specific activity of the parent alpha-amylase. The Improvement Factor (IF) was calculated as: [Specific Activity of variant]/[Specific Activity of parent alpha-amylase].

Stability of the Variants of the Invention

Substrate: Phadebas Tablets (Magle Life Sciences)

1 tablet was suspended in 10 ml of the detergent solutions.

Assay Procedure:

20 ul of culture supernatant was transferred into two 96Well plates named as Unstress and Stress. To this 80 ul of detergent mixed with EDTA was added, and mixed well. The Unstressed plate was incubated at 4° C. for 16 hrs and Stressed plates were incubated at 43° C. for 16 hrs. The Unstress and Stress samples were diluted 20× in buffer. 20 ul of the diluted culture was added to the pre-dispensed substrate plate and mixed well. The plate was incubated for 20 min at 25° C. with shaking (900 rpm). After the incubation the plate was allowed to settle for 5 mins. 50 ul of the supernatant was transferred into 384 well plates and the absorbance was measured at 620 nm.

The stability was calculated as % Residual activity of the ratio between Stress and Unstress sample (% RA=stress/unstress*100). The Improvement Factor (IF) was calculated as: % RA of variant/% RA of WT.

The specific activity of the variants according to the invention obtained by the method described above are the following (amino acid substitutions refer to SEQ ID NO: 3) shown in Table 5 below.

TABLE 5

| Specific variants of the present invention. | | | |
|---|---|---|---|
| Substitution | Model A | Model X | Stability Model A |
| G7S | 0.9 | 0.9 | 1.1 |
| G7N | 0.8 | 0.8 | 1.1 |
| E14F | 1.1 | 0.7 | 1.0 |
| W15H | 0.8 | 0.5 | 1.1 |
| N29A | 1.1 | 1.1 | 1.0 |
| N36T | 0.9 | 0.9 | 1.1 |
| W48Y | 1.6 | 1.3 | 1.2 |
| W48F | 1.3 | 1.2 | 1.4 |
| T51A | 1.1 | 1.1 | 1.0 |
| A60T | 1.4 | 1.4 | 0.8 |
| F113Y | 1.2 | 1.3 | 1.0 |
| R116W | 0.7 | 0.7 | 1.0 |
| A119W | 1.1 | 1.0 | |
| V122I | 1.4 | 1.2 | 0.0 |
| V122F | 1.1 | 1.0 | 0.0 |
| S132V | 1.1 | 1.0 | 0.0 |
| S132Q | 1.1 | 1.0 | 0.0 |
| S132N | 1.2 | 1.2 | 0.3 |
| Y135F | 1.3 | 1.5 | 0.8 |
| Y135F | 1.3 | 1.2 | 0.9 |
| Y135E | 1.5 | 1.7 | 0.8 |
| Q151I | 0.8 | 0.8 | 1.0 |
| W159S | 1.2 | 1.2 | 0.6 |
| W159H | 1.2 | 1.3 | 0.8 |
| G184D | 1.2 | 1.4 | 1.0 |
| A186H | 0.8 | 1.0 | 1.1 |
| H210Q | 0.9 | 0.9 | 1.1 |
| H210N | 1.2 | 1.2 | 1.2 |
| K242Q | 2.7 | 2.9 | 0.7 |
| K242H | 1.0 | 1.1 | 0.0 |
| S244Q | 0.7 | 0.7 | 1.2 |
| N260G | 1.1 | 0.9 | 1.0 |
| A288V | 0.8 | 0.8 | 1.2 |
| Y295N | 1.2 | 1.0 | 0.9 |
| Y295F | 1.3 | 1.2 | 1.0 |
| S323N | 1.1 | 1.0 | 1.0 |
| E341T | 1.0 | 1.0 | 1.1 |
| W439T | 0.8 | 0.9 | 1.1 |
| W439R | 1.4 | 1.4 | 1.0 |
| W439N | 1.4 | 1.4 | 1.0 |
| G476Y | 1.1 | 1.3 | 1.1 |
| QG476K | 1.2 | 1.1 | 0.9 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An alpha-amylase variant of a parent alpha-amylase having alpha-amylase activity, wherein said variant is a mature form of an alpha-amylase having amylase activity, and comprising:

a) at least 85% sequence identity to the amino acid sequence as set for in SEQ ID NO: 3;

b) a substitution at a position corresponding to position K72 or F113 of the amino acid sequence set forth in SEQ ID NO: 3, wherein said substitution for K72 is a Y or R substitution, and wherein said substitution for F113 is a V, L, C, E, D, K, Q, or Y substitution; and c) a substitution at one or more positions selected from the group consisting of: H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3; and wherein the substitutions provide an alpha-amylase variant having an improvement factor of >1.0 for a measure of stability, or an improvement factor of >1.0 for a measure of specific activity.

2. The alpha-amylase variant according to claim 1, wherein said parent alpha-amylase has at least 90% sequence identity with the amino acid sequence set forth in SEQ ID NO: 3.

3. The variant according to claim 1, comprising a substitution at one or more positions selected from the group consisting of: H1, H2, D3, G4, T5, G7, T8, I9, Q11, Y12, F13, E14, W15, N16, P18, N19, D20, Q22, W24, N25, R26, L27, H28, N29, N30, A31, Q32, L34, K35, N36, A37, I39, T40, A41, W43, I44, P45, P46, A47, W48, G50, T51, S52, Q53, N54, D55, V56, G59, A60, Y61, L63, Y64, L66, E68, F69, N70, Q71, G73, T74, V75, R76, T77, K78, K82, A83, E84, L85, R87, A88, I89, R90, S91, L92, K93, N95, G96, I97, Q98, V99, Y100, V103, H107, K108, G109, D112, E115, R116, V117, A119, V120, E121, V122, N123, Q125, N126, R127, N128, Q129, E130, V131, S132, G133, T134, Y135, I137, A139, W140, T141, G142, F143, N144, F145, P146, G147, G149, N150, Q151, S153, F155, K156, W157, R158, W159, Y160, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, R219, V222, W223, A225, N226, T227, L228, N229, L230, D231, F233, V238, I241, K242, F245, M246, W249, L250, H252, R254, G255, T257, G258, K259, N260, L261, F262, A263, Y267, W268, K269, N270, D271, G273, A274, Y278, L279, S280, K281, T282, N283, W284, T285, M286, S287, A288, V291, P292, L293, H294, N296, L297, Q299, A300, S301, S303, S304, G305, N306, L312, L313, N314, G315, T316, V318, Q319, R320, H321, P322, A325, P336, G337, E341, S342, V344, Q345, G346, W347, F348, K349, P350, L351, A352, L357, T358, Q361, G362, Y363, Q365, V366, G369, D370, Y372, G373, I374, P375, S376, D377, V379, P380, S381, Y382, R383, Q384, I386, D387, P388, L389, L390, K391, A392, Q394, Q395, Y396, A397, R400, H402, F405, D406, H407, W408, V410, T414, R415, E416, N418, A419, H421, G425, A427, T428, I429, M430, S431, G435, G436, S437, W439, M440, V442, R444, Q445, A447, G448, H452, M454, T455, G456, N457, S459, G460, T463, N465, D467, W469, H471, F473, N475, G477, and V481; wherein the positions correspond to amino acid positions in the amino acid sequence set forth in SEQ ID NO: 3, which one or more substitutions provides an improvement factor of >1.2 for a measure of specific activity in Model A detergent composition.

4. The variant according to claim 1, comprising a substitution at one or more positions selected from the group consisting of: H1, H2, G4, T5, G7, Q11, F13, E14, W15, N16, P18, N19, D20, Q22, N25, R26, N29, N30, A31, Q32, L34, A41, P46, W48, G50, T51, S52, Q53, D55, V56, G59, A60, Y61, Y64, F69, N70, Q71, G73, T74, V75, R76, T77, K78, K82, A83, R87, I89, R90, S91, L92, K93, N95, Q98, V99, Y100, H107, K108, G109, D112, E115, R116, V117, A119, V120, E121, V122, N123, N126, R127, N128, Q129, E130, V131, S132, G133, T134, Y135, I137, A139, W140, T141, G142, F143, N144, F145, P146, G147, G149, N150, Q151, S153, F155, K156, W157, R158, W159, Y160, F162, D163, G164, T165, D166, W167, D168, Q169, S170, R171, Q172, L173, A174, N175, R176, I177, Y178, K179, F180, R181, G184, K185, A186, W187, D188, W189, V191, T193, E194, N197, D199, Y200, M202, Y203, A204, D205, V206, D209, H210, P211, E212, N215, L217, R219, W223, N226, V238, I241, K242, F245, G258, K259, N260, F262, A263, K269, N270, D271, G273, A274, Y278, L279, K281, W284, T285, S287, P292, N296, L297, Q299, S301, N306, L312, G315, V318, Q319, R320, H321, P322, A325, P336, G337, E341, S342, V344, G346, F348, K349, P350, L351, Q361, G362, Y363, Y368, G369, D370, Y372, G373, S376, D377, V379, P380, S381, Y382, Q384, D387, Q394, Q395, A397, R400, H402, H407, W408, V410, R415, N418, H421, S431, G435, G436, W439, M440, Q445, A447, M454, G456, N465, D467, N475, G477, and V481; wherein the positions correspond to amino acid positions in the amino acid sequence set forth in SEQ ID NO: 3, which one or more substitutions provides an improvement factor of >1.4 for a measure of specific activity in Model A detergent composition.

5. The variant according to claim 1, comprising a substitution at one or more positions selected from the group consisting of: H1, G7, F13, E14, W15, N16, N19, D20, Q22, R26, N29, N30, A31, Q32, P46, W48, G50, T51, S52, Q53, D55, G59, A60, Y64, N70, Q71, G73, T74, V75, K78, R90, Y100, H107, K108, G109, D112, R116, V117, A119, E121, N123, N126, R127, N128, E130, V131, S132, G133, T134, Y135, I137, A139, W140, T141, G142, N144, F145, P146, G147, G149, N150, Q151, F155, K156, R158, W159, Y160, D163, G164, T165, D166, W167, S170, R171, Q172, L173, R176, Y178, K179, R181, K185, A186, W187, D188, W189, V191, E194, D199, Y200, M202, Y203, A204, D205, H210, N215, L217, R219, W223, V238, K242, F245, G258, F262, K269, N270, A274, T285, S287, N296, L312, V318, H321, P322, A325, G337, E341, S342, K349, P350, Q361, G362, Y368, G369, D377, S381, Q384, D387, R400, W408, R415, N418, G435, Q445, M454, G477, and V481; wherein the positions correspond to amino acid positions in the amino acid sequence set forth in SEQ ID NO: 3, which one or more substitutions provides an improvement factor of >1.6 for a measure of specific activity in Model A detergent composition.

6. The variant according to claim 1, comprising a substitution at one or more positions selected from the group consisting of H1, H2, D3, G4, T5, G7, T8, I9, M10, Q11, Y12, F13, E14, W15, N16, P18, N19, Q22, W24, N25, R26, L27, H28, N29, N30, A31, Q32, N33, L34, K35, N36, A37, G38, I39, T40, A41, I42, W43, I44, P45, P46, A47, W48, G50, T51, S52, Q53, N54, D55, G59, A60, Y61, L63, Y64, L66, E68, F69, N70, Q71, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, D112, E115, R116, V117, A119, V120, E121, V122, N123, Q125, N126, R127, N128, Q129, E130, V131, S132, G133, T134, Y135, I137, E138, A139, W140, T141, G142, F143, N144, F145, P146, G147, G149, N150, Q151, S153, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, V222, W223, Y224, A225, N226, T227, L228, N229, L230, D231, F233, V238, I241, K242, F245, M246, W249, L250, H252, V253, R254, G255, Q256, T257, G258, K259, N260, L261, F262, A263, V264, Y267, W268, K269, N270, D271, G273, A274, E276, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, L312, L313, N314, G315, T316, V318, Q319, R320, H321, P322, A325, V326, T327, N329, N331, P336, G337, E341, S342, V344, Q345, G346, W347, F348, K349, P350, L351, A352, T355, L357, T358, E360, Q361, G362, Y363, Q365, V366, Y368, G369, D370, Y372, G373, I374, P375, S376, D377, V379, P380, S381, Y382, R383, Q384, I386, D387, P388, L389, L390, K391, A392, Q394, Q395, Y396, A397, R400, H402, D403, F405, D406, H407, W408, V410, I411, T414, R415, E416, N418, A419, S420, H421, S424, G425, A427, T428, I429, M430, S431, G435, G436, S437, K438, W439, M440, Y441, V442, R444, Q445, K446, A447, G448, V450, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence as set forth in SEQ ID NO: 3, and wherein the one or more substitutions provides a variant having an IF of >1.2 for a measure of specific activity in Model X detergent composition.

7. The variant according to claim 1, comprising a substitution at one or more positions selected from the group consisting of: H1, H2, D3, T5, G7, I9, E14, W15, N16, V17, Q22, H23, W24, N25, R26, H28, N29, N33, N36, A37, G38, I39, T40, A41, I42, I44, W48, S52, Q53, N54, D55, V56, G59, A60, L63, E68, G73, T74, V75, R76, T81, A83, E86, R90, S91, L92, N95, I97, Q98, V99, Y100, V103, H107, K108, G109, G110, A111, D112, T114, R116, V117, Q118, V120, V122, N123, P124, N126, N128, Q129, V131, G133, Q136, I137, E138, A139, W140, T141, G142, F143, N144, F145, P146, G149, Q151, S153, S154, F155, K156, Y160, T165, D166, Q169, S170, R171, Q172, L173, A174, N175, R176, K179, R181, K185, A186, T193, N195, G196, Y198, Y203, D205, V206, D209, H210, E212, V213, I214, N215, L217, N218, W220, G221, W223, N226, T227, L228, D231, F233, V238, H240, K242, S244, R247, D248, L250, G251, H252, T257, G258, K259, N260, L261, K269, L272, G273, L275, E276, N277, L279, K281, T285, M286, A288, P292, L293, H294, Y295, N296, L297, Q299, A300, N302, S303, S304, G305, N306, R310, N311, L312, L313, G315, T316, Q319, R320, H321, T327, T334, P336, E338, E341, S342, V344, G346, W347, F348, P350, L351, A354, T355, T358, E360, Q361, Y363, Q365, F367, Y368, G369, G373, I374, P375, S376, D377, V379, S381, Y382, Q384, I386, D387, P388, L389, L390, K391, A392, Q394, Q395, Y396, A397, Y398, R400, H402, D403, Y404, F405, D406, D409, V410, R415, E416, N418, A419, S420, P422, S424, G425, L426, A427, M430, S431, D432, G435, W439, Y441, Q445, K446, A447, V450, H452, M454, G456, S459, F473, and N475; wherein the positions correspond to amino acid positions in the amino acid sequence set forth in SEQ ID NO: 3, which one or more substitution provides an improvement factor of >1.2 for a measure of stability.

8. The variant according to claim 1, comprising a substitution at one or more positions selected from the group consisting of: H1, D3, G7, N16, V17, Q22, H28, N33, N36, T40, W48, S52, Q53, N54, D55, V56, G59, A60, V75, R76, N95, V99, G109, A111, D112, F113, T114, R116, V117, Q118, V122, N123, P124, N126, N128, V131, Q136, I137, E138, A139, T141, G142, F143, N144, F145, P146, G149, Q151, S153, S154, K156, Y160, T165, D166, Q169, S170, R171, Q172, A174, R176, R181, K185, A186, T193, N195, Y203, D205, V206, D209, E212, V213, N215, N218, W220, G221, N226, F233, K242, D248, L250, G251, H252, G258, N260, K269, G273, E276, N277, T285, P292, L293, H294, N296, Q299, S304, G305, N306, R310, N311, L312, Q319, R320, H321, T327, T334, P336, E338, E341, G346, W347, L351, A354, Y363, G373, I374, P375, S376, D377, V379, S381, Y382, Q384, P388, L389, L390, Q394, Q395, Y398, R400, H402, Y404, V410, E416, N418, A419, S420, P422, M430, S431, G435, Q445, A447, M454, F473, and N475; wherein the positions correspond to amino acid positions in the amino acid sequence set forth in SEQ ID NO: 3, which one or more substitutions provides an improvement factor of >1.5 for a measure of stability.

9. The variant according to claim 1, comprising a substitution in one or more positions selected from the group consisting of: H1, H2, T5, G7, I9, Q11, E14, W15, N19, Q22, W24, N25, R26, H28, N29, N30, A31, L34, K35, I39, T40, A41, I42, I44, A47, W48, T51, S52, Q53, V56, G59, T74, V75, I89, R90, S91, L92, N95, I97, Q98, Y100, K108, F113, R116, V117, N126, N128, Q129, G133, A139, W140, T141, F143, F145, P146, Q151, K156, R158, H161, T165, D166, Q169, S170, R171, Q172, L173, A174, N175, K179, R181, G184, K185, A186, T193, Y203, D209, H210, E212, V213, N215, L217, N218, R219, V222, N226, T227, L228, K242, K245, L250, H252, V253, T257, G258, K259, N260, V264, K269, L279, K281, M286, P292, L293, Y295, L297, Q299, N306, L312, G315, T316, V318, R320, H321, S323, T327, V329, P336, G337, E341, S342, V344, Q345, G346, W347, P350, L351, Q361, Y363, Y368, I374, S376, V379, P380, S381, D387, L390, A392, Q395, H402, F405, T414, E416, N418, A419, M430, S431, G435, W439, K446, V450, G456, S459, N465, G476, and W482; wherein the positions correspond to amino acid positions in the amino acid sequence set forth in SEQ ID NO: 3, which one or more substitutions provides an improvement factor of >1.0 for a measure of stability and an improvement factor of >1.0 for a measure of specific activity in Model A detergent composition.

10. The variant according to claim 1, comprising a substitution in one or more positions selected from the group consisting of: H1, G7, Q22, N25, R26, H28, N29, W48, S52, Q53, V56, G59, T74, V75, R90, N95, Q98, K108, F113, R116, V117, N128, Q129, G133, A139, W140, T141, F143, F145, P146, Q151, K156, T165, Q169, S170, R171, Q172, A174, K179, R181, K185, A186, T193, Y203, D209, E212, N215, L217, N226, K242, K259, N260, K269, K281, P292, L293, L297, N306, L312, G315, R320, H321, P336, V344, P350, Y363, Y368, S381, D387, A392, Q395, E416, N418, and S431; wherein the positions correspond to amino acid positions in the amino acid sequence set forth in SEQ ID NO: 3, which one or more substitutions provides an improvement factor of >1.3 for a measure of stability and an improvement factor of >1.3 for a measure of specific activity.

11. An alpha-amylase variant according to claim 1, wherein said variant is a mature form of alpha-amylase having amylase activity and comprising a substitution at one or more positions selected from the group consisting of: E14, D20, Q22, G59, R116, A119, S132, G133, Y135, K156, R158, W159, Y160, K185, W187, Y202, D236, V238, K242, G337, E341, Y368, G369, D377, Y382, and K445, wherein the positions correspond to amino acids in the amino acid sequence set forth in SEQ ID NO: 3; and wherein the substitution provides at least one improved property selected from the group consisting of improved wash performance, improved detergent stability, and improved thermostability.

12. An alpha-amylase variant according to claim 1, wherein said variant is a mature form of alpha-amylase having amylase activity and comprising a substitution at one or more positions selected from the group consisting of: E14, D20, Q22, G59, R116, A119, S132, G133, Y135, K156, R158, W159, Y160, K185, W187, Y202, D236, V238, K242, G337, E341, Y368, G369, D377, Y382, and K445, wherein the positions correspond to amino acids in the amino acid sequence set forth in SEQ ID NO: 3; and wherein the substitution provides an alpha-amylase variant having an improvement factor of >1.0 for a measure of specific activity at pH 8.0 and 25° C., and an improvement factor of >1.0 for a measure of stability in a detergent composition and for thermostability.

13. The variant according to claim 1, wherein the amino acid substituted with in the particular position is substituted with A, C, D, E, F, G, H, I, K, L, M, N, P, Q, R, S, T, V, W, or Y, with the proviso that the amino acid substituted with is different from the naturally-occurring amino acid in said particular position.

14. The variant according to claim 1, further comprising a pairwise deletion of the amino acid residues corresponding to 181, 182, 183 and 184 of the amino acid sequence set forth in SEQ ID NO: 3, with the proviso that when the amino acids in positions corresponding to 181 or 184 has been substituted, the pairwise deletion is in the positions corresponding to 182 and 183 of the amino acid sequence set forth in SEQ ID NO: 3.

15. An alpha-amylase variant, wherein said variant is a mature form having amylase activity and comprising:
   a) at least 85% sequence identity to the amino acid sequence as set forth in SEQ ID NO: 3;

b) a substitution at a position corresponding to position K72 or F113 of the amino acid sequence as set forth in SEQ ID NO: 3, wherein said substitution for K72 is a Y or R substitution, and wherein said substitution for F113 is a V, L, C, E, D, K, Q, or Y substitution;

c) a deletion or substitution at two or more positions corresponding to positions R181, G182, D183, and G184 of the amino acid sequence set forth in SEQ ID NO: 3; and d) a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3.

16. The variant according to claim 1, wherein said variant comprises a substitution at 1, 2, 3, 4, 5, 6, 7, 8, 9, or 10 positions.

17. A polynucleotide encoding the variant according to claim 1.

18. A nucleic acid construct comprising the polynucleotide according to claim 17.

19. An expression vector comprising the polynucleotide according to claim 17.

20. An isolated recombinant host cell comprising the polynucleotide according to claim 17.

21. A composition comprising the variant according to claim 1.

22. The composition according to claim 21, further comprising at least one further active component.

23. The composition according to claim 22, wherein said further active component is an enzyme.

24. The composition according to claim 21, which is a detergent composition.

25. The composition according to claim 21, which is a liquid laundry or liquid dish wash composition, or a powder laundry or powder dish wash composition.

26. A method of improving the performance of a parent alpha-amylase having the amino acid sequence of SEQ ID NO: 3 or 4, or having at least 85% sequence identity hereto, said method comprising the steps of:

a) introducing a pairwise deletion or substitution at two or more positions corresponding to positions R181, G182, D183, and G184 of the amino acid sequence set forth in SEQ ID NO: 3;

b) introducing a substitution at a position corresponding to position K72 or F113 of the amino acid sequence set forth in SEQ ID NO: 3, wherein said substitution for K72 is a Y or R substitution, and wherein said substitution for F113 is a V, L, C, E, D, K, Q, or Y substitution; and c) introducing a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3; said method thereby providing an alpha-amylase variant of said parent alpha-amylase, wherein said variant has at least 85% sequence identity to the amino acid sequence as set forth in SEQ ID NOs: 3 or 4, and wherein said variant has alpha-amylase activity and improved performance as compared to said parent alpha-amylase.

27. A method of improving the stability of a parent alpha-amylase having the amino acid sequence of SEQ ID NO: 3 or 4, or having at least 85% sequence identity hereto, said method comprising the steps of:

a) introducing a pairwise deletion or substitution at two or more positions corresponding to positions R181, G182, D183, and G184 of the amino acid sequence set forth in SEQ ID NO: 3;

b) introducing a substitution at a position corresponding to position K72 or F113 of the amino acid sequence set forth in SEQ ID NO: 3, wherein said substitution for K72 is a Y or R substitution, and wherein said substitution for F113 is a V, L, C, E, D, K, Q, or Y substitution; and c) introducing a substitution at one or more positions selected from the group consisting of; H1, H2, D3, G4, T5, G7, T8, I9, M10, Q11, Y12, F13, E14, W15, N16, V17, P18, N19, D20, Q22, H23, W24, N25, R26, L27, H28, N29, N30, A31, Q32, N33, L34, K35, N36, A37, G38, I39, T40, A41, I42, W43, I44, P45, P46, A47, W48, K49, G50, T51, S52, Q53, N54, D55, V56, G59, A60, Y61, L63, Y64, L66, E68, F69, N70, Q71, G73, T74, V75, R76, T77, K78, T81, K82, A83, E84, L85, E86, R87, A88, I89, R90, S91, L92, K93, N95, G96, I97, Q98, V99, Y100, V103, H107, K108, G109, G110, A111, D112, T114, E115, R116, V117, Q118, A119, V120, E121, V122, N123, P124, Q125, N126, R127, N128, Q129, E130, V131, S132, G133, T134, Y135, Q136, I137, E138, A139, W140, T141, G142, F143, N144, F145, P146, G147, G149, N150, Q151, S153, S154, F155, K156, W157, R158, W159, Y160, H161, F162, D163, G164, T165, D166, W167, D168, Q169, S170, R171, Q172, L173, A174, N175, R176, I177, Y178, K179, F180, R181, G184, K185, A186, W187, D188, W189, E190, V191, D192, T193, E194, N195, G196, N197, Y198, D199, Y200, M202, Y203, A204, D205, V206, M208, D209, H210, P211, E212, V213, I214, N215, L217, N218, R219, W220, G221, V222, W223, Y224, A225, N226, T227, L228, N229, L230, D231, F233, V238, H240, I241, K242, S244, F245, M246, R247, D248, W249, L250, G251, H252, V253, R254, G255, Q256, T257, G258, K259, N260, L261, F262, A263, V264, Y267, W268, K269, N270, D271, L272, G273, A274, L275, E276, N277, Y278, L279, S280, K281, T282, N283, W284, T285, M286, S287, A288, V291, P292, L293, H294, Y295, N296, L297, Y298, Q299, A300, S301, N302, S303, S304, G305, N306, Y307, M309, R310, N311, L312, L313, N314, G315, T316, V318, Q319, R320, H321, P322, S323, A325, V326, T327, F328, V329, N331, T334, P336, G337, E338, E341, S342, V344, Q345, G346, W347, F348, K349, P350, L351, A352, A354, T355, L357, T358, E360, Q361, G362, Y363, Q365, V366, F367, Y368, G369, D370, Y372, G373, I374, P375, S376, D377, V379, P380, S381, Y382, R383, Q384, I386, D387, P388, L389, L390, K391, A392, Q394, Q395, Y396, A397, Y398, R400, H402, D403, Y404, F405, D406, H407, W408, D409, V410, I411, T414, R415, E416, N418, A419, S420, H421, P422, S424, G425, L426, A427, T428, I429, M430, S431, D432, G435, G436, S437, K438, W439, M440, Y441, V442, R444, Q445, K446, A447, G448, V450, W451, H452, D453, M454, T455, G456, N457, S459, G460, T463, I464, N465, Q466, D467, W469, H471, F473, N475, G476, G477, V481, and W482; wherein the positions correspond to amino acid positions in the amino acid sequence set forth in SEQ ID NO: 3; said method thereby providing an alpha-amylase variant of said parent alpha-amylase, wherein said variant has at least 85% sequence identity to the amino acid sequence as set forth in SEQ ID NOs: 3 or 4, and wherein said variant has alpha-amylase activity and improved stability as compared to said parent alpha-amylase.

28. The method according to claim 26, wherein said variant has at least 50% of the activity of the parent alpha-amylase having the amino acid sequence of SEQ ID NOs: 3 or 4.

* * * * *

SEQUENCE LISTING

Sequence total quantity: 6
SEQ ID NO: 1               moltype = DNA   length = 1458
FEATURE                    Location/Qualifiers
source                     1..1458
                           mol_type = genomic DNA
                           organism = Bacillus sp.
SEQUENCE: 1
catcacgatg ggacgaacgg aacgattatg cagtattttg aatggaacgt tccgaatgat   60
ggacaacatt ggaaccgctt acacaacaac gctcaaaatt taaaaaatgc cggaattaca   120
gcaatctgga ttccacctgc gtggaaagga acgagccaaa atgatgtagg ctacggtgcg   180
tatgaccttt atgaccttgg tgaatttaac caaaaaggaa cggtccgtac gaaatatgga   240
acaaaagcag aattagaacg agcgattcgt tcgttaaagg cgaacgggat tcaagtgtat   300
ggcgatgttg ttatgaacca taaaggcgga gctgatttca ccgagcgtgt tcaagcggtt   360
gaagtgaacc cgcaaaaccg aaaccaagaa gtgtctggca cttatcaaat cgaagcatgg   420
acagggttca attttcctgg acgtggcaat caacattctt cgtttaaatg gcgctggtat   480
catttcgatg ggacggattg ggaccagtct cgccaactcg caaatcgtat ttataagttt   540
agaggagacg gaaaagcatg ggactgggaa gttgacactg aaaatgggaa ctatgattac   600
ttaatgtatg cagacgttga catggatcat ccagaagtga ttaacgaact aaaccgttgg   660
ggcgtctggt acgcgaatac ccttaattta gacggcttcc gactggatgc agtgaaacat   720
attaaattta gcttcatgcg tgattggtta gggcatgttc gcgggcaaac gggcaagaat   780
cttttttgccg ttgcagagta ttggaagaat gacctagggg ctttagaaaa ttatttaagc   840
aaaacaaatt ggacgatgag cgcctttgat gttccgcttc attacaacct ttatcaagcg   900
tcaaatagta gcggaaatta cgacatgaga aacttgttaa atggaacact cgttcaacgt   960
catccgagcc atgcggttac gtttgtcgat aaccacgaca cagacctgg agaagccctc   1020
gaatcgttcg ttcaaggctg gtttaaacca ctagcttatg caacgattct tacgagagag   1080
caaggctacc cacaagtgtt ttacggcgat tattatggca tcccaagtga cggtgttcca   1140
agctaccgtc aacagatcga cccactttta aaagctcgtc aacaatatgc ttatggtaga   1200
cagcacgatt actttgatca ttgggatgta attggctgga cacgtgaagg aaacgcatct   1260
cacccgaact caggacttgc aaccattatg tctgatggtc caggtggatc aaaatgggatg   1320
tatgttggcc gtcagaaagc tggcgaagtg tggcatgaca tgactggaaa ccgcagtggc   1380
actgtgacaa ttaatcaaga cggctgggga cactttttg tcaacggcgg ctctgtctcc   1440
gtatgggtga aacgataa                                                 1458

SEQ ID NO: 2               moltype = AA   length = 514
FEATURE                    Location/Qualifiers
source                     1..514
                           mol_type = protein
                           organism = Bacillus sp.
SEQUENCE: 2
MNRWKAAFSW MLSLALVFTL FYTPSSASAH HDGTNGTIMQ YFEWNVPNDG QHWNRLHNNA   60
QNLKNAGITA IWIPPAWKGT SQNDVGYGAY DLYDLGEFNQ KGTVRTKYGT KAELERAIRS   120
LKANGIQVYG DVVMNHKGGA DFTERVQAVE VNPQNRNQEV SGTYQIEAWT GFNFPGRGNQ   180
HSSFKWRWYH FDGTDWDQSR QLANRIYKFR GDGKAWDWEV DTENGNYDYL MYADVDMDHP   240
EVINELNRWG VWYANTLNLD GFRLDAVKHI KFSFMRDWLG HVRGQTGKNL FAVAEYWKND   300
LGALENYLSK TNWTMSAFDV PLHYNLYQAS NSSGNYDMRN LLNGTLVQRH PSHAVTFVDN   360
HDTQPGEALE SFVQGWFKPL AYATILTREQ GYPQVFYGDY YGIPSDGVPS YRQQIDPLLK   420
ARQQYAYGRQ HDYFDHWDVI GWTREGNASH PNSGLATIMS DGPGGSKWMY VGRQKAGEVW   480
HDMTGNRSGT VTINQDGWGH FFVNGGSVSV WVKR                               514

SEQ ID NO: 3               moltype = AA   length = 485
FEATURE                    Location/Qualifiers
source                     1..485
                           mol_type = protein
                           organism = Bacillus sp.
SEQUENCE: 3
HHDGTNGTIM QYFEWNVPND GQHWNRLHNN AQNLKNAGIT AIWIPPAWKG TSQNDVGYGA   60
YDLYDLGEFN QKGTVRTKYG TKAELERAIR SLKANGIQVY GDVVMNHKGG ADFTERVQAV   120
EVNPQNRNQE VSGTYQIEAW TGFNFPGRGN QHSSFKWRWY HFDGTDWDQS RQLANRIYKF   180
RGDGKAWDWE VDTENGNYDY LMYADVDMDH PEVINELNRW GVWYANTLNL DGFRLDAVKH   240
IKFSFMRDWL GHVRGQTGKN LFAVAEYWKN DLGALENYLS KTNWTMSAFD VPLHYNLYQA   300
SNSSGNYDMR NLLNGTLVQR HPSHAVTFVD NHDTQPGEAL ESFVQGWFEA LAYATILTRE   360
QGYPQVFYGD YYGIPSDGVP SYRQQIDPLL KARQQYAYGR QHDYFDHWDV IGWTREGNAS   420
HPNSGLATIM SDGPGGSKWM YVGRQKAGEV WHDMTGNRSG TVTINQDGWG HFFVNGGSVS   480
VWVKR                                                               485

SEQ ID NO: 4               moltype = AA   length = 483
FEATURE                    Location/Qualifiers
source                     1..483
                           mol_type = protein
                           organism = Bacillus sp.
SEQUENCE: 4
HHDGTNGTIM QYFEWNVPND GQHWNRLHNN AQNLKNAGIT AIWIPPAWKG TSQNDVGYGA   60
YDLYDLGEFN QKGTVRTKYG TKAELERAIR SLKANGIQVY GDVVMNHKGG ADFTERVQAV   120
EVNPQNRNQE VSGTYQIEAW TGFNFPGRGN QHSSFKWRWY HFDGTDWDQS RQLANRIYKF   180
RGKAWDWEVD TENGNYDYLM YADVDMDHPE VINELNRWGV WYANTLNLDG FRLDAVKHIK   240
FSFMRDWLGH VRGQTGKNLF AVAEYWKNDL GALENYLSKT NWTMSAFDVP LHYNLYQASN   300
SSGNYDMRNL LNGTLVQRHP SHAVTFVDNH DTQPGEALES FVQGWFKPLA YATILTREQG   360
YPQVFYGDYY GIPSDGVPSY RQQIDPLLKA RQQYAYGRQH DYFDHWDVIG WTREGNASHP   420

-continued

```
NSGLATIMSD GPGGSKWMYV GRQKAGEVWH DMTGNRSGTV TINQDGWGHF FVNGGSVSVW  480
VKR                                                                483

SEQ ID NO: 5              moltype = DNA  length = 27
FEATURE                   Location/Qualifiers
misc_feature              1..27
                          note = PnMi4490 forward primer
source                    1..27
                          mol_type = other DNA
                          organism = Synthetic construct
SEQUENCE: 5
caatccaaga gaaccctgat acggatg                                      27

SEQ ID NO: 6              moltype = DNA  length = 23
FEATURE                   Location/Qualifiers
misc_feature              1..23
                          note = PnMi4491 forward primer
source                    1..23
                          mol_type = other DNA
                          organism = Synthetic construct
SEQUENCE: 6
cggaacgcct ggctgacaac acg                                          23
```